United States Patent
Devaraj et al.

(10) Patent No.: US 11,267,842 B2
(45) Date of Patent: Mar. 8, 2022

(54) ENZYMATIC MODIFICATION OF NUCLEIC ACIDS

(71) Applicant: The Regents of the University of California, Oakland, CA (US)

(72) Inventors: Neal K. Devaraj, La Jolla, CA (US); Seth C. Alexander, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 582 days.

(21) Appl. No.: 15/553,568

(22) PCT Filed: Mar. 3, 2016

(86) PCT No.: PCT/US2016/020778
§ 371 (c)(1),
(2) Date: Aug. 24, 2017

(87) PCT Pub. No.: WO2016/141243
PCT Pub. Date: Sep. 9, 2016

(65) Prior Publication Data
US 2018/0148764 A1    May 31, 2018

Related U.S. Application Data

(60) Provisional application No. 62/214,074, filed on Sep. 3, 2015, provisional application No. 62/127,596, filed on Mar. 3, 2015.

(51) Int. Cl.
| | |
|---|---|
| *C12Q 1/68* | (2018.01) |
| *C07H 19/04* | (2006.01) |
| *C07D 487/04* | (2006.01) |
| *C12P 19/34* | (2006.01) |
| *C07D 519/00* | (2006.01) |
| *C07H 21/00* | (2006.01) |
| *C12Q 1/6806* | (2018.01) |
| *C07H 1/00* | (2006.01) |
| *C12Q 1/48* | (2006.01) |
| *C07F 5/02* | (2006.01) |

(52) U.S. Cl.
CPC ........... *C07H 19/04* (2013.01); *C07D 487/04* (2013.01); *C07D 519/00* (2013.01); *C07F 5/022* (2013.01); *C07H 1/00* (2013.01); *C07H 21/00* (2013.01); *C12P 19/34* (2013.01); *C12Q 1/48* (2013.01); *C12Q 1/6806* (2013.01); *C12Y 204/02029* (2013.01); *G01N 2333/91142* (2013.01); *G01N 2500/02* (2013.01)

(58) Field of Classification Search
CPC ........ C07H 19/00; C07H 19/04; C07H 21/00; C12P 19/34; C12Q 1/6806; C07D 487/04; C07D 519/00
See application file for complete search history.

(56) References Cited

U.S. PATENT DOCUMENTS

| | | | |
|---|---|---|---|
| 5,607,842 A | 3/1997 | Cohen et al. | |
| 2009/0298909 A1 | 12/2009 | Pachuk et al. | |
| 2013/0012527 A1 | 1/2013 | Breaker et al. | |
| 2017/0258797 A1* | 9/2017 | Kelly | A61K 45/06 |

FOREIGN PATENT DOCUMENTS

JP    62228019    * 10/1987

OTHER PUBLICATIONS

Hiroshi, Akimoto et al. Journal of Medicinal Chemistry (1986), 29(9), 1749-53. (Year: 1986).*
Hiroshi Akimoto et al. J. Chem Soc. Perkin Trans. I 1988 (Year: 1988).*
Hurt, J.K. et al. (2007, e-published Jul. 10, 2007). "Site-specific modification of Shigella flexneri virF mRNA by tRNA-guanine transglycosylase in vitro," *Nucleic Acids Res* 35(14):4905-4913.
Okada, N. et al. (Apr. 25, 1979). "Novel mechanism of post-transcriptional modification of tRNA. Insertion of bases of Q precursors into tRNA by a specific tRNA transglycosylase reaction," *J Biol Chem* 254(8):3067-3073.
Ramzaeva, N. et al. (2007). "Electrophilic Substitution at C(7) of a Protected 7-Deaza-2'-deoxyguanosine—The 2'-Deoxyribonucleoside Parent Analogue of Queuosine," located at <http:www.mdpi.org/molbank/molbank2007/m522.html> last visited Sep. 16, 2018, 3 pages.
International Search Report dated Aug. 12, 2016, for PCT Application No. PCT/US2016/020778, filed Mar. 3, 2016, 6 pages.
Written Opinion dated Aug. 12, 2016, for PCT Application No. PCT/US2016/020778, filed Mar. 3, 2016, 8 pages.

* cited by examiner

*Primary Examiner* — Jezia Riley
(74) *Attorney, Agent, or Firm* — Irina E. Britva; Mintz, Levin, Cohn, Ferris, Glovsky and Popeo, P.C.

(57) ABSTRACT

There are provided, inter alia, methods and reagents for labeling nucleic acids.

22 Claims, 20 Drawing Sheets

Specification includes a Sequence Listing.

|  | PreQ1-C6-TO-N | PreQ1-PEG3-TO-ME |
|---|---|---|
| TGT enzyme | 100 nM | 10 μM |
| mRNA | 100 nM | 100 nM |
| Probe | 100 nM | 20 μM |

FIG. 19B
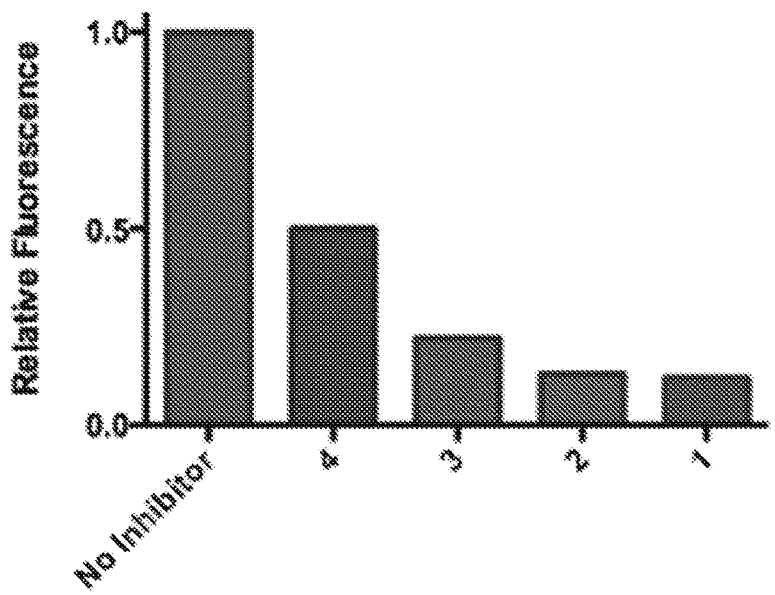
FIG. 20A
| RNA Oligonucleotide | Sequence |
|---|---|
| ECY-A1 | 5'GCA GAC UGU AAA UCU GC3' |
| ECY-A1ΔC | 5'GCA GAC UCU AAA UCU GC3' |
| ECY-X1 | 5'CG UCU AAA UGU CAG ACG3' |
FIG. 20B
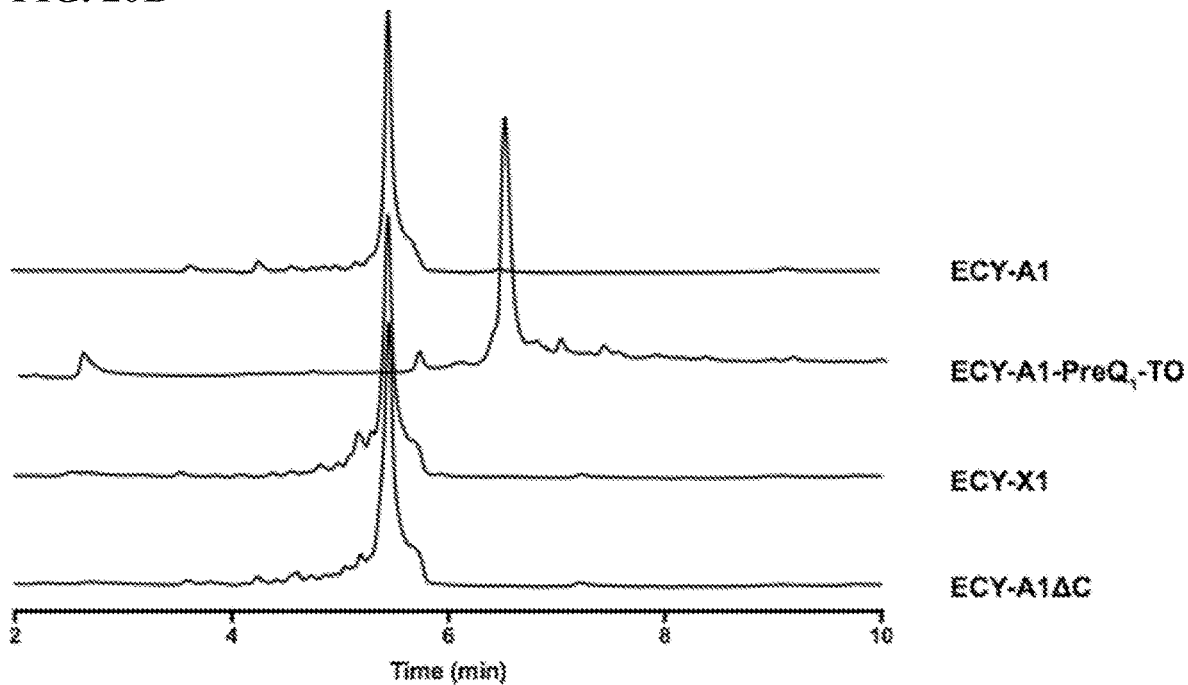

ENZYMATIC MODIFICATION OF NUCLEIC ACIDS

CROSS-REFERENCES TO RELATED APPLICATIONS

This application claims the benefit of U.S. Provisional Application No. 62/127,596, filed Mar. 3, 2015, and U.S. Provisional Application No. 62/214,074, filed Sep. 3, 2015, each of which is incorporated herein by reference in its entirety and for all purposes.

STATEMENT AS TO RIGHTS TO INVENTIONS MADE UNDER FEDERALLY SPONSORED RESEARCH AND DEVELOPMENT

This invention was made with Government support under grant number AI082434 awarded by the National Institutes of Health. The Government has certain rights in the invention.

REFERENCE TO A "SEQUENCE LISTING," A TABLE, OR A COMPUTER PROGRAM LISTING APPENDIX SUBMITTED AS AN ASCII FILE

The Sequence Listing written in file 48537-547001WO_ST25.TXT, created Mar. 2, 2016, 9,685 bytes, machine format IBM-PC, MS-Windows operating system, is hereby incorporated by reference.

BACKGROUND OF THE INVENTION tRNA Guanine Transglycosylases (TGTs) are a well characterized class of enzymes that extend through all types of life (archaea, eubacteria and eukaryotes). While different classes of TGTs have different substrates for transglycosylation, they all achieve the ultimate goal of guanine replacement with queuine at the wobble position within the anticodon loop of certain tRNAs. While mammalian TGTs can incorporate the final product queuine, bacterial and archaea TGTs selectively incorporate precursors of queuine that later get modified by other enzymes to yield queuine post incorporation. Of the three branches of life, bacterial TGTs have been studied the most in depth with a high resolution crystal structure including bound tRNA, Guanine, and natural known Queuine derivative preQ1. Several potent inhibitors have been discovered, as well as a few derivatives with poor substrate selectivity outside of their natural substrates. Additionally work has been accomplished that determines the minimal binding domain of a single hairpin stem loop of the tRNA substrate. However, this enzyme has not been exploited for the purposes of tagging or labeling RNA in vitro or in vivo. Furthermore, few examples exist in the literature utilizing any enzyme to accomplish a labeling reaction of RNA with an enzymatic covalent modification. The approaches, however, can be limited in specificity and to specific types of RNA (such as mRNA) and do not provide a short RNA recognition sequence for covalent single step labeling reactions capable of a fluorogenic response nor a wide substrate scope of labels for a variety of applications.

There is, therefore, an unmet need for methods and reagents for the incorporation of unnatural residues (e.g., nucleoside derivatives such as PreQ1 analogs and the like) bearing bioorthogonal handles, fluorophores, and other groups to be incorporated into a nucleic acid (e.g., RNA stem loop from bacterial Tyrosine tRNA site) specifically replacing the Guanine at the wobble position with a nucleobase derivative (e.g., preQ1 and derivatives thereof).

BRIEF SUMMARY OF THE INVENTION

In a first aspect, there is provided a method for labeling a nucleic acid. The method includes contacting a nucleic acid including native nucleobases with a transglycosylase and a nucleoside derivative under conditions suitable to exchange at least one of the native nucleobases for the nucleoside derivative, thereby providing a labeled nucleic acid.

In another aspect, there is provided a compound with structure of Formula (I)

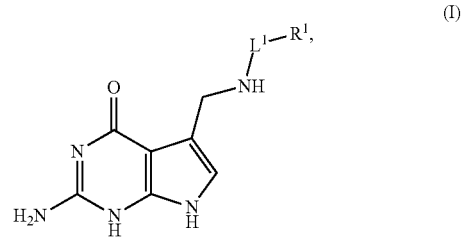

(I)

wherein $L^1$ is a divalent linking moiety; and $R^1$ is a labeling moiety.

In another aspect, there is provide a method of producing a labeled RNA. The method includes contacting a compound as disclosed herein with an RNA fragment under conditions suitable for incorporation the compound into the RNA fragment, thereby affording a labeled RNA.

In further aspects, there is provided a compound of structural Formula (II):

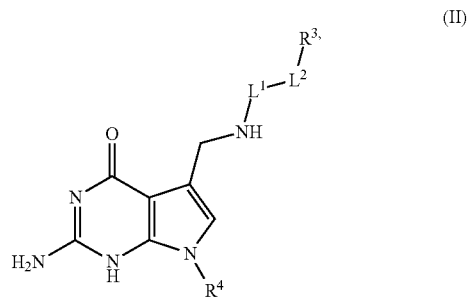

(II)

or a salt thereof.

In the compound of Formula II, $L^1$ is a bond, substituted or unsubstituted alkylene or substituted or unsubstituted heteroalkylene, a detectable moiety, hydrogen, halogen, $-CX^{1.1}{}_3$, $-CHX^{1.1}{}_2$, $-CH_2X^{1.1}$, $-CN$, $-SO_{n1}R^{1A}$, $-SO_{v1}NR^{1B}R^{1C}$, $-NHNR^{1B}R^{1C}$, $-ONR^{1B}R^{1C}$, $-NHC(O)NHNR^{1B}R^{1C}$, $-NHC(O)NR^{1B}R^{1C}$, $-NR^{1B}R^{1C}$, $-C(O)R^{1D}$, $-C(O)OR^{1D}$, $-C(O)NR^{1B}R^{1C}$, $-OR^{1A}$, $-NR^{1B}SO_2R^{1A}$, $-NR^{1B}C(O)R^{1D}$, $-NR^{1B}C(O)OR^{1D}$, $-NR^{1B}OR^{1D}$, $-OCX^{1.1}{}_3$, $-OCHX^{1.1}{}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $L^2$ is a bond, substituted or unsubstituted alkylene or substituted or unsubstituted heteroalkylene, a detectable moiety, hydrogen, halogen, $-CX^{2.1}{}_3$, $-CHX^{2.1}{}_2$, $-CH_2X^{2.1}$, $-CN$, $-SO_{n1}R^{2A}$, $-SO_{v1}NR^{2B}R^{2C}$, $-NHNR^{2B}R^{2C}$, —ONR$^{2B}$R$^{2C}$, —NHC(O)NHNR$^{2B}$R$^{2C}$, —NHC(O)NR$^{2B}$R$^{2C}$, —N(O)$_{m1}$, —NR$^{2B}$R$^{2C}$, —C(O)R$^{2D}$, —C(O)OR$^{2D}$, —C(O)NR$^{2B}$R$^{2C}$, —OR$^{2A}$, —NR$^{2B}$SO$_2$R$^{2A}$, —NR$^{2B}$C(O)R$^{2D}$, —NR$^{2B}$C(O)OR$^{2D}$, —NR$^{2B}$OR$^{2D}$, —OCX$^{2.1}_3$, —OCHX$^{2.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R$^3$ is a detectable moiety, a biomolecule, hydrogen, halogen, —CX$^{3.1}_3$, —CHX$^{3.1}_2$, —CH$_2$X$^{3.1}$, —CN, —SO$_{n1}$R$^{3A}$, —SO$_{v1}$NR$^{3B}$R$^{3C}$, —NHNR$^{3B}$R$^{3C}$, —ONR$^{3B}$R$^{3C}$, —NHC(O)NHNR$^{3B}$R$^{3C}$, —NHC(O)NR$^{3B}$R$^{3C}$, —N(O)$_{m1}$, —NR$^{3B}$R$^{3C}$, —C(O)R$^{3D}$, —C(O)OR$^{3D}$, —C(O)NR$^{3B}$R$^{3C}$, —OR$^{3A}$, —NR$^{3B}$SO$_2$R$^{3A}$, —NR$^{3B}$C(O)R$^{3D}$, —NR$^{3B}$C(O)OR$^{3D}$, —NR$^{3B}$OR$^{3D}$, —OCX$^{3.1}_3$, —OCHX$^{3.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R$^4$ is hydrogen or a ribose, wherein the ribose is part of a modified or unmodified RNA molecule, and further wherein the ribose comprises a guanine. R$^{1A}$, R$^{1B}$, R$^{1C}$, R$^{1D}$, R$^{2A}$, R$^{2B}$, R$^{2C}$, R$^{3D}$, R$^{3A}$, R$^{3B}$, R$^{3C}$ and R$^{3D}$ are independently hydrogen, halogen, —CF$_3$, —CCl$_3$, —CBr$_3$, —CI$_3$, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)—OH, —NHOH, —OCF$_3$, —OCCl$_3$, —OCBr$_3$, —OCI$_3$, —OCHF$_2$, —OCHCl$_2$, —OCHBr$_2$, —OCHI$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{1B}$, R$^{1C}$, R$^{2B}$, R$^{2C}$, R$^{3B}$ and R$^{3C}$ substituents bonded to the same nitrogen atom may optionally be joined to form a substituted or unsubstituted heterocycloalkyl or substituted or unsubstituted heteroaryl; and X$^{1.1}$, X$^{2.1}$ and X$^{3.1}$ are independently —Cl, —Br, —I or —F. The symbol n1 is 0, 1, 2, 3 or 4. The symbols m1 and v1 are independently 1 or 2.

Provided herein is a method of substituting a guanine with a PreQ1 analog within an RNA molecule. The method includes contacting a PreQ1 analog with an RNA molecule in the presence of a transglycosylase; and allowing the transglycosylase to substitute a guanine moiety from a guanine within the RNA sequence with the PreQ1 analog thereby forming a modified RNA molecule.

Also provided herein is a method of screening for a transglycosylase inhibitor. The method includes contacting a detectable PreQ1 with an RNA molecule in the presence of a transglycosylase and a test transglycosylase inhibitor; and determining whether the transglycosylase substitutes a guanine moiety from a guanine within the RNA molecule with the detectable PreQ1 analog.

BRIEF DESCRIPTION OF THE DRAWINGS

FIG. 1A: TGT catalyzed transglycosylation of ECY-A1 (SEQ ID NO:5) minihelix RNA with RNA including PreQ1 analog at position 8 (SEQ ID NO:7). FIG. 1B: Histogram depicting % labeled RNA. Bins (left to right): unmodified RNA; 5mC; pseudouridine; and 5mC+ pseudouridine.

FIG. 2A) HPLC Trace at 260 nm of ECY-A1 and ECY-A1 modified with PreQ$_1$-TO indicating covalent modification resulting in a shift of retention time. FIG. 2B) Fluorescence emission spectra of fluorogenic RNA labeling reaction with PreQ$_1$-TO. Fluorescence normalized to PreQ$_1$-TO in the absence of RNA and TGT enzyme. FIG. 2C) Biotin gel shift assay illustrating functional biotin covalently linked to ECY-A1. PreQ$_1$-Biotin modified samples were incubated with Streptavidin and analyzed on a 15% denaturing PAGE gel.

FIG. 3A) Fluorescent labeling of mCherry-TAG transcript with PreQ$_1$-BODIPY and PreQ$_1$-Cy7 visualized via 4% denaturing PAGE. FIG. 3B) Fluorescence emission spectra of fluorogenic labeling reaction with PreQ$_1$-TO. Fluorescence normalized to PreQ$_1$-TO with RNA in the absence of TGT Enzyme. FIG. 3C) PAGE analysis of streptavidin pull down assay. Transcript subjected to TGT reaction conditions with PreQ$_1$-Biotin was subsequently pulled down with streptavidin M-280 DYNABEADS®. Lanes representing recovered mCherry-TAG and mCherry-TAGΔC are shown.

FIG. 6A: Plot of estimated amount of PreQ$_1$-TO incorporated into ECY-A1 as a function of TGT reaction time progress. Data graphs are in order (top to bottom): 25.09 µM, 7.75 µM, 2.10 µM, 606.5 nM, 175.4 nM, and 50.72 nM. FIG. 6B: Plotted initial rates observed from A to determine enzyme reaction kinetic parameters k$_{cat}$ and k$_m$ for PreQ$_1$-TO with ECY-A1.

(FIG. 11A). Tetrazine labeling of PreQ1-linker. (FIG. 11B). Secondary labeling reaction through tetrazine moiety with a strained dienophile.

(FIG. 13A) PreQ1-thiazole orange (TO) and corresponding fluorescence emission intensity scan. (FIG. 13B) PreQ1-thiazole orange analogs and corresponding fluorescence emission intensity scans.

(FIG. 14A) PreQ1-C6-thiazole orange-N and PreQ1-PEG3-thiazole orange-methyl. (FIG. 13B) PreQ1-C6-thiazole orange-N fluorescence emission intensity scan. (FIG. 14B) PreQ1-PEG3-thiazole orange-methyl intensity scan.

(FIG. 15A) Schematic representation of a contruct of HDAC2 and mRNA hairpin. (FIG. 15 B) Schematic representation of RNA and RNA-protein pull down assay. (FIG. 15C) Graphic representation of qPCR results indicating labeling and pull down of RNA in pull down assay were quantitative.

(FIG. 18A) Demonstrates secondary labeling of tetrazine moiety can subsequently be used as an affinity ligand. (FIG. 18B) Shows affinity ligands for various applications.

FIGS. 19A-19B. (FIG. 19A) Shows schematic for screening of transglycosylase inhibitor. (FIG. 19B) Shows that fluorescence indicates a non-inhibitor of transglycosylase.

FIGS. 20A-20B. (FIG. 20A) Compares sequences of ECY-A1, ECY-A1 ΔC and ECY-X 1. (FIG. 20B). Demonstrates RNA substrate selectivity with transglycosylase-PreQ1-TO is selectively incorporated into ECY-A1.

DETAILED DESCRIPTION OF THE INVENTION

Definitions

Figure 1A:
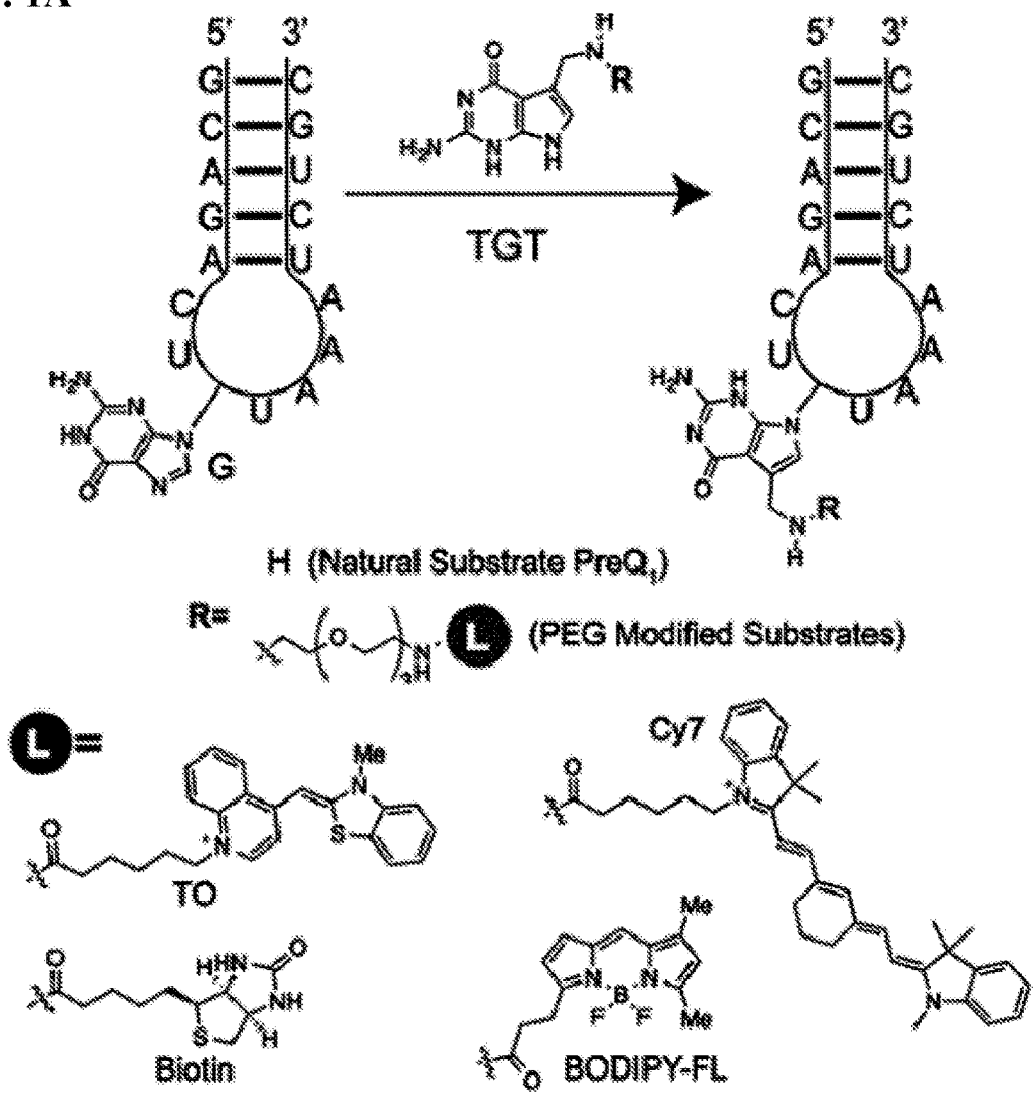
FIGS. 1A-1B.
Figure 1B:
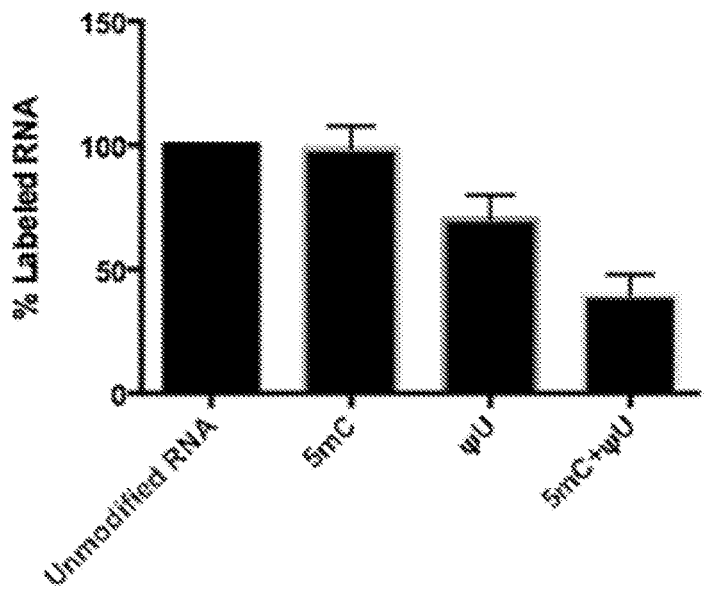

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —CH$_2$O— is equivalent to —OCH$_2$—.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include di- and multivalent radicals, having the number of carbon atoms designated (i.e., C$_1$-C$_{10}$ means one to ten carbons). Alkyl is not cyclized. Examples of saturated hydrocarbon radicals include, but are not limited to, groups such as methyl, ethyl, n-propyl, isopropyl, n-butyl, t-butyl, isobutyl, sec-butyl, (cyclohexyl) methyl, homologs and isomers of, for example, n-pentyl, n-hexyl, n-heptyl, n-octyl, and the like. An unsaturated alkyl group is one having one or more double bonds or triple bonds (e.g. alkene, alkyne). Examples of unsaturated alkyl groups include, but are not limited to, vinyl, 2-propenyl, crotyl, 2-isopentenyl, 2-(butadienyl), 2,4-pentadienyl, 3-(1, 4-pentadienyl), ethynyl, 1- and 3-propynyl, 3-butynyl, and the higher homologs and isomers. An alkoxy is an alkyl attached to the remainder of the molecule via an oxygen linker (—O—). An alkyl moiety may be an alkenyl moiety. An alkyl moiety may be an alkynyl moiety. An alkyl moiety may be fully saturated.

The term "alkylene," by itself or as part of another substituent, means, unless otherwise stated, a divalent radical derived from an alkyl, as exemplified, but not limited by, —CH$_2$CH$_2$CH$_2$CH$_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable straight or branched chain, or combinations thereof, including at least one carbon atom and at least one heteroatom selected from the group consisting of O, N, P, Si, and S, and wherein the nitrogen and sulfur atoms may optionally be oxidized, and the nitrogen heteroatom may optionally be quaternized. Heteroalkyl is not cyclized. The heteroatom(s) O, N, P, S, and Si may be placed at any interior position of the heteroalkyl group or at the position at which the alkyl group is attached to the remainder of the molecule. Examples include, but are not limited to: —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH═CH—O—CH$_3$, —Si(CH$_3$)$_3$, —CH$_2$—CH═N—OCH$_3$, —CH═CH—N(CH$_3$)—CH$_3$, —O—CH$_3$, —O—CH$_2$—CH$_3$, and —CN. Up to two or three heteroatoms may be consecutive, such as, for example, —CH$_2$—NH—OCH$_3$ and —CH$_2$—O—Si(CH$_3$)$_3$. A heteroalkyl moiety may include one heteroatom (e.g., O, N, S, Si, or P). A heteroalkyl moiety may include two optionally different heteroatoms (e.g., O, N, S, Si, or P). A heteroalkyl moiety may include three optionally different heteroatoms (e.g., O, N, S, Si, or P). A heteroalkyl moiety may include four optionally different heteroatoms (e.g., O, N, S, Si, or P). A heteroalkyl moiety may include five optionally different heteroatoms (e.g., O, N, S, Si, or P). A heteroalkyl moiety may include up to 8 optionally different heteroatoms (e.g., O, N, S, Si, or P).

Similarly, the term "heteroalkylene," by itself or as part of another substituent, means, unless otherwise stated, a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'—represents both —C(O)$_2$R'—and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, non-aromatic cyclic versions of "alkyl" and "heteroalkyl," respectively, wherein the carbons making up the ring or rings do not necessarily need to be bonded to a hydrogen due to all carbon valencies participating in bonds with non-hydrogen atoms. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, 3-hydroxy-cyclobut-3-enyl-1,2, dione, 1H-1,2,4-triazolyl—S(4H)-one, 4H-1,2,4-triazolyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively. A heterocycloalkyl moiety may include one ring heteroatom (e.g., O, N, S, Si, or P). A heterocycloalkyl moiety may include two optionally different ring heteroatoms (e.g., O, N, S, Si, or P). A heterocycloalkyl moiety may include three optionally different ring heteroatoms (e.g., O, N, S, Si, or P). A heterocycloalkyl moiety may include four optionally different ring heteroatoms (e.g., O, N, S, Si, or P). A heterocycloalkyl moiety may include five optionally different ring heteroatoms (e.g., O, N, S, Si, or P). A heterocycloalkyl moiety may include up to 8 optionally different ring heteroatoms (e.g., O, N, S, Si, or P).

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$) alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. Non-limiting examples of aryl and heteroaryl groups include pyridinyl, pyrimidinyl, thiophenyl, thienyl, furanyl, indolyl, benzoxadiazolyl, benzodioxolyl, benzodioxanyl, thianaphthanyl, pyrrolopyridinyl, indazolyl, quinolinyl, quinoxalinyl, pyridopyrazinyl, quinazolinonyl, benzoisoxazolyl, imidazopyridinyl, benzofuranyl, benzothienyl, benzothiophenyl, phenyl, naphthyl, biphenyl, pyrrolyl, pyrazolyl, imidazolyl, pyrazinyl, oxazolyl, isoxazolyl, thiazolyl, furylthienyl, pyridyl, pyrimidyl, benzothiazolyl, purinyl, benzimidazolyl, isoquinolyl, thiadiazolyl, oxadiazolyl, pyrrolyl, diazolyl, triazolyl, tetrazolyl, benzothiadiazolyl, isothiazolyl, pyrazolopyrimidinyl, pyrrolopyrimidinyl, benzotriazolyl, benzoxazolyl, or quinolyl. The examples above may be substituted or unsubstituted and divalent radicals of each heteroaryl example above are non-limiting examples of heteroarylene. A heteroaryl moiety may include one ring heteroatom (e.g., O, N, or S). A heteroaryl moiety may include two optionally different ring heteroatoms (e.g., O, N, or S). A heteroaryl moiety may include three optionally different ring heteroatoms (e.g., O, N, or S). A heteroaryl moiety may include four optionally different ring heteroatoms (e.g., O, N, or S). A heteroaryl moiety may include five optionally different ring heteroatoms (e.g., O, N, or S). An aryl moiety may have a single ring. An aryl moiety may have two optionally different rings. An aryl moiety may have three optionally different rings. An aryl moiety may have four optionally different rings. A heteroaryl moiety may have one ring. A heteroaryl moiety may have two optionally different rings. A heteroaryl moiety may have three optionally different rings. A heteroaryl moiety may have four optionally different rings. A heteroaryl moiety may have five optionally different rings.

A fused ring heterocyloalkyl-aryl is an aryl fused to a heterocycloalkyl. A fused ring heterocycloalkyl-heteroaryl is a heteroaryl fused to a heterocycloalkyl. A fused ring heterocycloalkyl-cycloalkyl is a heterocycloalkyl fused to a cycloalkyl. A fused ring heterocycloalkyl-heterocycloalkyl is a heterocycloalkyl fused to another heterocycloalkyl. Fused ring heterocycloalkyl-aryl, fused ring heterocycloalkyl-heteroaryl, fused ring heterocycloalkyl-cycloalkyl, or fused ring heterocycloalkyl-heterocycloalkyl may each independently be unsubstituted or substituted with one or more of the substituents described herein.

The term "oxo," as used herein, means an oxygen that is double bonded ("=O") to a carbon atom.

The term "alkylsulfonyl," as used herein, means a moiety having the formula —S(O$_2$)—R', where R' is a substituted or unsubstituted alkyl group as defined above. R' may have a specified number of carbons (e.g., "C$_1$-C$_4$ alkylsulfonyl").

Each of the above terms (e.g., "alkyl," "heteroalkyl,", "cycloalkyl", "heterocycloalkyl", "aryl," and "heteroaryl") includes both substituted and unsubstituted forms of the indicated radical.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR—C(O)NR"R'", —NR"C(O)$_2$R', —NR—C(O)NR'R")=NR'", —S(O)R', —S(O)$_2$R', —S(O)$_2$N(R)('R"—NRSO$_2$R'), —CN, and —NO$_2$ in a number ranging from zero to (2m'+1), where m' is the total number of carbon atoms in such radical. R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy, or thioalkoxy groups, or arylalkyl groups. When a compound of the invention includes more than one R group, for example, each of the R groups is independently selected as are each R', R", R'", and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: —OR', —NR'R", —SR', -halogen, —SiR'R"R'", —OC(O)R', —C(O)R', —CO$_2$R', —CONR'R", —OC(O)NR'R", —NR"C(O)R', —NW—C(O)NR"R'", NR"C(O)$_2$R', NRC(NR'R")=NR'", S(O)R', —S(O)$_2$R', —S(O)$_2$N(R')(R", —NRSO$_2$R'), —CN, —NO$_2$, —R', —N$_3$, —CH(Ph)$_2$, fluoro(C$_1$-C$_4$)alkoxy, and fluoro (C$_1$-C$_4$)alkyl, in a number ranging from zero to the total number of open valences on the aromatic ring system; and where R', R", R'", and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound of the invention includes more than one R group, for example, each of the R groups is independently selected as are each R', R", R'", and R"" groups when more than one of these groups is present.

Where a moiety is substituted with an R substituent, the group may be referred to as "R-substituted." Where a moiety group is R-substituted, the moiety is substituted with at least one R substituent and each R substituent is optionally different. For example, where a moiety herein is R$^{1A}$-substituted or unsubstituted alkyl, a plurality of R$^{1A}$ substituents may be attached to the alkyl moiety wherein each R$^{1A}$ substituent is optionally different. Where an R-substituted moiety is substituted with a plurality R substituents, each of the R-substituents may be differentiated herein using a prime symbol (') such as R', R", etc. For example, where a moiety is R$^{1A}$-substituted or unsubstituted alkyl, and the moiety is substituted with a plurality of R$^{1A}$ substituents, the plurality of R$^{1A}$ substituents may be differentiated as R$^{1A'}$, R$^{1A''}$, R$^{1A'''}$, etc. In some embodiments, the plurality of R substituents is 3. In some embodiments, the plurality of R substituents is 2.

In embodiments, a compound as described herein may include multiple instances of R$^1$, R$^2$, and/or other substituents and variables. In such embodiments, each variable may optional be different and be appropriately labeled to distinguish each group for greater clarity. For example, where each R$^{6A}$ is different, they may be referred to, for example, as R$^{6A.1}$, R$^{6A.2}$, R$^{6A.3}$, or R$^{6A.4}$, respectively, wherein the definition of R$^{6A}$ is assumed by R$^{6A.1}$, R$^{6A.2}$, R$^{6A.3}$, and/or R$^{6A.4}$. The variables used within a definition of R$^1$, R$^2$, and/or other variables that appear at multiple instances and are different may similarly be appropriately labeled to distinguish each group for greater clarity.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In embodiments, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$),—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R"R'")$_d$—, where variables s and d are independently integers of from 0 to 3, and X' is —O—, —NR'—, —S—, —S(O)—, —S(O)$_2$—, or —S(O)$_2$NR'—. The substituents R, R', R", and R'" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include, oxygen (O), nitrogen (N), sulfur (S), phosphorus (P), and silicon (Si).

A "substituent group," as used herein, means a group selected from the following moieties:

(A) oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O) NHNH$_2$, —NHC=(O) NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, heteroaryl, substituted with at least one substituent selected from:
  (i) oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and
  (ii) alkyl, heteroalkyl, cycloalkyl, heterocycloalkyl, aryl, heteroaryl, substituted with at least one substituent selected from:
    (a) oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and
(b) alkyl, heteroalkyl, cycloalkyl, heterocycloalkyl, aryl, heteroaryl, substituted with at least one substituent selected from: oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O) NHNH$_2$, —NHC=(O) NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl.

A "size-limited substituent" or " size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 10 membered heteroaryl.

A "lower substituent" or " lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 9 membered heteroaryl.

In embodiments, each substituted group described in the compounds herein is substituted with at least one substituent group. More specifically, In embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 10 membered heteroaryl. In embodiments herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene. In embodiments, the compound is a chemical species set forth in the Examples section below.

The term "pharmaceutically acceptable salts" is meant to include salts of the active compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge et al., *Journal of Pharmaceutical Science* 66:1-19 (1977)). Certain specific compounds of the present invention contain both basic and acidic functionalities that allow the compounds to be converted into either base or acid addition salts. Other pharmaceutically acceptable carriers known to those of skill in the art are suitable for the present invention. Salts tend to be more soluble in aqueous or other protonic solvents that are the corresponding free base forms. In other cases, the preparation may be a lyophilized powder in 1 mM-50 mM histidine, 0.1%-2% sucrose, 2%-7% mannitol at a pH range of 4.5 to 5.5, that is combined with buffer prior to use.

Thus, the compounds of the present invention may exist as salts, such as with pharmaceutically acceptable acids. The present invention includes such salts. Examples of such salts include hydrochlorides, hydrobromides, sulfates, methanesulfonates, nitrates, maleates, acetates, citrates, fumarates, tartrates (e.g., (+)-tartrates, (−)-tartrates, or mixtures thereof including racemic mixtures), succinates, benzoates, and salts with amino acids such as glutamic acid. These salts may be prepared by methods known to those skilled in the art.

The neutral forms of the compounds are preferably regenerated by contacting the salt with a base or acid and isolating the parent compound in the conventional manner. The parent form of the compound differs from the various salt forms in certain physical properties, such as solubility in polar solvents.

Provided herein are agents (e.g. compounds, drugs, therapeutic agents) that may be in a prodrug form. Prodrugs of the compounds described herein are those compounds that readily undergo chemical changes under select physiological conditions to provide the final agents (e.g. compounds, drugs, therapeutic agents). Additionally, prodrugs can be converted to agents (e.g. compounds, drugs, therapeutic agents) by chemical or biochemical methods in an ex vivo environment. Prodrugs described herein include compounds that readily undergo chemical changes under select physiological conditions to provide agents (e.g. compounds, drugs, therapeutic agents) to a biological system (e.g. in a subject, in a cell, in the extracellular space near a cell).

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

As used herein, the term "salt" refers to acid or base salts of the compounds used in the methods of the present invention. Illustrative examples of acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts.

Certain compounds of the present invention possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)-or (S)— or, as (D)- or (L)- for amino acids, and individual isomers are encompassed within the scope of the present invention. The compounds of the present invention do not include those which are known in art to be too unstable to synthesize and/or isolate. The present invention is meant to include compounds in racemic and optically pure forms. Optically active (R)— and (S)—, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of this invention.

The compounds of the present invention may also contain unnatural proportions of atomic isotopes at one or more of the atoms that constitute such compounds. For example, the compounds may be radiolabeled with radioactive isotopes, such as for example tritium ($^{3}H$), iodine-125 ($^{125}I$), or carbon-14 ($^{14}C$). All isotopic variations of the compounds of the present invention, whether radioactive or not, are encompassed within the scope of the present invention.

The symbol ⌇ denotes the point of attachment of a chemical moiety to the remainder of a molecule or chemical formula.

The terms "treating", or "treatment" refers to any indicia of success in the treatment or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. The term "treating" and conjugations thereof, include prevention of an injury, pathology, condition, or disease.

An "effective amount" is an amount sufficient for a compound to accomplish a stated purpose relative to the absence of the compound (e.g. achieve the effect for which it is administered, treat a disease, reduce enzyme activity, increase enzyme activity, reduce a signaling pathway, or reduce one or more symptoms of a disease or condition). An example of an "therapeutically effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

The term "associated" or "associated with" in the context of a substance or substance activity or function associated with a disease (e.g. infectious disease, hyperproliferative disease, cancer) means that the disease is caused by (in whole or in part), or a symptom of the disease is caused by (in whole or in part) the substance or substance activity or function. As used herein, what is described as being associated with a disease, if a causative agent, could be a target for treatment of the disease. For example, a disease associated with infection may be treated with an agent (e.g. compound as described herein) effective as an antibiotic.

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects. In some embodiments, a control is the measurement of the activity of a protein in the absence of a compound as described herein (including embodiments and examples).

As defined herein, the term "inhibition", "inhibit", "inhibiting" and the like in reference to a protein-inhibitor interaction means negatively affecting (e.g. decreasing) the activity or function of the protein relative to the activity or function of the protein in the absence of the inhibitor. In some embodiments inhibition refers to reduction of a disease or symptoms of disease. In some embodiments, inhibition refers to a reduction in the activity of a particular protein or nucleic acid target. Thus, inhibition includes, at least in part, partially or totally blocking stimulation, decreasing, preventing, or delaying activation, or inactivating, desensitizing, or down-regulating signal transduction or enzymatic activity or the amount of a protein.

"Contacting" is used in accordance with its plain ordinary meaning and refers to the process of allowing at least two distinct species (e.g. chemical compounds including biomolecules or cells) to become sufficiently proximal to react, interact or physically touch. It should be appreciated; however, the resulting reaction product can be produced directly from a reaction between the added reagents or from an intermediate from one or more of the added reagents which can be produced in the reaction mixture.

The term "contacting" may include allowing two species to react, interact, or physically touch, wherein the two species may be a compound as described herein and a protein or enzyme. In some embodiments contacting includes allowing a compound described herein to interact with a protein or enzyme that is involved in a signaling pathway.

As used herein, "biomolecule" is used in its customary sense and refers to a molecule found in nature or derivatives thereof, including macromolecules such as proteins, carbohydrates, lipids, and nucleic acids, as well as small molecules such as primary metabolites, secondary metabolites, and natural products. A biomolecule may be present as a moiety attached to the remainder of a compound. A biomolecule includes but is not limited to nucleic acids (e.g. DNA and RNA), peptide nucleic acids, sugars, peptides, proteins, antibodies, lipids, small molecule affinity ligands e.g. inhibitors, biotin and haptens.

The terms "transglycosylase," "TGT" or "tRNA guanine transglycosylase" are here used interchangeably and according to their common, ordinary meaning (e.g., bacterial tRNA guanine transglycosylase) and refer to proteins of the same or similar names and functional fragments and homologs thereof. A sequence for bacterial transglycosylase (TGT) is set forth in SEQ ID NO:8. An amino acid residue in a protein or receptor "corresponds" to a given residue when it occupies the same essential structural position within the protein or receptor as the given residue, for example, in homologous proteins that may have a different numbering convention. The term includes any recombinant or naturally occurring form of, or variants thereof, that maintain bacterial transglycosylase activity (e.g. within at least 50%, 60%, 70%, 80%, 90%, 95%, or 100% activity compared to bacterial transglycosylase). In embodiments, the bacterial transglycosylase has at least 50%, 60%, 70%, 80%, 85%, 90%, 95%, 96%, 97%, 98%, 99% or 100% sequence identity to SEQ ID NO:8 or a functional fragment thereof (e.g. 190 contiguous amino acids of SEQ ID NO:8, 220 contiguous amino acids of SEQ ID NO:8, 250 contiguous amino acids of SEQ ID NO:8, 300 contiguous amino acids of SEQ ID NO:8, 320 contiguous amino acids of SEQ ID NO:8, 340 contiguous amino acids of SEQ ID NO:8, 350 contiguous amino acids of SEQ ID NO:8, 360 contiguous amino acids of SEQ ID NO:8, 365 contiguous amino acids of SEQ ID NO:8, 370 contiguous amino acids of SEQ ID NO:8, 375 contiguous amino acids of SEQ ID NO:8 or 381 contiguous amino acids of SEQ ID NO:8).

The "catalytic domain," "catalytic site," "binding site" or "active site" of bacterial transglycosylase is a region within the transglycosylase where substrate molecules bind to and undergo a chemical transformation (e.g. substitution of a guanine within an RNA molecule with a PreQ1 analog). The active site includes residues that form temporary bonds with the "substrate."

A "substrate," as used herein may be a PreQ1 analog. The "substrate" or PreQ1 analog substitutes a guanine within a modified or unmodified RNA sequence. A modified RNA sequence may comprise any number of unnatural or synthetic nucleotides, including nucleotides that are chemically modified with a labeling molecule (e.g. a biomolecule or synthetic chemical molecule (e.g. a small molecule)). The substrate is specifically designed to bind to the transglycosylase and make contact with amino acids residing on the surface of the binding site of the transglycosylase. In embodiments, the substrate is a synthetic chemically derivatized PreQ1 molecule, according to the disclosure provided herein, to bind to the binding site of the transglycosylase. In embodiments, PreQ1 is chemically modified with synthetic chemical molecules that are small molecules (a low molecular weight (<900 daltons) organic compound). In embodiments, PreQ1 is chemically derivatized with a biomolecule. In embodiments, linkers are used to attach, or in the attachment of, the small molecules or biomolecules to PreQ1.

The term "PreQ1 analog" as used herein, refers to a queuine (Q) precursor analog and is an analog of a modified nucleobase that is derivatized or chemically modified at the nitrogen in the —CH$_2$NH$_2$— moiety of the nucleobase to form a secondary amine (e.g. —CH$_2$NHR—) where R is not hydrogen. PreQ1 analogs have the general structure:

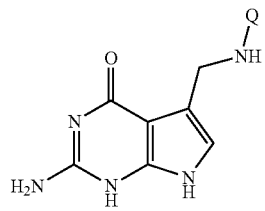

where Q is not hydrogen. In embodiments, Q is L$^1$-L$^2$-R$^3$.

The term "fluorophore" as used herein refers to a fluorescent chemical compound or moiety that can re-emit light upon light excitation. Fluorophores typically contain several combined aromatic groups, or planar or cyclic molecules with several π bonds.

The term "dienophile" as used herein refers to an alkene or alkyne that reacts with a conjugated diene in a cycloaddition reaction. As used herein, dienophiles may contain heteroatoms e.g. nitrogen. In some embodiments, the dienophiles are strained ring systems.

"Dye" is used in accordance with its plain ordinary meaning and refers to compounds or moieties that absorb light in the visible spectrum (400-700 nm), have at least one chromophore (color-bearing group), have a conjugated system of alternating double and single bonds and exhibit resonance of electrons e.g. xanthenes.

The term "linker" as described herein is a divalent chemical group that covalently joins one chemical moiety to another. Specific examples of linkers are described herein. Linkers may be polyethylene (PEG) linkers or bioconjugate linkers.

As used herein, the term "bioconjugate" or "bioconjugate linker" refers to the resulting association between atoms or molecules of bioconjugate reactive groups. The association can be direct or indirect. For example, a conjugate between a first bioconjugate reactive group (e.g., —NH$_2$, —COOH, —N-hydroxysuccinimide, or maleimide) and a second bioconjugate reactive group (e.g., sulfhydryl, sulfur-containing amino acid, amine, amine sidechain containing amino acid, or carboxylate) provided herein can be direct, e.g., by covalent bond or linker (e.g. a first linker of second linker), or indirect, e.g., by non-covalent bond (e.g. electrostatic interactions (e.g. ionic bond, hydrogen bond, halogen bond), van der Waals interactions (e.g. dipole-dipole, dipole-induced dipole, London dispersion), ring stacking (pi effects), hydrophobic interactions and the like). In embodiments, bioconjugates or bioconjugate linkers are formed using bioconjugate chemistry (i.e. the association of two bioconjugate reactive groups) including, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982. In embodiments, the first bioconjugate reactive group (e.g., maleimide moiety) is covalently attached to the second bioconjugate reactive group (e.g. a sulfhydryl). In embodiments, the first bioconjugate reactive group (e.g., haloacetyl moiety) is covalently attached to the second bioconjugate reactive group (e.g. a sulfhydryl). In embodiments, the first bioconjugate reactive group (e.g., pyridyl moiety) is covalently attached to the second bioconjugate reactive group (e.g. a sulfhydryl). In embodiments, the first bioconjugate reactive group (e.g., —N-hydroxysuccinimide moiety) is covalently attached to the second bioconjugate reactive group (e.g. an amine). In embodiments, the first bioconjugate reactive group (e.g., maleimide moiety) is covalently attached to the second bioconjugate reactive group (e.g. a sulfhydryl). In embodiments, the first bioconjugate reactive group (e.g., —sulfo-N-hydroxysuccinimide moiety) is covalently attached to the second bioconjugate reactive group (e.g. an amine).

Useful bioconjugate reactive groups used for bioconjugate chemistries herein include, for example:
(a) carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters;
(b) hydroxyl groups which can be converted to esters, ethers, aldehydes, etc.
(c) haloalkyl groups wherein the halide can be later displaced with a nucleophilic group such as, for example, an amine, a carboxylate anion, thiol anion, carbanion, or an alkoxide ion, thereby resulting in the covalent attachment of a new group at the site of the halogen atom;
(d) dienophile groups which are capable of participating in Diels-Alder reactions such as, for example, maleimido or maleimide groups;
(e) aldehyde or ketone groups such that subsequent derivatization is possible via formation of carbonyl derivatives such as, for example, imines, hydrazones, semicarbazones or oximes, or via such mechanisms as Grignard addition or alkyllithium addition;

(f) sulfonyl halide groups for subsequent reaction with amines, for example, to form sulfonamides;

(g) thiol groups, which can be converted to disulfides, reacted with acyl halides, or bonded to metals such as gold, or react with maleimides;

(h) amine or sulfhydryl groups (e.g., present in cysteine), which can be, for example, acylated, alkylated or oxidized;

(i) alkenes, which can undergo, for example, cycloadditions, acylation, Michael addition, etc;

(j) epoxides, which can react with, for example, amines and hydroxyl compounds;

(k) phosphoramidites and other standard functional groups useful in nucleic acid synthesis;

(l) metal silicon oxide bonding; and (m) metal bonding to reactive phosphorus groups (e.g. phosphines) to form, for example, phosphate diester bonds.

(n) azides coupled to alkynes using copper catalyzed cycloaddition click chemistry.

(o) biotin conjugate can react with avidin or strepavidin to form a avidin-biotin complex or streptavidin-biotin complex.

The bioconjugate reactive groups can be chosen such that they do not participate in, or interfere with, the chemical stability of the conjugate described herein. Alternatively, a reactive functional group can be protected from participating in the crosslinking reaction by the presence of a protecting group. In embodiments, the bioconjugate comprises a molecular entity derived from the reaction of an unsaturated bond, such as a maleimide, and a sulfhydryl group.

A "cell" as used herein, refers to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaroytic cells. Prokaryotic cells include but are not limited to bacteria. Eukaryotic cells include but are not limited to yeast cells and cells derived from plants and animals, for example mammalian, insect (e.g., spodoptera) and human cells. Cells may be useful when they are naturally nonadherent or have been treated not to adhere to surfaces, for example by trypsinization.

"Patient," "subject," "patient in need thereof," and "subject in need thereof" are herein used interchangeably and refer to a living organism suffering from or prone to a disease or condition that can be treated by administration of a pharmaceutical composition as provided herein. Non-limiting examples include humans, other mammals, bovines, rats, mice, dogs, monkeys, goat, sheep, cows, deer, and other non-mammalian animals. In some embodiments, a patient is human.

"Disease" or "condition" refer to a state of being or health status of a patient or subject capable of being treated with the compounds or methods provided herein.

As used herein, the term "infectious disease" refers to a disease or condition related to the presence of an organism (the agent or infectious agent) within or contacting the subject or patient. Examples include a bacterium, fungus, virus, or other microorganism. A "bacterial infectious disease" is an infectious disease wherein the organism is a bacterium.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

As used herein, the term "administering" means oral administration, administration as a suppository, topical contact, intravenous, parenteral, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc.

By "co-administer" it is meant that a composition described herein is administered at the same time, just prior to, or just after the administration of one or more additional therapies. The compound of the invention can be administered alone or can be co-administered to the patient. Co-administration is meant to include simultaneous or sequential administration of the compound individually or in combination (more than one compound or agent). Thus, the preparations can also be combined, when desired, with other active substances (e.g. to reduce metabolic degradation).

The compositions disclosed herein can be delivered by transdermally, by a topical route, formulated as applicator sticks, solutions, suspensions, emulsions, gels, creams, ointments, pastes, jellies, paints, powders, and aerosols. Oral preparations include tablets, pills, powder, dragees, capsules, liquids, lozenges, cachets, gels, syrups, slurries, suspensions, etc., suitable for ingestion by the patient. Solid form preparations include powders, tablets, pills, capsules, cachets, suppositories, and dispersible granules. Liquid form preparations include solutions, suspensions, and emulsions, for example, water or water/propylene glycol solutions. The compositions of the present invention may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760.

The entire contents of these patents are incorporated herein by reference in their entirety for all purposes. The compositions disclosed herein can also be delivered as microspheres for slow release in the body. For example, microspheres can be administered via intradermal injection of drug-containing microspheres, which slowly release subcutaneously (see Rao, *J. Biomater Sci. Polym. Ed.* 7:623-645, 1995; as biodegradable and injectable gel formulations (see, e.g., Gao *Pharm. Res.* 12:857-863, 1995); or, as microspheres for oral administration (see, e.g., Eyles, *J. Pharm. Pharmacol.* 49:669-674, 1997). In another embodiment, the formulations of the compositions of the present invention can be delivered by the use of liposomes which fuse with the cellular membrane or are endocytosed, i.e., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions of the present invention into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989). The compositions can also be delivered as nanoparticles.

Pharmaceutical compositions may include compositions wherein the active ingredient (e.g. compounds described herein, including embodiments or examples) is contained in a therapeutically effective amount, i.e., in an amount effective to achieve its intended purpose. The actual amount effective for a particular application will depend, inter alia, on the condition being treated. When administered in methods to treat a disease, such compositions will contain an amount of active ingredient effective to achieve the desired result, e.g., modulating the activity of a target molecule, and/or reducing, eliminating, or slowing the progression of disease symptoms.

The dosage and frequency (single or multiple doses) administered to a mammal can vary depending upon a variety of factors, for example, whether the mammal suffers from another disease, and its route of administration; size, age, sex, health, body weight, body mass index, and diet of the recipient; nature and extent of symptoms of the disease being treated, kind of concurrent treatment, complications from the disease being treated or other health-related problems. Other therapeutic regimens or agents can be used in conjunction with the methods and compounds of Applicants' invention. Adjustment and manipulation of established dosages (e.g., frequency and duration) are well within the ability of those skilled in the art.

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the compound being employed. The dose administered to a patient, in the context of the present invention should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. Dosage amounts and intervals can be adjusted individually to provide levels of the administered compound effective for the particular clinical indication being treated. This will provide a therapeutic regimen that is commensurate with the severity of the individual's disease state.

The term "associated" or "associated with" in the context of a substance or substance activity or function associated with a disease means that the disease is caused by or otherwise characterized by (in whole or in part), a symptom of the disease is caused by (in whole or in part) the substance or substance activity or function, or a side-effect of the compound (e.g. toxicity) is caused by or characterized by (in whole or in part) the substance or substance activity or function.

An "agonist," as used herein, refers to a compound capable of detectably increasing the expression or activity of a given protein or receptor. The agonist can increase expression or activity 10%, 20%, 30%, 40%, 50%, 60%, 70%, 80%, 90%, 100% or more in comparison to a control in the absence of the agonist. In embodiments, expression or activity is 1.5-fold, 2-fold, 3-fold, 4-fold, 5-fold, 10-fold or more higher than the expression or activity in the absence of the agonist.

The term "antagonist" refers to a substance capable of detectably lowering expression or activity of a given protein. The antagonist can inhibit expression or activity 10%, 20%, 30%, 40%, 50%, 60%, 70%, 80%, 90%, 100% or less in comparison to a control in the absence of the antagonist. In embodiments, the inhibition is 1.5-fold, 2-fold, 3-fold, 4-fold, 5-fold, 10-fold, or more than the expression or activity in the absence of the antagonist.

The term "nucleic acid" refers to deoxyribonucleotides or ribonucleotides and polymers thereof in either single-, double- or multiple-stranded form, or complements thereof. The term "polynucleotide" refers to a linear sequence of nucleotides. The term "nucleotide" typically refers to a single unit of a polynucleotide, i.e., a monomer. Nucleotides can be ribonucleotides, deoxyribonucleotides, or modified versions thereof. Examples of polynucleotides contemplated herein include single and double stranded DNA, single and double stranded RNA (including siRNA), and hybrid molecules having mixtures of single and double stranded DNA and RNA. Nucleic acids can be linear or branched. For example, nucleic acids can be a linear chain of nucleotides or the nucleic acids can be branched, e.g., such that the nucleic acids comprise one or more arms or branches of nucleotides. Optionally, the branched nucleic acids are repetitively branched to form higher ordered structures such as dendrimers and the like.

Nucleic acids, including nucleic acids with a phosphothioate backbone can include one or more reactive moieties. As used herein, the term reactive moiety includes any group capable of reacting with another molecule, e.g., a nucleic acid or polypeptide through covalent, non-covalent or other interactions. By way of example, the nucleic acid can include an amino acid reactive moiety that reacts with an amio acid on a protein or polypeptide through a covalent, non-covalent or other interaction.

The terms also encompass nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphodiester derivatives including, e.g., phosphoramidate, phosphorodiamidate, phosphorothioate (also known as phosphothioate), phosphorodithioate, phosphonocarboxylic acids, phosphonocarboxylates, phosphonoacetic acid, phosphonoformic acid, methyl phosphonate, boron phosphonate, or O-methylphosphoroamidite linkages (see Eckstein, OLIGO-NUCLEOTIDES AND ANALOGUES: A PRACTICAL APPROACH, Oxford University Press); and peptide nucleic acid backbones and linkages. Other analog nucleic acids include those with positive backbones; non-ionic backbones, modified sugars, and non-ribose backbones (e.g. phosphorodiamidate morpholino oligos or locked nucleic acids (LNA)), including those described in U.S. Pat. Nos. 5,235,033 and 5,034,506, and Chapters 6 and 7, ASC Symposium Series 580, *Carbohydrate Modifications in Antisense Research*, Sanghui & Cook, eds. Nucleic acids containing one or more carbocyclic sugars are also included within one definition of nucleic acids. Modifications of the ribose-phosphate backbone may be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs may be made. In embodiments, the internucleotide linkages in DNA are phosphodiester, phosphodiester derivatives, or a combination of both.

A "labeled nucleic acid or oligonucleotide" is one that is bound, either covalently, through a linker or a chemical bond, or noncovalently, through ionic, van der Waals, electrostatic, or hydrogen bonds to a label such that the presence of the nucleic acid may be detected by detecting the presence of the detectable label bound to the nucleic acid. Alternatively, a method using high affinity interactions may achieve the same results where one of a pair of binding partners binds to the other, e.g., biotin, streptavidin. In embodiments, the phosphorothioate nucleic acid or phosphorothioate polymer includes a detectable label, as disclosed herein and generally known in the art.

The word "expression" or "expressed" as used herein in reference to a gene means the transcriptional and/or translational product of that gene. The level of expression of a DNA molecule in a cell may be determined on the basis of either the amount of corresponding mRNA that is present within the cell or the amount of protein encoded by that DNA produced by the cell. The level of expression of non-coding nucleic acid molecules (e.g., siRNA) may be detected by standard PCR or Northern blot methods well known in the art. See, Sambrook et al., 1989 *Molecular Cloning: A Laboratory Manual,* 18.1-18.88.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all. Transgenic cells and plants are those that express a heterologous gene or coding sequence, typically as a result of recombinant methods.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls. Moreover, where a moiety is substituted with an R substituent, the group may be referred to as "R-substituted." Where a moiety is R-substituted, the moiety is substituted with at least one R substituent and each R substituent is optionally different.

Descriptions of compounds of the present invention are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

I. Compounds

Provided herein are compounds of structural Formula (II):

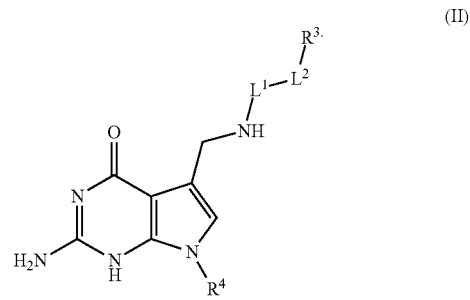

(II)

$L^1$ is a bond, substituted or unsubstituted alkylene or substituted or unsubstituted heteroalkylene, a detectable moiety, hydrogen, halogen, —$CX^{1.1}_3$, —$CHX^{1.1}_2$, —$CH_2X^{1.1}$, —CN, —$SO_{n1}R^{1A}$, —$SO_{v1}NR^{1B}R^{1C}$, —$NHNR^{1B}R^{1C}$, —$ONR^{1B}R^{1C}$, —$NHC(O)NHNR^{1B}R^{1C}$, —$NHC(O)NR^{1B}R^{1C}$, —$N(O)_{m1}$, —$NR^{1B}R^{1C}$, —$C(O)R^{1D}$, —$C(O)OR^{1D}$, —$C(O)NR^{1B}R^{1C}$, —$OR^{1A}$, —$NR^{1B}SO_2R^{1A}$, —$NR^{1B}C(O)R^{1D}$, —$NR^{1B}C(O)OR^{1D}$, —$NR^{1B}OR^{1D}$, —$OCX^{1.1}_3$, —$OCHX^{1.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$L^2$ is a bond, substituted or unsubstituted alkylene or substituted or unsubstituted heteroalkylene, a detectable moiety, hydrogen, halogen, —CX$^{2.1}_3$, —CHX$^{2.1}_2$, —CH$_2$X$^{2.1}$, —CN, —SO$_{n1}$R$^{2A}$, —SO$_{v1}$NR$^{2B}$R$^{2C}$, —NHNR$^{2B}$R$^{2C}$, —ONR$^{2B}$R$^{2C}$, —NHC(O)NHNR$^{2B}$R$^{2C}$, —NHC(O)NR$^{2B}$R$^{2C}$, —N(O)$_{m1}$, —NR$^{2B}$R$^{2C}$, —C(O)R$^{2D}$, —C(O)OR$^{2D}$, —C(O)NR$^{2B}$R$^{2C}$, —OR$^{2A}$, —NR$^{2B}$SO$_2$R$^{2A}$, —NR$^{2B}$C(O)R$^{2D}$, —NR$^{2B}$C(O)OR$^{2D}$, —NR$^{2B}$OR$^{2D}$, —OCX$^{2.1}_3$, —OCHX$^{2.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

R$^3$ is a detectable moiety, a biomolecule, hydrogen, halogen, —CX$^{3.1}_3$, —CHX$^{3.1}_2$, —CH$_2$X$^{3.1}$, —CN, —SO$_{n1}$R$^{3A}$, —SO$_{v1}$NR$^{3B}$R$^{3C}$, —NHNR$^{3B}$R$^{3C}$, —ONR$^{3B}$R$^{3C}$, —NHC(O)NHNR$^{3B}$R$^{3C}$, —NHC(O)NR$^{3B}$R$^{3C}$, —N(O)$_{m1}$, —NR$^{3B}$R$^{3C}$, —C(O)R$^{3D}$, —C(O)OR$^{3D}$, —C(O)NR$^{3B}$R$^{3C}$, —OR$^{3A}$, —NR$^{3B}$SO$_2$R$^{3A}$, —NR$^{3B}$C(O)R$^{3D}$, —NR$^{3B}$C(O)OR$^{3D}$, —NR$^{3B}$OR$^{3D}$, —OCX$^{3.1}_3$, —OCHX$^{3.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

R$^{1A}$,R$^{1B}$,R$^{1C}$, R$^{1D}$, R$^{2A}$,R$^{2B}$, R$^{2C}$, R$^{3D}$R$^{3A}$,R$^{3B}$, R$^{3C}$ and R$^{3D}$ are independently hydrogen, halogen, —CF$_3$, —CCl$_3$, —CBr$_3$, —CI$_3$, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)—OH, —NHOH, —OCF$_3$, —OCCl$_3$, —OCBr$_3$, —OCI$_3$, —OCHF$_2$, —OCHCl$_2$, —OCHBr$_2$, —OCHI$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, R$^{1B}$, R$^{1C}$, R$^{2B}$, R$^{2C}$, R$^{3B}$ and R$^{3C}$ substituents bonded to the same nitrogen atom may optionally be joined to form a substituted or unsubstituted heterocycloalkyl or substituted or unsubstituted heteroaryl.

X$^{1.1}$, X$^{2.1}$ and X$^{3.1}$ are independently —Cl, —Br, —I or —F. The symbol n1 is 0, 1, 2, 3 or 4. The symbols m1 and v1 are independently 1 or 2.

R$^4$ is hydrogen or a ribose, wherein the ribose may be part of a modified or unmodified RNA molecule, and further wherein the ribose comprises a guanine. In embodiments, R$^4$ is hydrogen. In embodiments, R$^4$ is hydrogen is a ribose. In embodiments, the RNA molecule comprises a hairpin element. In embodiments, the RNA molecule comprises a plurality of hairpin elements. In embodiments, the RNA molecule comprises modified nucleobase. In embodiments, the RNA molecule comprises a sequence as set forth in SEQ ID NO:5 or SEQ ID NO:6. In embodiments, the guanine is within a hairpin loop in the RNA molecule. In embodiments, the guanine forms part of a 5' YGU 3' sequence or a 5' UGY 3' sequence within the RNA molecule, where Y is a nucleotide or pseudouridine. In embodiments, the guanine is in a 5' UGU 3' sequence a 5' YGY 3' sequence, a 5' YGU 3' sequence or a 5' UGY 3' sequence within the RNA molecule, wherein Y is a nucleotide or pseudouridine. In embodiments, the guanine forms part of a 5' UGU 3' within the RNA molecule. In embodiments, the 5' UGU 3' sequence is within an RNA hairpin element. In embodiments, the 5' UGU 3' sequence is located in the loop of the hairpin. In embodiments, the guanine forms part of a 5' ψGψ 3' sequence within the RNA molecule. In embodiments, the RNA molecule comprises a 5-methylcytosine, a pseudouridine (ψ), a 2-thiouridine or any combination thereof. In embodiments, R$^4$ is hydrogen.

In embodiments, the compound has Formula (IIa):

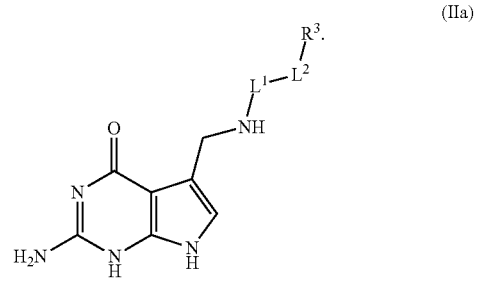

(IIa)

n1, m1, v1, L$^1$, L$^2$ and R$^3$ are as described herein.

In embodiments, L$^1$ is substituted or unsubstituted unbranched alkylene or substituted or unsubstituted unbranched heteroalkylene. In embodiments, L$^1$ is substituted or unsubstituted unbranched C$_4$-C$_{12}$ alkylene.

In embodiments, L$^1$ is a bond, —CX$^{1.1}_3$, —CHX$^{1.1}_2$, —CH$_2$X$^{1.1}$, —CN, —SO$_{n1}$R$^{1A}$, —SO$_{v1}$NR$^{1B}$R$^{1C}$, —NHNR$^{1B}$R$^{1C}$, —ONR$^{1B}$R$^{1C}$, —NHC(O)NHNR$^{1B}$R$^{1C}$, —NHC(O)NR$^{1B}$R$^{1C}$, —N(O)$_{m1}$, —NR$^{1B}$R$^{1C}$, —C(O)R$^{1D}$, —C(O)OR$^{1D}$, —C(O)NR$^{1B}$R$^{1C}$, —OR$^{1A}$, —NR$^{1B}$SO$_2$R$^{1A}$, —NR$^{1B}$C(O)R$^{1D}$, —NR$^{1B}$C(O)OR$^{1D}$, —NR$^{1B}$OR$^{1D}$, —OCX$^{1.1}_3$, —OCHX$^{1.1}_2$, substituted or unsubstituted alkylene or substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, L$^1$ is a bond.

In embodiments, L$^1$ is substituted or unsubstituted alkylene (e.g. C$_1$-C$_{18}$ alkylene, C$_1$-C$_{16}$ alkylene, C$_1$-C$_{14}$ alkylene, C$_1$-C$_{10}$ alkylene, C$_1$-C$_8$ alkylene, C$_1$-C$_6$ alkylene, or C$_1$-C$_4$ alkylene), substituted or unsubstituted heteroalkylene (e.g. 2 to 20 membered heteroalkylene, 2 to 18 membered heteroalkylene, 4 to 18 membered heteroalkylene, 2 to 16 membered heteroalkylene, 2 to 14 membered heteroalkylene, 2 to 10 membered heteroalkylene, 2 to 8 membered heteroalkylene, 4 to 8 membered heteroalkylene, 2 to 6 membered heteroalkylene, or 2 to 4 membered heteroalkylene), substituted or unsubstituted cycloalkylene (e.g. C$_3$-C$_8$ cycloalkylene, C$_4$-C$_8$ cycloalkylene, or C$_5$-C$_6$ cycloalkylene), substituted or unsubstituted heterocycloalkylene (e.g. 3 to 8 membered heterocycloalkylene, 4 to 8 membered heterocycloalkylene, or 5 to 6 membered heterocycloalkylene), substituted or unsubstituted arylene (e.g. C$_6$-C$_{10}$ arylene or C$_6$ arylene), or substituted or unsubstituted heteroarylene (e.g. 5 to 10 membered heteroarylene, 5 to 9 membered heteroarylene, or 5 to 6 membered heteroarylene).

In embodiments, L$^1$ is substituted or unsubstituted alkylene (e.g. C$_1$-C$_{18}$ alkylene, C$_1$-C$_{16}$ alkylene, C$_1$-C$_{14}$ alkylene, C$_1$-C$_{10}$ alkylene, C$_1$-C$_8$ alkylene, C$_1$-C$_6$ alkylene, or C$_1$-C$_4$ alkylene). In embodiments, L$^1$ is substituted or unsubstituted C$_1$-C$_8$ alkylene. In embodiments, L$^1$ is substituted C$_1$-C$_8$ alkylene. In embodiments, L$^1$ is R$^5$-substituted C$_1$-C$_8$ alkylene. In embodiments, L$^1$ is unsubstituted C$_1$-C$_8$ alkylene. In embodiments, L$^1$ is substituted or unsubstituted C$_8$ alkylene. In embodiments, L$^1$ is substituted C$_8$ alkylene. In embodiments, L$^1$ is R$^5$-substituted C$_8$ alkylene. In embodiments, L$^1$ is unsubstituted C$_8$ alkylene. In embodiments, L$^1$ is substituted or unsubstituted C$_6$ alkylene. In embodiments, L$^1$ is substituted C$_6$ alkylene. In embodiments, L$^1$ is R$^5$-substituted C$_6$ alkylene. In embodiments, L$^1$ is unsubstituted C$_6$ alkylene.

In embodiments, L¹ is substituted or unsubstituted heteroalkylene (e.g. 2 to 20 membered heteroalkylene, 2 to 18 membered heteroalkylene, 4 to 18 membered heteroalkylene, 2 to 16 membered heteroalkylene, 2 to 14 membered heteroalkylene, 2 to 10 membered heteroalkylene, 2 to 8 membered heteroalkylene, 4 to 8 membered heteroalkylene, 2 to 6 membered heteroalkylene, or 2 to 4 membered heteroalkylene). In embodiments, L¹ is substituted or unsubstituted 2 to 20 membered heteroalkylene. In embodiments, L¹ is substituted 2 to 20 membered heteroalkylene. In embodiments, L¹ is R⁵-substituted 2 to 20 membered heteroalkylene. In embodiments, L¹ is unsubstituted 2 to 20 membered heteroalkylene. In embodiments, L¹ is substituted 20 membered heteroalkylene. In embodiments, L¹ is R⁵-substituted 20 membered heteroalkylene. In embodiments, L¹ is unsubstituted 20 membered heteroalkylene. In embodiments, L¹ is substituted 19 membered heteroalkylene. In embodiments, L¹ is R⁵-substituted 19 membered heteroalkylene. In embodiments, L¹ is unsubstituted 19 membered heteroalkylene. In embodiments, L¹ is substituted 18 membered heteroalkylene. In embodiments, L¹ is R⁵-substituted 18 membered heteroalkylene. In embodiments, L¹ is unsubstituted 18 membered heteroalkylene. In embodiments, L¹ is substituted 17 membered heteroalkylene. In embodiments, L¹ is R⁵-substituted 17 membered heteroalkylene. In embodiments, L¹ is unsubstituted 17 membered heteroalkylene. In embodiments, L¹ is substituted 16 membered heteroalkylene. In embodiments, L¹ is R⁵-substituted 16 membered heteroalkylene. In embodiments, L¹ is unsubstituted 16 membered heteroalkylene.

In embodiments, L¹ is substituted or unsubstituted 2 to 10 membered heteroalkylene. In embodiments, L¹ is substituted 2 to 10 membered heteroalkylene. In embodiments, L¹ is R⁵-substituted 2 to 10 membered heteroalkylene. In embodiments, L¹ is unsubstituted 2 to 10 membered heteroalkylene. In embodiments, L¹ is substituted 10 membered heteroalkylene. In embodiments, L¹ is R⁵-substituted 10 membered heteroalkylene. In embodiments, L¹ is unsubstituted 10 membered heteroalkylene. In embodiments, L¹ is substituted 9 membered heteroalkylene. In embodiments, L¹ is R⁵-substituted 9 membered heteroalkylene. In embodiments, L¹ is unsubstituted 9 membered heteroalkylene. In embodiments, L¹ is substituted 8 membered heteroalkylene. In embodiments, L¹ is R⁵-substituted 8 membered heteroalkylene. In embodiments, L¹ is unsubstituted 8 membered heteroalkylene. In embodiments, L¹ is substituted 7 membered heteroalkylene. In embodiments, L¹ is R⁵-substituted 7 membered heteroalkylene. In embodiments, L¹ is unsubstituted 7 membered heteroalkylene. In embodiments, L¹ is substituted 6 membered heteroalkylene. In embodiments, L¹ is R⁵-substituted 6 membered heteroalkylene. In embodiments, L¹ is unsubstituted 6 membered heteroalkylene.

In embodiments, L¹ is R⁵-substituted or unsubstituted alkylene (e.g. C₁-C₈ alkylene, C₁-C₆ alkylene, or C₁-C₄ alkylene), R⁵-substituted or unsubstituted heteroalkylene (e.g. 2 to 10 membered heteroalkylene, 2 to 8 membered heteroalkylene, 4 to 8 membered heteroalkylene, 2 to 6 membered heteroalkylene, or 2 to 4 membered heteroalkylene), R⁵-substituted or unsubstituted cycloalkylene (e.g. C₃-C₈ cycloalkylene, C₄-C₈ cycloalkylene, or C₅-C₆ cycloalkylene), R⁵-substituted or unsubstituted heterocycloalkylene (e.g. 3 to 8 membered heterocycloalkylene, 4 to 8 membered heterocycloalkylene, or 5 to 6 membered heterocycloalkylene), R⁵-substituted or unsubstituted arylene (e.g. C₆-C₁₀ arylene or C₆ arylene), or R⁵-substituted or unsubstituted heteroarylene (e.g. 5 to 10 membered heteroarylene, 5 to 9 membered heteroarylene, or 5 to 6 membered heteroarylene).

R⁵ is independently oxo, halogen, —CF₃, —CN, —OH, —NH₂, —COOH, —CONH₂, —NO₂, —SH, —SO₃H, —SO₄H, —SO₂NH₂, —NHNH₂, —ONH₂, —NHC═(O) NHNH₂, —NHC═(O) NH₂, —NHSO₂H, —NHC═(O)H, —NHC(O)—OH, —NHOH, —OCF₃, —OCHF₂, R⁶-substituted or unsubstituted alkyl (e.g. C₁-C₈ alkyl, C₁-C₆ alkyl, or C₁-C₄ alkyl), R⁶-substituted or unsubstituted heteroalkyl (e.g. 2 to 8 membered heteroalkyl, 2 to 6 membered heteroalkyl, or 2 to 4 membered heteroalkyl), R⁶-substituted or unsubstituted cycloalkyl (e.g. C₃-C₈ cycloalkyl, C₄-C₈ cycloalkyl, or C₅-C₆ cycloalkyl), R⁶-substituted or unsubstituted heterocycloalkyl (e.g. 3 to 8 membered heterocycloalkyl, 4 to 8 membered heterocycloalkyl, or 5 to 6 membered heterocycloalkyl), R⁶-substituted or unsubstituted aryl (e.g. C₆-C₁₀ aryl or C₆ aryl), or R⁶-substituted or unsubstituted heteroaryl (e.g. 5 to 10 membered heteroaryl, 5 to 9 membered heteroaryl, or 5 to 6 membered heteroaryl).

In embodiments, R⁵ is substituted napthyl. In embodiments, R⁵ is R⁶-substituted napthyl. In embodiments, R⁵ is unsubstituted napthyl. In embodiments, R⁵ is substituted isoquinoline. In embodiments, R⁵ is R⁶-substituted isoquinoline. In embodiments, R⁵ is unsubstituted isoquinoline. In embodiments, R⁵ is substituted quinoline. In embodiments, R⁵ is R⁶-substituted quinoline. In embodiments, R⁵ is unsubstituted quinoline. In embodiments, R⁵ is substituted tetrazine. In embodiments, R⁵ is R⁶-substituted tetrazine. In embodiments, R⁵ is unsubstituted tetrazine.

In embodiments, R⁵ is

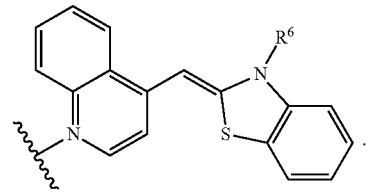

In embodiments, R⁵ is

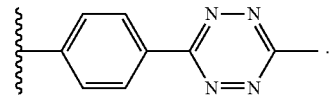

In embodiments, R⁵ is

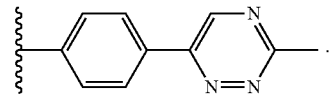

In embodiments, R⁵ is

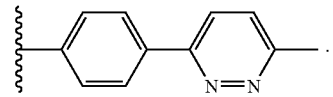

$R^6$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O) $NHNH_2$, —NHC=(O) $NH_2$, —$NHSO_2H$, —NHC=(O)H, —NHC(O)—OH, —NHOH, —$OCF_3$, —$OCHF_2$, $R^7$-substituted or unsubstituted alkyl (e.g. $C_1$-$C_8$ alkyl, $C_1$-$C_6$ alkyl, or $C_1$-$C_4$ alkyl), $R^7$-substituted or unsubstituted heteroalkyl (e.g. 2 to 8 membered heteroalkyl, 2 to 6 membered heteroalkyl, or 2 to 4 membered heteroalkyl), $R^7$-substituted or unsubstituted cycloalkyl (e.g. $C_3$-$C_8$ cycloalkyl, $C_4$-$C_8$ cycloalkyl, or $C_5$-$C_6$ cycloalkyl), $R^7$-substituted or unsubstituted heterocycloalkyl (e.g. 3 to 8 membered heterocycloalkyl, 4 to 8 membered heterocycloalkyl, or 5 to 6 membered heterocycloalkyl), $R^7$-substituted or unsubstituted aryl (e.g. $C_6$-$C_{10}$ aryl or $C_6$ aryl), or $R^7$-substituted or unsubstituted heteroaryl (e.g. 5 to 10 membered heteroaryl, 5 to 9 membered heteroaryl, or 5 to 6 membered heteroaryl).

In embodiments, $R^6$ is substituted napthyl. In embodiments, $R^6$ is $R^7$-substituted napthyl. In embodiments, $R^6$ is unsubstituted napthyl. In embodiments, $R^6$ is substituted isoquinoline. In embodiments, $R^6$ is $R^7$-substituted isoquinoline. In embodiments, $R^6$ is unsubstituted isoquinoline. In embodiments, $R^6$ is substituted quinoline. In embodiments, $R^6$ is $R^7$-substituted quinoline. In embodiments, $R^6$ is unsubstituted quinoline. In embodiments, $R^6$ is substituted tetrazine. In embodiments, $R^6$ is $R^7$-substituted tetrazine. In embodiments, $R^6$ is unsubstituted tetrazine.

In embodiments, $R^6$ is

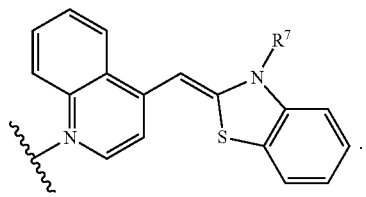

In embodiments, $R^6$ is

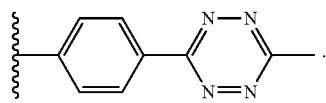

In embodiments, $R^6$ is

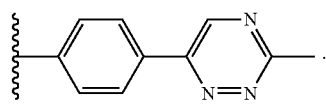

In embodiments, $R^6$ is

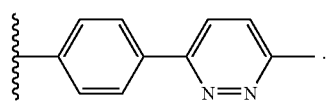

In embodiments, $L^2$ is a bond, a detectable moiety, halogen, —$CX^{2.1}_3$, —$CHX^{2.1}_2$, —$CH_2X^{2.1}$, —CN, —$SO_{n1}R^{2A}$, —$SO_{v1}NR^{2B}R^{2C}$, —$NHNR^{2B}R^{2C}$, —$ONR^{2B}R^{2C}$, —NHC(O)NHNR$^{2B}R^{2C}$, —NHC(O)NR$^{2B}R^{2C}$, —$N(O)_{m1}$, —$NR^{2B}R^{2C}$, —$C(O)R^{2D}$, —$C(O)OR^{2D}$, —$C(O)NR^{2B}R^{2C}$, —$OR^{2A}$, —$NR^{2B}SO_2R^{2A}$, —$NR^{2B}C(O)R^{2D}$, —$NR^{2B}C(O)$ $OR^{2D}$, —$NR^{2B}OR^{2D}$, —$OCX^{2.1}_3$, —$OCHX^{2.1}_2$, substituted or unsubstituted alkylene or substituted or unsubstituted heteroalkylene, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $L^2$ is a bond.

In embodiments, $L^2$ is substituted or unsubstituted alkylene (e.g. $C_1$-$C_{18}$ alkylene, $C_1$-$C_{16}$ alkylene, $C_1$-$C_{14}$ alkylene, $C_1$-$C_{10}$ alkylene, $C_1$-$C_8$ alkylene, $C_1$-$C_6$ alkylene, or $C_1$-$C_4$ alkylene), substituted or unsubstituted heteroalkylene (e.g. 2 to 20 membered heteroalkylene, 2 to 18 membered heteroalkylene, 4 to 18 membered heteroalkylene, 2 to 16 membered heteroalkylene, 2 to 14 membered heteroalkylene, 2 to 10 membered heteroalkylene, 2 to 8 membered heteroalkylene, 4 to 8 membered heteroalkylene, 2 to 6 membered heteroalkylene, or 2 to 4 membered heteroalkylene), substituted or unsubstituted cycloalkylene (e.g. $C_3$-$C_8$ cycloalkylene, $C_4$-$C_8$ cycloalkylene, or $C_5$-$C_6$ cycloalkylene), substituted or unsubstituted heterocycloalkylene (e.g. 3 to 8 membered heterocycloalkylene, 4 to 8 membered heterocycloalkylene, or 5 to 6 membered heterocycloalkylene), substituted or unsubstituted arylene (e.g. $C_6$-$C_{10}$ arylene or $C_6$ arylene), or substituted or unsubstituted heteroarylene (e.g. 5 to 10 membered heteroarylene, 5 to 9 membered heteroarylene, or 5 to 6 membered heteroarylene).

In embodiments, $L^2$ is substituted or unsubstituted alkylene (e.g. $C_1$-$C_{18}$ alkylene, $C_1$-$C_{16}$ alkylene, $C_1$-$C_{14}$ alkylene, $C_1$-$C_{10}$ alkylene, $C_1$-$C_8$ alkylene, $C_1$-$C_6$ alkylene, or $C_1$-$C_4$ alkylene). In embodiments, $L^2$ is substituted or unsubstituted $C_1$-$C_8$ alkylene. In embodiments, $L^2$ is substituted $C_1$-$C_8$ alkylene. In embodiments, $L^2$ is $R^8$-substituted $C_1$-$C_8$ alkylene. In embodiments, $L^2$ is unsubstituted $C_1$-$C_8$ alkylene. In embodiments, $L^2$ is substituted or unsubstituted $C_8$ alkylene. In embodiments, $L^2$ is substituted $C_8$ alkylene. In embodiments, $L^2$ is $R^8$-substituted $C_8$ alkylene. In embodiments, $L^2$ is unsubstituted $C_8$ alkylene. In embodiments, $L^2$ is substituted or unsubstituted $C_6$ alkylene. In embodiments, $L^2$ is substituted $C_6$ alkylene. In embodiments, $L^2$ is $R^8$-substituted $C_6$ alkylene. In embodiments, $L^2$ is unsubstituted $C_6$ alkylene.

In embodiments, $L^2$ is substituted or unsubstituted heteroalkylene (e.g. 2 to 20 membered heteroalkylene, 2 to 18 membered heteroalkylene, 4 to 18 membered heteroalkylene, 2 to 16 membered heteroalkylene, 2 to 14 membered heteroalkylene, 2 to 10 membered heteroalkylene, 2 to 8 membered heteroalkylene, 4 to 8 membered heteroalkylene, 2 to 6 membered heteroalkylene, or 2 to 4 membered heteroalkylene). In embodiments, $L^2$ is substituted or unsubstituted 2 to 20 membered heteroalkylene. In embodiments, $L^2$ is substituted 2 to 20 membered heteroalkylene. In embodiments, $L^2$ is $R^8$-substituted 2 to 20 membered heteroalkylene. In embodiments, $L^2$ is unsubstituted 2 to 20 membered heteroalkylene. In embodiments, $L^2$ is substituted 20 membered heteroalkylene. In embodiments, $L^2$ is $R^8$-substituted 20 membered heteroalkylene. In embodiments, $L^2$ is unsubstituted 20 membered heteroalkylene. In embodiments, $L^2$ is substituted 19 membered heteroalkylene. In embodiments, $L^2$ is $R^8$-substituted 19 membered heteroalkylene. In embodiments, $L^2$ is unsubstituted 19 membered heteroalkylene. In embodiments, $L^2$ is substituted 18 membered heteroalkylene. In embodiments, $L^2$ is $R^8$-substituted 18 membered heteroalkylene. In embodiments, $L^2$ is unsubstituted 18 membered heteroalkylene. In embodiments, $L^2$ is substituted 17 membered heteroalkylene. In embodiments, $L^2$ is $R^8$-substituted 17 membered heteroalkylene. In embodiments, $L^2$ is unsubstituted 17 membered heteroalkylene. In embodiments, $L^2$ is substituted 16 membered heteroalkylene. In embodiments, $L^2$ is $R^8$-substituted 16 membered heteroalkylene. In embodiments, $L^2$ is unsubstituted 16 membered heteroalkylene.

In embodiments, $L^2$ is substituted or unsubstituted 2 to 10 membered heteroalkylene. In embodiments, $L^2$ is substituted 2 to 10 membered heteroalkylene. In embodiments, $L^2$ is $R^8$-substituted 2 to 10 membered heteroalkylene. In embodiments, $L^2$ is unsubstituted 2 to 10 membered heteroalkylene. In embodiments, $L^2$ is substituted 10 membered heteroalkylene. In embodiments, $L^2$ is $R^8$-substituted 10 membered heteroalkylene. In embodiments, $L^2$ is unsubstituted 10 membered heteroalkylene. In embodiments, $L^2$ is substituted 9 membered heteroalkylene. In embodiments, $L^2$ is $R^8$-substituted 9 membered heteroalkylene. In embodiments, $L^2$ is unsubstituted 9 membered heteroalkylene. In embodiments, $L^2$ is substituted 8 membered heteroalkylene. In embodiments, $L^2$ is $R^8$-substituted 8 membered heteroalkylene. In embodiments, $L^2$ is unsubstituted 8 membered heteroalkylene. In embodiments, $L^2$ is substituted 7 membered heteroalkylene. In embodiments, $L^2$ is $R^8$-substituted 7 membered heteroalkylene. In embodiments, $L^2$ is unsubstituted 7 membered heteroalkylene. In embodiments, $L^2$ is substituted 6 membered heteroalkylene. In embodiments, $L^2$ is $R^8$-substituted 6 membered heteroalkylene. In embodiments, $L^2$ is unsubstituted 6 membered heteroalkylene.

In embodiments, $L^2$ is $R^8$-substituted or unsubstituted alkylene (e.g. $C_1$-$C_8$ alkylene, $C_1$-$C_6$ alkylene, or $C_1$-$C_4$ alkylene), $R^8$-substituted or unsubstituted heteroalkylene (e.g. 2 to 10 membered heteroalkylene, 2 to 8 membered heteroalkylene, 4 to 8 membered heteroalkylene, 2 to 6 membered heteroalkylene, or 2 to 4 membered heteroalkylene), $R^8$-substituted or unsubstituted cycloalkylene (e.g. $C_3$-$C_8$ cycloalkylene, $C_4$-$C_8$ cycloalkylene, or $C_5$-$C_6$ cycloalkylene), $R^8$-substituted or unsubstituted heterocycloalkylene (e.g. 3 to 8 membered heterocycloalkylene, 4 to 8 membered heterocycloalkylene, or 5 to 6 membered heterocycloalkylene), $R^8$-substituted or unsubstituted arylene (e.g. $C_6$-$C_{10}$ arylene or $C_6$ arylene), or $R^8$-substituted or unsubstituted heteroarylene (e.g. 5 to 10 membered heteroarylene, 5 to 9 membered heteroarylene, or 5 to 6 membered heteroarylene).

$R^8$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O) $NHNH_2$, —NHC=(O) $NH_2$, —$NHSO_2H$, —NHC=(O)H, —NHC(O)—OH, —NHOH, —$OCF_3$, —$OCHF_2$, $R^9$-substituted or unsubstituted alkyl (e.g. $C_1$-$C_8$ alkyl, $C_1$-$C_6$ alkyl, or $C_1$-$C_4$ alkyl), $R^9$-substituted or unsubstituted heteroalkyl (e.g. 2 to 8 membered heteroalkyl, 2 to 6 membered heteroalkyl, or 2 to 4 membered heteroalkyl), $R^9$-substituted or unsubstituted cycloalkyl (e.g. $C_3$-$C_8$ cycloalkyl, $C_4$-$C_8$ cycloalkyl, or $C_5$-$C_6$ cycloalkyl), $R^9$-substituted or unsubstituted heterocycloalkyl (e.g. 3 to 8 membered heterocycloalkyl, 4 to 8 membered heterocycloalkyl, or 5 to 6 membered heterocycloalkyl), $R^9$-substituted or unsubstituted aryl (e.g. $C_6$-$C_{10}$ aryl or $C_6$ aryl), or $R^9$-substituted or unsubstituted heteroaryl (e.g. 5 to 10 membered heteroaryl, 5 to 9 membered heteroaryl, or 5 to 6 membered heteroaryl).

In embodiments, $R^8$ is substituted napthyl. In embodiments, $R^8$ is $R^9$-substituted napthyl. In embodiments, $R^8$ is unsubstituted napthyl. In embodiments, $R^8$ is substituted isoquinoline. In embodiments, $R^8$ is $R^9$-substituted isoquinoline. In embodiments, $R^8$ is unsubstituted isoquinoline. In embodiments, $R^8$ is substituted quinoline. In embodiments, $R^8$ is $R^9$-substituted quinoline. In embodiments, $R^8$ is unsubstituted quinoline. In embodiments, $R^8$ is substituted tetrazine. In embodiments, $R^8$ is $R^9$-substituted tetrazine. In embodiments, $R^8$ is unsubstituted tetrazine.

In embodiments, $R^8$ is

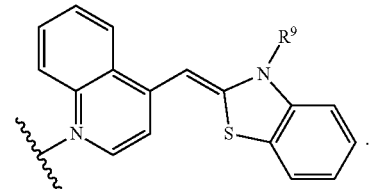

In embodiments, $R^8$ is

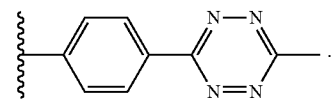

In embodiments, $R^8$ is

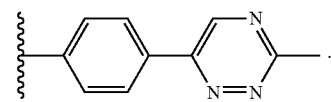

In embodiments, $R^8$ is

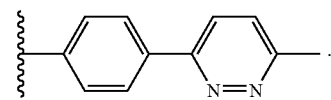

$R^9$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O) $NHNH_2$, —NHC=(O) $NH_2$, —$NHSO_2H$, —NHC=(O)H, —NHC(O)—OH, —NHOH, —$OCF_3$, —$OCHF_2$, $R^{10}$-substituted or unsubstituted alkyl (e.g. $C_1$-$C_8$ alkyl, $C_1$-$C_6$ alkyl, or $C_1$-$C_4$ alkyl), $R^{10}$-substituted or unsubstituted heteroalkyl (e.g. 2 to 8 membered heteroalkyl, 2 to 6 membered heteroalkyl, or 2 to 4 membered heteroalkyl), $R^{10}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{10}$-substituted or unsubstituted heterocycloalkyl (e.g. 3 to 8 membered heterocycloalkyl, 4 to 8 membered heterocycloalkyl, or 5 to 6 membered heterocycloalkyl), $R^{10}$-substituted or unsubstituted aryl (e.g. $C_6$-$C_{10}$ aryl or $C_6$ aryl), or $R^{10}$-substituted or unsubstituted heteroaryl (e.g. 5 to 10 membered heteroaryl, 5 to 9 membered heteroaryl, or 5 to 6 membered heteroaryl).

In embodiments, $R^9$ is substituted napthyl. In embodiments, $R^9$ is $R^{10}$-substituted napthyl. In embodiments, $R^9$ is unsubstituted napthyl. In embodiments, $R^9$ is substituted isoquinoline. In embodiments, $R^9$ is $R^{10}$-substituted isoquinoline. In embodiments, $R^9$ is unsubstituted isoquinoline. In embodiments, $R^9$ is substituted quinoline. In embodiments, $R^9$ is $R^{10}$-substituted quinoline. In embodiments, $R^9$ is unsubstituted quinoline. In embodiments, $R^9$ is substituted tetrazine. In embodiments, $R^9$ is $R^{10}$-substituted tetrazine. In embodiments, $R^9$ is unsubstituted tetrazine.

In embodiments, $R^9$ is

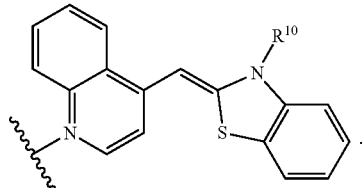

In embodiments, $R^9$ is

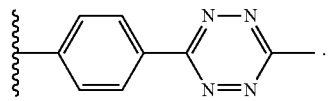

In embodiments, $R^9$ is

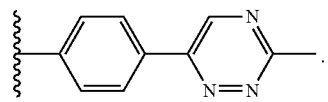

In embodiments, $R^9$ is

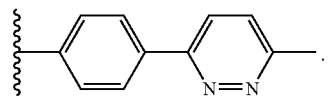 [SMILES: *c1ccc(-c2ccc(C)nn2)cc1]

In embodiments, $R^3$ is a biomolecule. In embodiments, $R^3$ is a dye. In embodiments, $R^3$ a fluorophore. In embodiments, $R^3$ is an affinity ligand. In embodiments, $R^3$ is an antibody. In embodiments, $R^3$ is a polypeptide. In embodiments, $R^3$ is a protein. In embodiments, $R^3$ is a nucleic acid molecule. In embodiments, $R^3$ is biocytin. In embodiments, $R^3$ is biotin. In embodiments, $R^3$ is a boron-dipyrromethene dye. In embodiments, $R^3$ is a cyanine dye. In embodiments, $R^3$ is a thiazole compound. In embodiments, $R^3$ is thiazole orange (TO). In embodiments, $R^3$ is a thiazole orange derivative.

In embodiments, $R^3$ is hydrogen, halogen, $CF_3$, $-CCl_3$, $-CBr_3$, $-CI_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCF_3$, $-OCCl_3$, $-OCBr_3$, $-OCI_3$, $-OCHF_2$, $-OCHCl_2$, $-OCHBr_2$, $-OCHI_2$, $R^{11}$-substituted or unsubstituted alkyl (e.g. $C_1$-$C_8$ alkyl, $C_1$-$C_6$ alkyl, or $C_1$-$C_4$ alkyl), $R^{11}$-substituted or unsubstituted heteroalkyl (e.g. 2 to 8 membered heteroalkyl, 2 to 6 membered heteroalkyl, or 2 to 4 membered heteroalkyl), $R^{11}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{11}$-substituted or unsubstituted heterocycloalkyl (e.g. 3 to 8 membered heterocycloalkyl, 4 to 8 membered heterocycloalkyl, or 5 to 6 membered heterocycloalkyl), $R^{11}$-substituted or unsubstituted aryl (e.g. $C_6$-$C_{10}$ aryl or $C_6$ aryl), or $R^{11}$-substituted or unsubstituted heteroaryl (e.g. 5 to 10 membered heteroaryl, 5 to 9 membered heteroaryl, or 5 to 6 membered heteroaryl).

$R^{11}$ is independently oxo, halogen, $-CF_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O) NH_2$, $-NHSO_2H$, $-NHC=(O)H$, $-NHC(O)-OH$, $-NHOH$, $-OCF_3$, $-OCHF_2$, $R^{12}$-substituted or unsubstituted alkyl (e.g. $C_1$-$C_8$ alkyl, $C_1$-$C_6$ alkyl, or $C_1$-$C_4$ alkyl), $R^{12}$-substituted or unsubstituted heteroalkyl (e.g. 2 to 8 membered heteroalkyl, 2 to 6 membered heteroalkyl, or 2 to 4 membered heteroalkyl), $R^{12}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{12}$-substituted or unsubstituted heterocycloalkyl (e.g. 3 to 8 membered heterocycloalkyl, 4 to 8 membered heterocycloalkyl, or 5 to 6 membered heterocycloalkyl), $R^{12}$-substituted or unsubstituted aryl (e.g. $C_6$-$C_{10}$ aryl or $C_6$ aryl), or $R^{12}$-substituted or unsubstituted heteroaryl (e.g. 5 to 10 membered heteroaryl, 5 to 9 membered heteroaryl, or 5 to 6 membered heteroaryl).

In embodiments, $R^{14}$ is independently oxo, halogen, $-CF_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O) NH_2$, $-NHSO_2H$, $-NHC=(O)H$, $-NHC(O)-OH$, $-NHOH$, $-OCF_3$, $-OCHF_2$, $R^{5A}$-substituted or unsubstituted alkyl (e.g. $C_1$-$C_8$ alkyl, $C_1$-$C_6$ alkyl, or $C_1$-$C_4$ alkyl), $R^{5A}$-substituted or unsubstituted heteroalkyl (e.g. 2 to 8 membered heteroalkyl, 2 to 6 membered heteroalkyl, or 2 to 4 membered heteroalkyl), $R^{5A}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{5A}$-substituted or unsubstituted heterocycloalkyl (e.g. 3 to 8 membered heterocycloalkyl, 4 to 8 membered heterocycloalkyl, or 5 to 6 membered heterocycloalkyl), $R^{5A}$-substituted or unsubstituted aryl (e.g. $C_6$-$C_{10}$ aryl or $C_6$ aryl), or $R^{5A}$-substituted or unsubstituted heteroaryl (e.g. 5 to 10 membered heteroaryl, 5 to 9 membered heteroaryl, or 5 to 6 membered heteroaryl).

$R^{5A}$ is independently oxo, halogen, $-CF_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O) NH_2$, $-NHSO_2H$, $-NHC=(O)H$, $-NHC(O)-OH$, $-NHOH$, $-OCF_3$, $-OCHF_2$, $R^{6A}$-substituted or unsubstituted alkyl (e.g. $C_1$-$C_8$ alkyl, $C_1$-$C_6$ alkyl, or $C_1$-$C_4$ alkyl), $R^{6A}$-substituted or unsubstituted heteroalkyl (e.g. 2 to 8 membered heteroalkyl, 2 to 6 membered heteroalkyl, or 2 to 4 membered heteroalkyl), $R^{6A}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{6A}$-substituted or unsubstituted heterocycloalkyl (e.g. 3 to 8 membered heterocycloalkyl, 4 to 8 membered heterocycloalkyl, or 5 to 6 membered heterocycloalkyl), $R^{6A}$-substituted or unsubstituted aryl (e.g. $C_6$-$C_{10}$ aryl or $C_6$ aryl), or $R^{6A}$-substituted or unsubstituted heteroaryl (e.g. 5 to 10 membered heteroaryl, 5 to 9 membered heteroaryl, or 5 to 6 membered heteroaryl).

$R^{6A}$ is independently oxo, halogen, $-CF_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O) NH_2$, $-NHSO_2H$, $-NHC=(O)H$, $-NHC(O)-OH$, $-NHOH$, $-OCF_3$, $-OCHF_2$, $R^{7A}$-substituted or unsubstituted alkyl (e.g. $C_1$-$C_8$ alkyl, $C_1$-$C_6$ alkyl, or $C_1$-$C_4$ alkyl), $R^{7A}$-substituted or unsubstituted heteroalkyl (e.g. 2 to 8 membered heteroalkyl, 2 to 6 membered heteroalkyl, or 2 to 4 membered heteroalkyl), $R^{7A}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{7A}$-substituted or unsubstituted heterocycloalkyl (e.g. 3 to 8 membered heterocycloalkyl, 4 to 8 membered heterocycloalkyl, or 5 to 6 membered heterocycloalkyl), $R^{7A}$-substituted or unsubstituted aryl (e.g. $C_6$-$C_{10}$ aryl or $C_6$ aryl), or $R^{7A}$-substituted or unsubstituted heteroaryl (e.g. 5 to 10 membered heteroaryl, 5 to 9 membered heteroaryl, or 5 to 6 membered heteroaryl).

In embodiments, $R^{1B}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{5B}$-substituted or unsubstituted alkyl (e.g. $C_1$-$C_8$ alkyl, $C_1$-$C_6$ alkyl, or $C_1$-$C_4$ alkyl), $R^{5B}$-substituted or unsubstituted heteroalkyl (e.g. 2 to 8 membered heteroalkyl, 2 to 6 membered heteroalkyl, or 2 to 4 membered heteroalkyl), $R^{5B}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{5B}$—substituted or unsubstituted heterocycloalkyl (e.g. 3 to 8 membered heterocycloalkyl, 4 to 8 membered heterocycloalkyl, or 5 to 6 membered heterocycloalkyl), $R^{5B}$-substituted or unsubstituted aryl (e.g. $C_6$-$C_{10}$ aryl or $C_6$ aryl), or $R^{5B}$-substituted or unsubstituted heteroaryl (e.g. 5 to 10 membered heteroaryl, 5 to 9 membered heteroaryl, or 5 to 6 membered heteroaryl).

$R^{5B}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{6B}$-substituted or unsubstituted alkyl (e.g. $C_1$-$C_8$ alkyl, $C_1$-$C_6$ alkyl, or $C_1$-$C_4$ alkyl), $R^{6B}$-substituted or unsubstituted heteroalkyl (e.g. 2 to 8 membered heteroalkyl, 2 to 6 membered heteroalkyl, or 2 to 4 membered heteroalkyl), $R^{6B}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{6B}$-substituted or unsubstituted heterocycloalkyl (e.g. 3 to 8 membered heterocycloalkyl, 4 to 8 membered heterocycloalkyl, or 5 to 6 membered heterocycloalkyl), $R^{6B}$-substituted or unsubstituted aryl (e.g. $C_6$-$C_{10}$ aryl or $C_6$ aryl), or $R^{6B}$-substituted or unsubstituted heteroaryl (e.g. 5 to 10 membered heteroaryl, 5 to 9 membered heteroaryl, or 5 to 6 membered heteroaryl).

$R^{6B}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{7B}$-substituted or unsubstituted alkyl (e.g. $C_1$-$C_8$ alkyl, $C_1$-$C_6$ alkyl, or $C_1$-$C_4$ alkyl), $R^{7B}$-substituted or unsubstituted heteroalkyl (e.g. 2 to 8 membered heteroalkyl, 2 to 6 membered heteroalkyl, or 2 to 4 membered heteroalkyl), $R^{7B}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{7B}$-substituted or unsubstituted heterocycloalkyl (e.g. 3 to 8 membered heterocycloalkyl, 4 to 8 membered heterocycloalkyl, or 5 to 6 membered heterocycloalkyl), $R^{7B}$-substituted or unsubstituted aryl (e.g. $C_6$-$C_{10}$ aryl or $C_6$ aryl), or $R^{7B}$-substituted or unsubstituted heteroaryl (e.g. 5 to 10 membered heteroaryl, 5 to 9 membered heteroaryl, or 5 to 6 membered heteroaryl).

In embodiments, $R^{1C}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{5C}$-substituted or unsubstituted alkyl (e.g. $C_1$-$C_8$ alkyl, $C_1$-$C_6$ alkyl, or $C_1$-$C_4$ alkyl), $R^{5C}$-substituted or unsubstituted heteroalkyl (e.g. 2 to 8 membered heteroalkyl, 2 to 6 membered heteroalkyl, or 2 to 4 membered heteroalkyl), $R^{5C}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{5C}$-substituted or unsubstituted heterocycloalkyl (e.g. 3 to 8 membered heterocycloalkyl, 4 to 8 membered heterocycloalkyl, or 5 to 6 membered heterocycloalkyl), $R^{5C}$-substituted or unsubstituted aryl (e.g. $C_6$-$C_{10}$ aryl or $C_6$ aryl), or $R^{5C}$-substituted or unsubstituted heteroaryl (e.g. 5 to 10 membered heteroaryl, 5 to 9 membered heteroaryl, or 5 to 6 membered heteroaryl).

$R^{5C}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{6C}$-substituted or unsubstituted alkyl (e.g. $C_1$-$C_8$ alkyl, $C_1$-$C_6$ alkyl, or $C_1$-$C_4$ alkyl), $R^{6C}$-substituted or unsubstituted heteroalkyl (e.g. 2 to 8 membered heteroalkyl, 2 to 6 membered heteroalkyl, or 2 to 4 membered heteroalkyl), $R^{6C}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{6C}$-substituted or unsubstituted heterocycloalkyl (e.g. 3 to 8 membered heterocycloalkyl, 4 to 8 membered heterocycloalkyl, or 5 to 6 membered heterocycloalkyl), $R^{6C}$-substituted or unsubstituted aryl (e.g. $C_6$-$C_{10}$ aryl or $C_6$ aryl), or $R^{6C}$-substituted or unsubstituted heteroaryl (e.g. 5 to 10 membered heteroaryl, 5 to 9 membered heteroaryl, or 5 to 6 membered heteroaryl).

$R^{6C}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{7C}$-substituted or unsubstituted alkyl (e.g. $C_1$-$C_8$ alkyl, $C_1$-$C_6$ alkyl, or $C_1$-$C_4$ alkyl), $R^{7C}$-substituted or unsubstituted heteroalkyl (e.g. 2 to 8 membered heteroalkyl, 2 to 6 membered heteroalkyl, or 2 to 4 membered heteroalkyl), $R^{7C}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{7C}$-substituted or unsubstituted heterocycloalkyl (e.g. 3 to 8 membered heterocycloalkyl, 4 to 8 membered heterocycloalkyl, or 5 to 6 membered heterocycloalkyl), $R^{7C}$-substituted or unsubstituted aryl (e.g. $C_6$-$C_{10}$ aryl or $C_6$ aryl), or $R^{7C}$-substituted or unsubstituted heteroaryl (e.g. 5 to 10 membered heteroaryl, 5 to 9 membered heteroaryl, or 5 to 6 membered heteroaryl).

In embodiments, $R^{1D}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{5D}$-substituted or unsubstituted alkyl (e.g. $C_1$-$C_8$ alkyl, $C_1$-$C_6$ alkyl, or $C_1$-$C_4$ alkyl), $R^{5D}$-substituted or unsubstituted heteroalkyl (e.g. 2 to 8 membered heteroalkyl, 2 to 6 membered heteroalkyl, or 2 to 4 membered heteroalkyl), $R^{5D}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{5D}$-substituted or unsubstituted heterocycloalkyl (e.g. 3 to 8 membered heterocycloalkyl, 4 to 8 membered heterocycloalkyl, or 5 to 6 membered heterocycloalkyl), $R^{5D}$-substituted or unsubstituted aryl (e.g. $C_6$-$C_{10}$ aryl or $C_6$ aryl), or $R^{5D}$-substituted or unsubstituted heteroaryl (e.g. 5 to 10 membered heteroaryl, 5 to 9 membered heteroaryl, or 5 to 6 membered heteroaryl).

$R^{5D}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{6D}$-substituted or unsubstituted alkyl (e.g. $C_1$-$C_8$ alkyl, $C_1$-$C_6$ alkyl, or $C_1$-$C_4$ alkyl), $R^{6D}$-substituted or unsubstituted heteroalkyl (e.g. 2 to 8 membered heteroalkyl, 2 to 6 membered heteroalkyl, or 2 to 4 membered heteroalkyl), $R^{6D}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{6D}$-substituted or unsubstituted heterocycloalkyl (e.g. 3 to 8 membered heterocycloalkyl, 4 to 8 membered heterocycloalkyl, or 5 to 6 membered heterocycloalkyl), $R^{6D}$-substituted or unsubstituted aryl (e.g. $C_6$-$C_{10}$ aryl or $C_6$ aryl), or $R^{6D}$-substituted or unsubstituted heteroaryl (e.g. 5 to 10 membered heteroaryl, 5 to 9 membered heteroaryl, or 5 to 6 membered heteroaryl).

$R^{6D}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O) $NH_2$, —$NHSO_2H$, —NHC═(O)H, —NHC(O)—OH, —NHOH, —$OCF_3$, —$OCHF_2$, $R^{7D}$-substituted or unsubstituted alkyl (e.g. $C_1$-$C_8$ alkyl, $C_1$-$C_6$ alkyl, or $C_1$-$C_4$ alkyl), $R^{7D}$-substituted or unsubstituted heteroalkyl (e.g. 2 to 8 membered heteroalkyl, 2 to 6 membered heteroalkyl, or 2 to 4 membered heteroalkyl), $R^{7D}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{7D}$-substituted or unsubstituted heterocycloalkyl (e.g. 3 to 8 membered heterocycloalkyl, 4 to 8 membered heterocycloalkyl, or 5 to 6 membered heterocycloalkyl), $R^{7D}$-substituted or unsubstituted aryl (e.g. $C_6$-$C_{10}$ aryl or $C_6$ aryl), or $R^{7D}$-substituted or unsubstituted heteroaryl (e.g. 5 to 10 membered heteroaryl, 5 to 9 membered heteroaryl, or 5 to 6 membered heteroaryl).

In embodiments, $R^{2A}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O) $NH_2$, —$NHSO_2H$, —NHC═(O)H, —NHC(O)—OH, —NHOH, —$OCF_3$, —$OCHF_2$, $R^{8A}$-substituted or unsubstituted alkyl (e.g. $C_1$-$C_8$ alkyl, $C_1$-$C_6$ alkyl, or $C_1$-$C_4$ alkyl), $R^{8A}$-substituted or unsubstituted heteroalkyl (e.g. 2 to 8 membered heteroalkyl, 2 to 6 membered heteroalkyl, or 2 to 4 membered heteroalkyl), $R^{8A}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{8A}$-substituted or unsubstituted heterocycloalkyl (e.g. 3 to 8 membered heterocycloalkyl, 4 to 8 membered heterocycloalkyl, or 5 to 6 membered heterocycloalkyl), $R^{8A}$-substituted or unsubstituted aryl (e.g. $C_6$-$C_{10}$ aryl or $C_6$ aryl), or $R^{8A}$-substituted or unsubstituted heteroaryl (e.g. 5 to 10 membered heteroaryl, 5 to 9 membered heteroaryl, or 5 to 6 membered heteroaryl).

$R^{8A}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O) $NH_2$, —$NHSO_2H$, —NHC═(O)H, —NHC(O)—OH, —NHOH, —$OCF_3$, —$OCHF_2$, $R^{9A}$-substituted or unsubstituted alkyl (e.g. $C_1$-$C_8$ alkyl, $C_1$-$C_6$ alkyl, or $C_1$-$C_4$ alkyl), $R^{9A}$-substituted or unsubstituted heteroalkyl (e.g. 2 to 8 membered heteroalkyl, 2 to 6 membered heteroalkyl, or 2 to 4 membered heteroalkyl), $R^{9A}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{9A}$-substituted or unsubstituted heterocycloalkyl (e.g. 3 to 8 membered heterocycloalkyl, 4 to 8 membered heterocycloalkyl, or 5 to 6 membered heterocycloalkyl), $R^{9A}$-substituted or unsubstituted aryl (e.g. $C_6$-$C_{10}$ aryl or $C_6$ aryl), or $R^{9A}$-substituted or unsubstituted heteroaryl (e.g. 5 to 10 membered heteroaryl, 5 to 9 membered heteroaryl, or 5 to 6 membered heteroaryl).

$R^{9A}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O) $NH_2$, —$NHSO_2H$, —NHC═(O)H, —NHC(O)—OH, —NHOH, —$OCF_3$, —$OCHF_2$, $R^{10A}$-substituted or unsubstituted alkyl (e.g. $C_1$-$C_8$ alkyl, $C_1$-$C_6$ alkyl, or $C_1$-$C_4$ alkyl), $R^{10A}$-substituted or unsubstituted heteroalkyl (e.g. 2 to 8 membered heteroalkyl, 2 to 4 membered heteroalkyl), $R^{10A}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{10A}$-substituted or unsubstituted heterocycloalkyl (e.g. 3 to 8 membered heterocycloalkyl, 4 to 8 membered heterocycloalkyl, or 5 to 6 membered heterocycloalkyl), $R^{10A}$-substituted or unsubstituted aryl (e.g. $C_6$-$C_{10}$ aryl or $C_6$ aryl), or $R^{10A}$-substituted or unsubstituted heteroaryl (e.g. 5 to 10 membered heteroaryl, 5 to 9 membered heteroaryl, or 5 to 6 membered heteroaryl).

In embodiments, $R^{2B}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O) $NH_2$, —$NHSO_2H$, —NHC═(O)H, —NHC(O)—OH, —NHOH, —$OCF_3$, —$OCHF_2$, $R^{8B}$-substituted or unsubstituted alkyl (e.g. $C_1$-$C_8$ alkyl, $C_1$-$C_6$ alkyl, or $C_1$-$C_4$ alkyl), $R^{8B}$-substituted or unsubstituted heteroalkyl (e.g. 2 to 8 membered heteroalkyl, 2 to 6 membered heteroalkyl, or 2 to 4 membered heteroalkyl), $R^{8B}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{8B}$-substituted or unsubstituted heterocycloalkyl (e.g. 3 to 8 membered heterocycloalkyl, 4 to 8 membered heterocycloalkyl, or 5 to 6 membered heterocycloalkyl), $R^{8B}$-substituted or unsubstituted aryl (e.g. $C_6$-$C_{10}$ aryl or $C_6$ aryl), or $R^{8B}$-substituted or unsubstituted heteroaryl (e.g. 5 to 10 membered heteroaryl, 5 to 9 membered heteroaryl, or 5 to 6 membered heteroaryl).

$R^{8B}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O) $NH_2$, —$NHSO_2H$, —NHC═(O)H, —NHC(O)—OH, —NHOH, —$OCF_3$, —$OCHF_2$, $R^{9B}$-substituted or unsubstituted alkyl (e.g. $C_1$-$C_8$ alkyl, $C_1$-$C_6$ alkyl, or $C_1$-$C_4$ alkyl), $R^{9B}$-substituted or unsubstituted heteroalkyl (e.g. 2 to 8 membered heteroalkyl, 2 to 6 membered heteroalkyl, or 2 to 4 membered heteroalkyl), $R^{9B}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{9B}$-substituted or unsubstituted heterocycloalkyl (e.g. 3 to 8 membered heterocycloalkyl, 4 to 8 membered heterocycloalkyl, or 5 to 6 membered heterocycloalkyl), $R^{9B}$-substituted or unsubstituted aryl (e.g. $C_6$-$C_{10}$ aryl or $C_6$ aryl), or $R^{9B}$-substituted or unsubstituted heteroaryl (e.g. 5 to 10 membered heteroaryl, 5 to 9 membered heteroaryl, or 5 to 6 membered heteroaryl).

$R^{9B}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O) $NH_2$, —$NHSO_2H$, —NHC═(O)H, —NHC(O)—OH, —NHOH, —$OCF_3$, —$OCHF_2$, $R^{10B}$-substituted or unsubstituted alkyl (e.g. $C_1$-$C_8$ alkyl, $C_1$-$C_6$ alkyl, or $C_1$-$C_4$ alkyl), $R^{10B}$-substituted or unsubstituted heteroalkyl (e.g. 2 to 8 membered heteroalkyl, 2 to 6 membered heteroalkyl, or 2 to 4 membered heteroalkyl), $R^{10B}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{10B}$-substituted or unsubstituted heterocycloalkyl (e.g. 3 to 8 membered heterocycloalkyl, 4 to 8 membered heterocycloalkyl, or 5 to 6 membered heterocycloalkyl), $R^{10B}$-substituted or unsubstituted aryl (e.g. $C_6$-$C_{10}$ aryl or $C_6$ aryl), or $R^{10B}$-substituted or unsubstituted heteroaryl (e.g. 5 to 10 membered heteroaryl, 5 to 9 membered heteroaryl, or 5 to 6 membered heteroaryl).

In embodiments, $R^{2C}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O) $NH_2$, —NHSO$_2$H, —NHC=(O)H, —NHC(O)—OH, —NHOH, —OCF$_3$, —OCHF$_2$, R$^{8C}$-substituted or unsubstituted alkyl (e.g. C$_1$-C$_8$ alkyl, C$_1$-C$_6$ alkyl, or C$_1$-C$_4$ alkyl), R$^{8C}$-substituted or unsubstituted heteroalkyl (e.g. 2 to 8 membered heteroalkyl, 2 to 6 membered heteroalkyl, or 2 to 4 membered heteroalkyl), R$^{8C}$-substituted or unsubstituted cycloalkyl (e.g. C$_3$-C$_8$ cycloalkyl, C$_4$-C$_8$ cycloalkyl, or C$_5$-C$_6$ cycloalkyl), R$^{8C}$-substituted or unsubstituted heterocycloalkyl (e.g. 3 to 8 membered heterocycloalkyl, 4 to 8 membered heterocycloalkyl, or 5 to 6 membered heterocycloalkyl), R$^{8C}$-substituted or unsubstituted aryl (e.g. C$_6$-C$_{10}$ aryl or C$_6$ aryl), or R$^{8C}$-substituted or unsubstituted heteroaryl (e.g. 5 to 10 membered heteroaryl, 5 to 9 membered heteroaryl, or 5 to 6 membered heteroaryl).

R$^{8C}$ is independently oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O) NHNH$_2$, —NHC=(O) NH$_2$, —NHSO$_2$H, —NHC=(O)H, —NHC(O)—OH, —NHOH, —OCF$_3$, —OCHF$_2$, R$^{9C}$-substituted or unsubstituted alkyl (e.g. C$_1$-C$_8$ alkyl, C$_1$-C$_6$ alkyl, or C$_1$-C$_4$ alkyl), R$^{9C}$-substituted or unsubstituted heteroalkyl (e.g. 2 to 8 membered heteroalkyl, 2 to 6 membered heteroalkyl, or 2 to 4 membered heteroalkyl), R$^{9C}$-substituted or unsubstituted cycloalkyl (e.g. C$_3$-C$_8$ cycloalkyl, C$_4$-C$_8$ cycloalkyl, or C$_5$-C$_6$ cycloalkyl), R$^{9C}$-substituted or unsubstituted heterocycloalkyl (e.g. 3 to 8 membered heterocycloalkyl, 4 to 8 membered heterocycloalkyl, or 5 to 6 membered heterocycloalkyl), R$^{9C}$-substituted or unsubstituted aryl (e.g. C$_6$-C$_{10}$ aryl or C$_6$ aryl), or R$^{9C}$-substituted or unsubstituted heteroaryl (e.g. 5 to 10 membered heteroaryl, 5 to 9 membered heteroaryl, or 5 to 6 membered heteroaryl).

R$^{9C}$ is independently oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O) NHNH$_2$, —NHC=(O) NH$_2$, —NHSO$_2$H, —NHC=(O)H, —NHC(O)—OH, —NHOH, —OCF$_3$, —OCHF$_2$, R$^{10C}$-substituted or unsubstituted alkyl (e.g. C$_1$-C$_8$ alkyl, C$_1$-C$_6$ alkyl, or C$_1$-C$_4$ alkyl), R$^{10C}$-substituted or unsubstituted heteroalkyl (e.g. 2 to 8 membered heteroalkyl, 2 to 6 membered heteroalkyl, or 2 to 4 membered heteroalkyl), R$^{10C}$-substituted or unsubstituted cycloalkyl (e.g. C$_3$-C$_8$ cycloalkyl, C$_4$-C$_8$ cycloalkyl, or C$_5$-C$_6$ cycloalkyl), R$^{10C}$-substituted or unsubstituted heterocycloalkyl (e.g. 3 to 8 membered heterocycloalkyl, 4 to 8 membered heterocycloalkyl, or 5 to 6 membered heterocycloalkyl), R$^{10C}$-substituted or unsubstituted aryl (e.g. C$_6$-C$_{10}$ aryl or C$_6$ aryl), or R$^{10C}$-substituted or unsubstituted heteroaryl (e.g. 5 to 10 membered heteroaryl, 5 to 9 membered heteroaryl, or 5 to 6 membered heteroaryl).

In embodiments, R$^{2D}$ is independently oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, R$^{8D}$-substituted or unsubstituted alkyl (e.g. C$_1$-C$_8$ alkyl, C$_1$-C$_6$ alkyl, or C$_1$-C$_4$ alkyl), R$^{8D}$-substituted or unsubstituted heteroalkyl (e.g. 2 to 8 membered heteroalkyl, 2 to 6 membered heteroalkyl, or 2 to 4 membered heteroalkyl), R$^{8D}$-substituted or unsubstituted cycloalkyl (e.g. C$_3$-C$_8$ cycloalkyl, C$_4$-C$_8$ cycloalkyl, or C$_5$-C$_6$ cycloalkyl), R$^{8D}$-substituted or unsubstituted heterocycloalkyl (e.g. 3 to 8 membered heterocycloalkyl, 4 to 8 membered heterocycloalkyl, or 5 to 6 membered heterocycloalkyl), R$^{8D}$-substituted or unsubstituted aryl (e.g. C$_6$-C$_{10}$ aryl or C$_6$ aryl), or R$^{8D}$-substituted or unsubstituted heteroaryl (e.g. 5 to 10 membered heteroaryl, 5 to 9 membered heteroaryl, or 5 to 6 membered heteroaryl).

R$^{8D}$ is independently oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O) NHNH$_2$, —NHC=(O) NH$_2$, —NHSO$_2$H, —NHC=(O)H, —NHC(O)—OH, —NHOH, —OCF$_3$, —OCHF$_2$, R$^{9D}$-substituted or unsubstituted alkyl (e.g. C$_1$-C$_8$ alkyl, C$_1$-C$_6$ alkyl, or C$_1$-C$_4$ alkyl), R$^{9D}$-substituted or unsubstituted heteroalkyl (e.g. 2 to 8 membered heteroalkyl, 2 to 6 membered heteroalkyl, or 2 to 4 membered heteroalkyl), R$^{9D}$-substituted or unsubstituted cycloalkyl (e.g. C$_3$-C$_8$ cycloalkyl, C$_4$-C$_8$ cycloalkyl, or C$_5$-C$_6$ cycloalkyl), R$^{9D}$-substituted or unsubstituted heterocycloalkyl (e.g. 3 to 8 membered heterocycloalkyl, 4 to 8 membered heterocycloalkyl, or 5 to 6 membered heterocycloalkyl), R$^{9D}$-substituted or unsubstituted aryl (e.g. C$_6$-C$_{10}$ aryl or C$_6$ aryl), or R$^{9D}$-substituted or unsubstituted heteroaryl (e.g. 5 to 10 membered heteroaryl, 5 to 9 membered heteroaryl, or 5 to 6 membered heteroaryl).

R$^{9D}$ is independently oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O) NHNH$_2$, —NHC=(O) NH$_2$, —NHSO$_2$H, —NHC=(O)H, —NHC(O)—OH, —NHOH, —OCF$_3$, —OCHF$_2$, R$^{10D}$-substituted or unsubstituted alkyl (e.g. C$_1$-C$_8$ alkyl, C$_1$-C$_6$ alkyl, or C$_1$-C$_4$ alkyl), R$^{10D}$-substituted or unsubstituted heteroalkyl (e.g. 2 to 8 membered heteroalkyl, 2 to 6 membered heteroalkyl, or 2 to 4 membered heteroalkyl), R$^{10D}$-substituted or unsubstituted cycloalkyl (e.g. C$_3$-C$_8$ cycloalkyl, C$_4$-C$_8$ cycloalkyl, or C$_5$-C$_6$ cycloalkyl), R$^{10D}$-substituted or unsubstituted heterocycloalkyl (e.g. 3 to 8 membered heterocycloalkyl, 4 to 8 membered heterocycloalkyl, or 5 to 6 membered heterocycloalkyl), R$^{10D}$-substituted or unsubstituted aryl (e.g. C$_6$-C$_{10}$ aryl or C$_6$ aryl), or R$^{10D}$-substituted or unsubstituted heteroaryl (e.g. 5 to 10 membered heteroaryl, 5 to 9 membered heteroaryl, or 5 to 6 membered heteroaryl).

In embodiments, R$^{3A}$ is independently oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, R$^{11A}$-substituted or unsubstituted alkyl (e.g. C$_1$-C$_8$ alkyl, C$_1$-C$_6$ alkyl, or C$_1$-C$_4$ alkyl), R$^{11A}$-substituted or unsubstituted heteroalkyl (e.g. 2 to 8 membered heteroalkyl, 2 to 6 membered heteroalkyl, or 2 to 4 membered heteroalkyl), R$^{11A}$-substituted or unsubstituted cycloalkyl (e.g. C$_3$-C$_8$ cycloalkyl, C$_4$-C$_8$ cycloalkyl, or C$_5$-C$_6$ cycloalkyl), R$^{11A}$-substituted or unsubstituted heterocycloalkyl (e.g. 3 to 8 membered heterocycloalkyl, 4 to 8 membered heterocycloalkyl, or 5 to 6 membered heterocycloalkyl), R$^{11A}$-substituted or unsubstituted aryl (e.g. C$_6$-C$_{10}$ aryl or C$_6$ aryl), or R$^{11A}$-substituted or unsubstituted heteroaryl (e.g. 5 to 10 membered heteroaryl, 5 to 9 membered heteroaryl, or 5 to 6 membered heteroaryl).

R$^{11A}$ is independently oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O) NHNH$_2$, —NHC=(O) NH$_2$, —NHSO$_2$H, —NHC=(O)H, —NHC(O)—OH, —NHOH, —OCF$_3$, —OCHF$_2$, R$^{12A}$-substituted or unsubstituted alkyl (e.g. C$_1$-C$_8$ alkyl, C$_1$-C$_6$ alkyl, or C$_1$-C$_4$ alkyl), R$^{12A}$-substituted or unsubstituted heteroalkyl (e.g. 2 to 8 membered heteroalkyl, 2 to 6 membered heteroalkyl, or 2 to 4 membered heteroalkyl), R$^{12A}$-substituted or unsubstituted cycloalkyl (e.g. C$_3$-C$_8$ cycloalkyl, C$_4$-C$_8$ cycloalkyl, or C$_5$-C$_6$ cycloalkyl), R$^{12A}$-substituted or unsubstituted heterocycloalkyl (e.g. 3 to 8 membered heterocycloalkyl, 4 to 8 membered heterocycloalkyl, or 5 to 6 membered heterocycloalkyl), R$^{12A}$-substituted or unsubstituted aryl (e.g. $C_6$-$C_{10}$ aryl or $C_6$ aryl), or $R^{12A}$-substituted or unsubstituted heteroaryl (e.g. 5 to 10 membered heteroaryl, 5 to 9 membered heteroaryl, or 5 to 6 membered heteroaryl).

$R^{12A}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{13A}$-substituted or unsubstituted alkyl (e.g. $C_1$-$C_8$ alkyl, $C_1$-$C_6$ alkyl, or $C_1$-$C_4$ alkyl), $R^{13A}$-substituted or unsubstituted heteroalkyl (e.g. 2 to 8 membered heteroalkyl, 2 to 6 membered heteroalkyl, or 2 to 4 membered heteroalkyl), $R^{13A}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{13A}$-substituted or unsubstituted heterocycloalkyl (e.g. 3 to 8 membered heterocycloalkyl, 4 to 8 membered heterocycloalkyl, or 5 to 6 membered heterocycloalkyl), $R^{13A}$-substituted or unsubstituted aryl (e.g. $C_6$-$C_{10}$ aryl or $C_6$ aryl), or $R^{13A}$-substituted or unsubstituted heteroaryl (e.g. 5 to 10 membered heteroaryl, 5 to 9 membered heteroaryl, or 5 to 6 membered heteroaryl).

In embodiments, $R^{3B}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{11B}$-substituted or unsubstituted alkyl (e.g. $C_1$-$C_8$ alkyl, $C_1$-$C_6$ alkyl, or $C_1$-$C_4$ alkyl), $R^{11B}$-substituted or unsubstituted heteroalkyl (e.g. 2 to 8 membered heteroalkyl, 2 to 6 membered heteroalkyl, or 2 to 4 membered heteroalkyl), $R^{11B}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{11B}$-substituted or unsubstituted heterocycloalkyl (e.g. 3 to 8 membered heterocycloalkyl, 4 to 8 membered heterocycloalkyl, or 5 to 6 membered heterocycloalkyl), $R^{11B}$-substituted or unsubstituted aryl (e.g. $C_6$-$C_{10}$ aryl or $C_6$ aryl), or $R^{11B}$-substituted or unsubstituted heteroaryl (e.g. 5 to 10 membered heteroaryl, 5 to 9 membered heteroaryl, or 5 to 6 membered heteroaryl).

$R^{11B}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O) $NHNH_2$, —NHC=(O) $NH_2$, —$NHSO_2H$, —NHC=(O)H, —NHC(O)—OH, —NHOH, —$OCF_3$, —$OCHF_2$, $R^{12B}$-substituted or unsubstituted alkyl (e.g. $C_1$-$C_8$ alkyl, $C_1$-$C_6$ alkyl, or $C_1$-$C_4$ alkyl), $R^{12B}$-substituted or unsubstituted heteroalkyl (e.g. 2 to 8 membered heteroalkyl, 2 to 6 membered heteroalkyl, or 2 to 4 membered heteroalkyl), $R^{12B}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{12B}$-substituted or unsubstituted heterocycloalkyl (e.g. 3 to 8 membered heterocycloalkyl, 4 to 8 membered heterocycloalkyl, or 5 to 6 membered heterocycloalkyl), $R^{12B}$-substituted or unsubstituted aryl (e.g. $C_6$-$C_{10}$ aryl or $C_6$ aryl), or $R^{12B}$—substituted or unsubstituted heteroaryl (e.g. 5 to 10 membered heteroaryl, 5 to 9 membered heteroaryl, or 5 to 6 membered heteroaryl).

$R^{12B}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O) $NHNH_2$, —NHC=(O) $NH_2$, —$NHSO_2H$, —NHC=(O)H, —NHC(O)—OH, —NHOH, —$OCF_3$, —$OCHF_2$, $R^{13B}$-substituted or unsubstituted alkyl (e.g. $C_1$-$C_8$ alkyl, $C_1$-$C_6$ alkyl, or $C_1$-$C_4$ alkyl), $R^{13B}$-substituted or unsubstituted heteroalkyl (e.g. 2 to 8 membered heteroalkyl, 2 to 6 membered heteroalkyl, or 2 to 4 membered heteroalkyl), $R^{13B}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{13B}$-substituted or unsubstituted heterocycloalkyl (e.g. 3 to 8 membered heterocycloalkyl, 4 to 8 membered heterocycloalkyl, or 5 to 6 membered heterocycloalkyl), $R^{13B}$-substituted or unsubstituted aryl (e.g. $C_6$-$C_{10}$ aryl or $C_6$ aryl), or $R^{13B}$-substituted or unsubstituted heteroaryl (e.g. 5 to 10 membered heteroaryl, 5 to 9 membered heteroaryl, or 5 to 6 membered heteroaryl).

In embodiments, $R^3$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{11C}$-substituted or unsubstituted alkyl (e.g. $C_1$-$C_8$ alkyl, $C_1$-$C_6$ alkyl, or $C_1$-$C_4$ alkyl), $R^{11C}$-substituted or unsubstituted heteroalkyl (e.g. 2 to 8 membered heteroalkyl, 2 to 6 membered heteroalkyl, or 2 to 4 membered heteroalkyl), $R^{11C}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{11C}$-substituted or unsubstituted heterocycloalkyl (e.g. 3 to 8 membered heterocycloalkyl, 4 to 8 membered heterocycloalkyl, or 5 to 6 membered heterocycloalkyl), $R^{11C}$-substituted or unsubstituted aryl (e.g. $C_6$-$C_{10}$ aryl or $C_6$ aryl), or $R^{11C}$-substituted or unsubstituted heteroaryl (e.g. 5 to 10 membered heteroaryl, 5 to 9 membered heteroaryl, or 5 to 6 membered heteroaryl).

$R^{11C}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O) $NHNH_2$, —NHC=(O) $NH_2$, —$NHSO_2H$, —NHC=(O)H, —NHC(O)—OH, —NHOH, —$OCF_3$, —$OCHF_2$, $R^{12C}$-substituted or unsubstituted alkyl (e.g. $C_1$-$C_8$ alkyl, $C_1$-$C_6$ alkyl, or $C_1$-$C_4$ alkyl), $R^{12C}$-substituted or unsubstituted heteroalkyl (e.g. 2 to 8 membered heteroalkyl, 2 to 6 membered heteroalkyl, or 2 to 4 membered heteroalkyl), $R^{12C}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{12C}$-substituted or unsubstituted heterocycloalkyl (e.g. 3 to 8 membered heterocycloalkyl, 4 to 8 membered heterocycloalkyl, or 5 to 6 membered heterocycloalkyl), $R^{12C}$-substituted or unsubstituted aryl (e.g. $C_6$-$C_{10}$ aryl or $C_6$ aryl), or $R^{12C}$-substituted or unsubstituted heteroaryl (e.g. 5 to 10 membered heteroaryl, 5 to 9 membered heteroaryl, or 5 to 6 membered heteroaryl).

$R^{12C}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{13C}$-substituted or unsubstituted alkyl (e.g. $C_1$-$C_8$ alkyl, $C_1$-$C_6$ alkyl, or $C_1$-$C_4$ alkyl), $R^{13C}$—Substituted or unsubstituted heteroalkyl (e.g. 2 to 8 membered heteroalkyl, 2 to 6 membered heteroalkyl, or 2 to 4 membered heteroalkyl), $R^{13C}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{13C}$-substituted or unsubstituted heterocycloalkyl (e.g. 3 to 8 membered heterocycloalkyl, 4 to 8 membered heterocycloalkyl, or 5 to 6 membered heterocycloalkyl), $R^{13C}$- substituted or unsubstituted aryl (e.g. $C_6$-$C_{10}$ aryl or $C_6$ aryl), or $R^{13C}$-substituted or unsubstituted heteroaryl (e.g. 5 to 10 membered heteroaryl, 5 to 9 membered heteroaryl, or 5 to 6 membered heteroaryl).

In embodiments, $R^{3D}$ is independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —OCF₃, —OCHF₂, R^{11D}-substituted or unsubstituted alkyl (e.g. $C_1$-$C_8$ alkyl, $C_1$-$C_6$ alkyl, or $C_1$-$C_4$ alkyl), $R^{11D}$-substituted or unsubstituted heteroalkyl (e.g. 2 to 8 membered heteroalkyl, 2 to 6 membered heteroalkyl, or 2 to 4 membered heteroalkyl), $R^{11D}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{11D}$-substituted or unsubstituted heterocycloalkyl (e.g. 3 to 8 membered heterocycloalkyl, 4 to 8 membered heterocycloalkyl, or 5 to 6 membered heterocycloalkyl), $R^{11D}$-substituted or unsubstituted aryl (e.g. $C_6$-$C_{10}$ aryl or $C_6$ aryl), or $R^{11D}$-substituted or unsubstituted heteroaryl (e.g. 5 to 10 membered heteroaryl, 5 to 9 membered heteroaryl, or 5 to 6 membered heteroaryl).

$R^{11D}$ is independently oxo, halogen, —CF₃, —CN, —OH, —NH₂, —COOH, —CONH₂, —NO₂, —SH, —SO₃H, —SO₄H, —SO₂NH₂, —NHNH₂, —ONH₂, —NHC═(O)NHNH₂, —NHC═(O) NH₂, —NHSO₂H, —NHC═(O)H, —NHC(O)—OH, —NHOH, —OCF₃, —OCHF₂, $R^{12D}$- substituted or unsubstituted alkyl (e.g. $C_1$-$C_8$ alkyl, $C_1$-$C_6$ alkyl, or $C_1$-$C_4$ alkyl), $R^{12D}$- substituted or unsubstituted heteroalkyl (e.g. 2 to 8 membered heteroalkyl, 2 to 6 membered heteroalkyl, or 2 to 4 membered heteroalkyl), $R^{12D}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{12D}$-substituted or unsubstituted heterocycloalkyl (e.g. 3 to 8 membered heterocycloalkyl, 4 to 8 membered heterocycloalkyl, or 5 to 6 membered heterocycloalkyl), $R^{12D}$-substituted or unsubstituted aryl (e.g. $C_6$-$C_{10}$ aryl or $C_6$ aryl), or $R^{12D}$-substituted or unsubstituted heteroaryl (e.g. 5 to 10 membered heteroaryl, 5 to 9 membered heteroaryl, or 5 to 6 membered heteroaryl).

$R^{12D}$ is independently oxo, halogen, —CF₃, —CN, —OH, —NH₂, —COOH, —CONH₂, —NO₂, —SH, —SO₃H, —SO₄H, —SO₂NH₂, —NHNH₂, —ONH₂, —NHC═(O)NHNH₂, —NHC═(O) NH₂, —NHSO₂H, —NHC═(O)H, —NHC(O)—OH, —NHOH, —OCF₃, —OCHF₂, $R^{13D}$-substituted or unsubstituted alkyl (e.g. $C_1$-$C_8$ alkyl, $C_1$-$C_6$ alkyl, or $C_1$-$C_4$ alkyl), $R^{13D}$- substituted or unsubstituted heteroalkyl (e.g. 2 to 8 membered heteroalkyl, 2 to 6 membered heteroalkyl, or 2 to 4 membered heteroalkyl), $R^{13D}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{13D}$-substituted or unsubstituted heterocycloalkyl (e.g. 3 to 8 membered heterocycloalkyl, 4 to 8 membered heterocycloalkyl, or 5 to 6 membered heterocycloalkyl), $R^{13D}$-substituted or unsubstituted aryl (e.g. $C_6$-$C_{10}$ aryl or $C_6$ aryl), or $R^{13D}$-substituted or unsubstituted heteroaryl (e.g. 5 to 10 membered heteroaryl, 5 to 9 membered heteroaryl, or 5 to 6 membered heteroaryl).

$R^7$, $R^{7A}$, $R^{7B}$, $R^{7C}$, $R^{7D}$, $R^{10}$, $R^{10A}$, $R^{10B}$, $R^{10C}$, $R_{10D}$, $R^{12}$, $R^{13A}$, $R^{13B}$, $R^{13C}$, $R^{13D}$, are independently oxo, halogen, —CF₃, —CN, —OH, —NH₂, —COOH, —CONH₂, —NO₂, —SH, —SO₃H, —SO₄H, —SO₂NH₂, —NHNH₂, —ONH₂, —NHC═(O)NHNH₂, —NHC═(O) NH₂, —NHSO₂H, —NHC═(O)H, —NHC(O)—OH, —NHOH, —OCF₃, —OCHF₂, unsubstituted alkyl (e.g. $C_1$-$C_8$ alkyl, $C_1$-$C_6$ alkyl, or $C_1$-$C_4$ alkyl), unsubstituted heteroalkyl (e.g. 2 to 8 membered heteroalkyl, 2 to 6 membered heteroalkyl, or 2 to 4 membered heteroalkyl), unsubstituted cycloalkyl (e.g. $C_3$-$C_8$ cycloalkyl, $C_4$-$C_8$ cycloalkyl, or $C_5$-$C_6$ cycloalkyl), unsubstituted heterocycloalkyl (e.g. 3 to 8 membered heterocycloalkyl, 4 to 8 membered heterocycloalkyl, or 5 to 6 membered heterocycloalkyl), unsubstituted aryl (e.g. $C_6$-$C_{10}$ aryl or $C_6$ aryl), or unsubstituted heteroaryl (e.g. 5 to 10 membered heteroaryl, 5 to 9 membered heteroaryl, or 5 to 6 membered heteroaryl).

In embodiments, n1 is 0. In embodiments, n1 is 1. In embodiments, n1 is 2. In embodiments, n1 is 3. In embodiments, n1 is 4. In embodiments, m1 is 1. In embodiments, m1 is 2. In embodiments, v1 is 1. In embodiments, v1 is 2.

In embodiments, $X^{1.1}$ is —Cl. In embodiments, $X^{1.1}$ is —Br. In embodiments, $X^{1.1}$ is —I. In embodiments, $X^{1.1}$ is —F. In embodiments, $X^{2.1}$ is —Cl. In embodiments, $X^{2.1}$ is —Br. In embodiments, $X^{2.1}$ is —I. In embodiments, $X^{2.1}$ is —F. In embodiments, $X^{3.1}$ is —Cl. In embodiments, $X^{3.1}$ is —Br. In embodiments, $X^{3.1}$ is —I. In embodiments, $X^{3.1}$ is —F.

II. Methods

In a first aspect, there is provided a method for labeling a nucleic acid. The method includes contacting a nucleic acid including native nucleobases with a transglycosylase and a nucleoside derivative under conditions suitable to exchange at least one of the native nucleobases for the nucleoside derivative, thereby providing a labeled nucleic acid.

In embodiments, the nucleic acid is RNA. In embodiments, the nucleic acid is DNA.

In embodiments, the Transglycosylase bacterial tRNA Guanine Transglycosylase (TGT). In embodiments, the nucleic acid is DNA, and the nucleoside derivative is deoxyuridine.

In embodiments, the nucleoside derivative is an analog of PreQ1, with structure following:

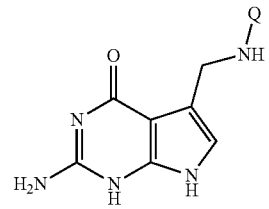

with the proviso that Q is not hydrogen.

In embodiments, Q is —L¹—L²—R³. L¹, L² and R³ are as described herein.

In embodiments, the nucleoside derivative has the structure of Formula (I)

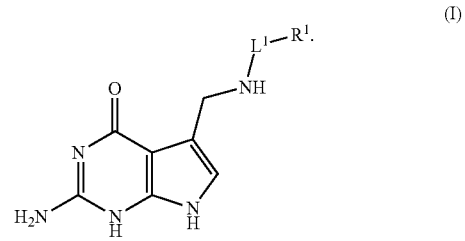

(I)

Regarding Formula (I), $L^1$ is a divalent linking moiety; and $R^1$ is a labeling moiety.

In embodiments, $L^1$ is a bond, —C(O)—, —C(O)O—, —C(O)NR⁷—, —O—, —S(O)$_n$—, —S(O)NR⁷—, —C(O)NR⁷S(O)₂—, substituted or unsubstituted alkylene, or substituted or unsubstituted heteroalkylene, substituted or unsubstituted cycloalkylene, substituted or unsubstituted heterocycloalkylene, substituted or unsubstituted arylene, or substituted or unsubstituted heteroarylene. $R^7$ is independently hydrogen, halogen, —N₃, —NO₂, —CF₃, —CCl₃, —CBr₃, —Cl₃, —CN, —OH, —NH₂, —COOH, —CONH₂, —NO₂, —SH, —SO₂Cl, —SO₃H, —SO₂Ph, —SO$_2$NH$_2$, —NHNH$_2$, —ONH$_2$, —OCH$_3$, —NHCNHNH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, n is 0, 1, or 2.

In embodiments, R$^1$ is substituted or unsubstituted alkyl, substituted or unsubstituted alkenyl, substituted or unsubstituted alkynyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, R$^1$ includes an alkyne, azide, cyclopropene, trancyclooctene, and/or tetrazine moiety, or other reactive moiety, as known in the art. In emboidments, R$^1$ includes a fluorogenic compound. In embodiments, the nucleobase derivative provides an affinity label (e.g., biotin). In embodiments, R$^1$ includes a fluorophore.

In embodiments, the nucleobase derivative is an N-alkyl analog of PreQ1 wherein L$^1$ is alkylene, e.g., N-ethyl PreQ1,:

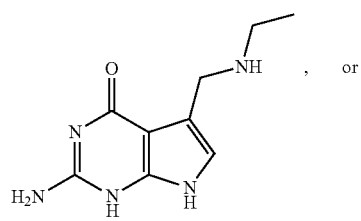

or

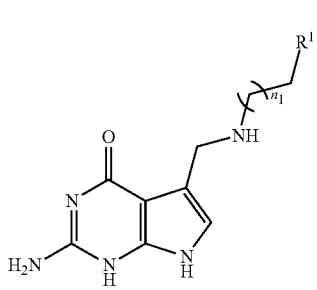

wherein n$_1$ is an integer in the range 0 to 19. In embodiments, the nucleobase derivative is an N-alkyne PreQ1, e.g.,

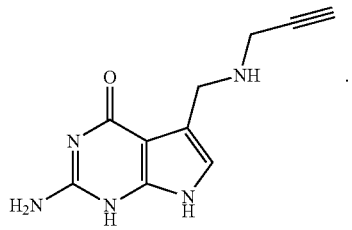 [SMILES: C#CCNCc1c[nH]c2[nH]c(N)nc(=O)c12]

In embodiments, the nucleobase derivative incorporates a polyethyleneglycol (PEG) linker:

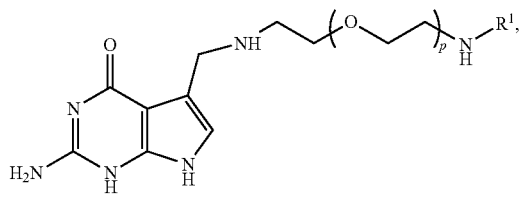

wherein "p" is the number of PEG units (e.g., PEG$_3$). In embodiments, the nucleobase derivative is PreQ1-PEG$_2$-Boc or PreQ1-PEG$_2$—NH$_2$:

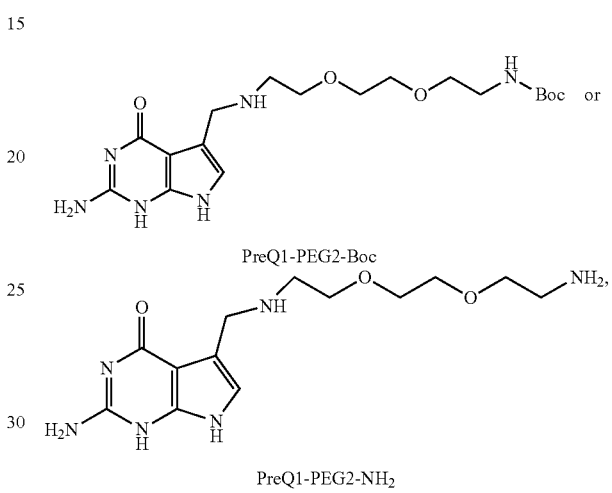

PreQ1-PEG2-Boc

PreQ1-PEG2-NH$_2$ respectively. In embodiments, the nucleobase derivative is PreQ1-PEG2-amine further bound to lab el R$^1$:

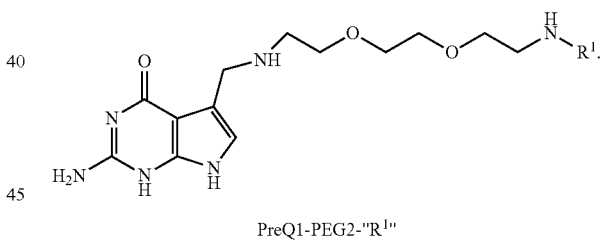

PreQ1-PEG2-"R$^1$"

In embodiments, the nucleobase derivative is PreQ1-PEG$_3$-Boc, PreQ1-PEG$_3$-amine, or PreQ1-PEG$_3$-R$^1$:

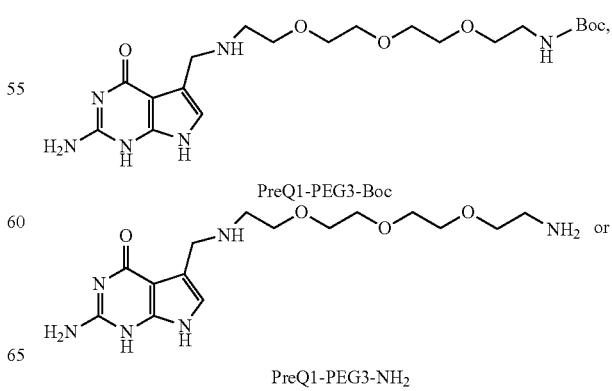

PreQ1-PEG3-Boc or

PreQ1-PEG3-NH$_2$

-continued

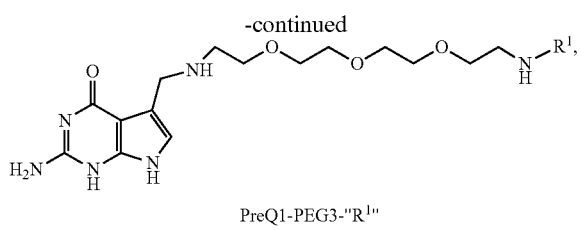

PreQ1-PEG3-"R¹'"

respectively.

In embodiments, R¹ is biotin:

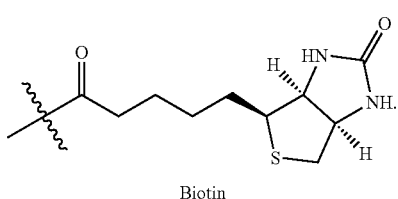 [SMILES: *C(=O)CCCC[C@@H]1SC[C@@H]2NC(=O)N[C@@H]21]

Biotin

In embodiments, R1 is AlexaFluor-488 or thiazole orange:

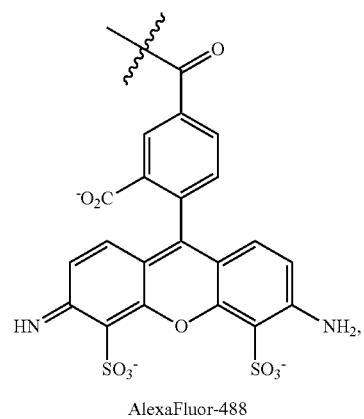

AlexaFluor-488

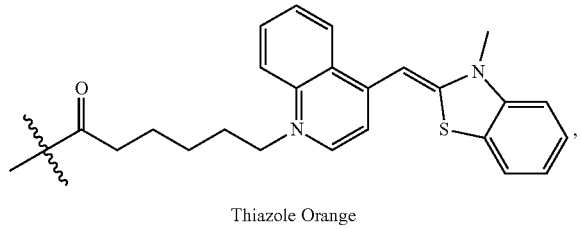

Thiazole Orange respectively.

In embodiments, the transglycosylase is encoded in a vector suitable for administration to a subject for incorporation into a cell and expression of the transglycosylase.

In another aspect, provided herein is a method a method of substituting a guanine with a PreQ1 analog within an RNA molecule. The method includes contacting a PreQ1 analog with an RNA molecule in the presence of a transglycosylase; and allowing the transglycosylase to substitute a guanine moiety from a guanine within the RNA sequence with the PreQ1 analog thereby forming a modified RNA molecule.

In embodiments, the transglycosylase is eukaryotic. In embodiments, the transglycosylase is prokaryotic. In embodiments, the transglycosylase is bacterial. In embodiments, the transglycosylase is $E.\ coli$ transglycosylase. In embodiments, the transglycosylase is from a $shigella$ strain. In embodiments, the transglycosylase is from a $salmonella$ strain. In embodiments, the transglycosylase is from $Z.\ mobilis$.

The contacting may be performed in vitro. The contacting may be performed in vivo. In embodiments, the guanine is within a hairpin loop in the RNA molecule. In embodiments, the guanine is in a 5' UGU 3' sequence, a 5' YGU 3' sequence or a 5' UGY 3' sequence within the RNA molecule, wherein Y is a nucleotide or pseudouridine. In other embodiments, the guanine is in a 5' UGU 3' sequence within a hairpin loop in the RNA molecule. In further embodiments, the RNA molecule comprises a plurality of hairpin elements. In embodiments, the RNA molecule comprises modified nucleobase. In embodiments, the RNA molecule comprises a sequence as set forth in SEQ ID NO:5 or SEQ ID NO:6. In embodiments, the cell is a eukaryotic cell. In embodiments, the cell is a prokaryotic cell. In embodiments, the cell is a bacterial cell. In embodiments, the transglycosylase is bacterial transglycosylase.

Provided herein is a method of screening for a transglycosylase inhibitor. The method comprises contacting a detectable PreQ1 with an RNA molecule in the presence of a transglycosylase and a test transglycosylase inhibitor; and determining whether the transglycosylase substitutes a guanine moiety from a guanine within the RNA molecule with the detectable PreQ1 analog.

In embodiments, the test transglycosylase inhibitor is a small molecule or a biomolecule. In embodiments, the biomolecule is a polypeptide, a protein, an antibody or a nucleic acid molecule. In embodiments, the small molecule is an organic molecule. In embodiments, the small molecule is an organic molecule having a molecular weight of 900 Da or less. In embodiments, the determining comprises detecting substitution of the guanine moiety from the guanine within the RNA sequence with the PreQ1 analog thereby identifying a transglycosylase inhibitor. In embodiments, the detecting comprises determination of fluorescence emission intensity.

In embodiments, the PreQ1 analog is a compound of Formula (IIa):

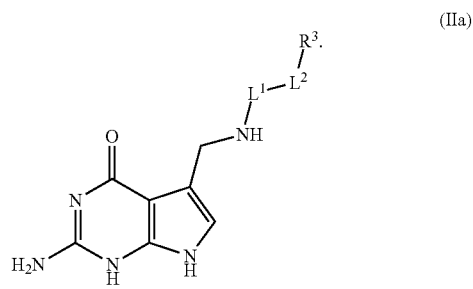

(IIa)

n1, m1, v1, $L^1$, $L^2$ and $R^3$ are as described herein.

In embodiments, $L^1$ is substituted or unsubstituted unbranched alkylene or substituted or unsubstituted unbranched heteroalkylene. In embodiments, $L^1$ is a substituted or unsubstituted PEG linker.

In some embodiments, $R^3$ is a biomolecule. In some embodiments, $R^3$ is a dye, a fluorophore, an antibody, a polypeptide, a protein, a nucleic acid molecule, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, R³ is thiazole orange or a derivative thereof. In embodiments, R³ is biocytin, biotin, a boron-dipyrromethene dye or a cyanine dye. In some embodiments, R³ contains a tetrazine moeity. In embodiments, R³ contains a terminal or strained alkyne moiety. In embodiments, R³ contains a (E)-Cyclooct-4-enol (TCO) moiety.

Disclosed herein, are methods and reagents for the incorporation of unnatural residues (e.g., nucleoside derivatives such as PreQ1 analogs and the like) bearing bioorthogonal handles, fluorophores, and other groups to be incorporated into a nucleic acid (e.g., RNA stem loop from bacterial Tyrosine tRNA site) specifically replacing the Guanine at the wobble position with a nucleobase derivative (e.g., preQ1 and derivatives thereof). This transglycosylation reaction can be carried out by a transglycosylase (e.g., bacterial (*E. coli*) tRNA Guanine Transglycosylase (TGT) whose natural substrate is the small molecule PreQ1). By extending alkyl chains bearing functional groups off of the exocyclic primary amine of PreQ1, these unnatural bases can be successfully incorporated by the TGT enzyme into the tRNA recognition stem loop with comparable efficiency to that of the natural substrate. This allows incorporation of an alkyl amine derivative of preQ1, which can utilize a variety of linkers (e.g., PEG linkers) with bioorthogonal ligation partners, fluorogenic dyes, and affinity labels such as biotin.

The methods and reagents disclosed herein are for site-specific replacement of the natural nucleoside (e.g., guanine) with an unnatural nucleobase (derivatized with biomolecules of interest) within a nucleic acid (e.g., a short recognition sequence of RNA) by utilizing an enzymatic transglycosylase enzymatic reaction (e.g., catalyzed by *E. coli* TGT). Applications exist both in vitro and in vivo through genetic incorporation of a small RNA recognition sequence into coded RNAs of interest to be able to detect the presence of (and quantify), track the location of, and/or isolate labeled RNA through appended chemical probes covalently linked through a post-transcriptional enzymatic reaction by the TGT enzyme with substrates of choice. This particular enzyme TGT provides a platform for a wide variety of labeling applications. For example, this enzymatic reaction can be utilized to label a naturally transcribed RNA containing the *E. coli* TGT recognition hairpin to detect and visually localize the RNA through a PreQ1 analog with an appended fluorogenic probe joined through a PEG or short alkyl linker, the fluorescence of which would greatly increase upon adjacent intercalation of the probe with the RNA hairpin structure.

Thiazole Orange (TO) is one such fluorophore that would naturally exhibit this property. Fluorogenic probes containing a fluorophore (e.g., TO) can be useful to identify inhibitors. Further applications include the ability to "pull down" or "fish out" RNA of interest through incorporation of a biotin modified preQ1 for the purposes of RNA quantitation and isolation. Additionally this enzymatic reaction can be used in the incorporation of bioorthogonal covalent labeling partners such as alkynes, azides, cyclopropenes, trancyclooctenes, and tetrazines. We can further investigate RNA-protein interactions by appending known protein allosteric inhibitors to interacting encoded RNAs for the purposes of probing RNA-protein interactions.

The structure of PreQ1 follows:

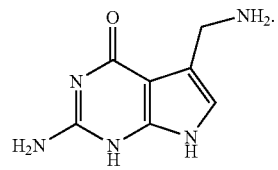 [SMILES: NCc1c[nH]c2[nH]c(N)nc(=O)c12]

Exemplary of the methods disclosed here, the transglycosylation labeling reaction of a substrate tRNA stem loop can be carried out by incubation in a suitable buffer system with target RNA, PreQ1 analog and TGT enzyme (for in vitro applications) or by expression of the TGT enzyme within mammalian cells and exogenous addition of the PreQ1 analog substrate for incubation and incorporation into the genetically encoded and endogenously expressed RNA containing the target recognition sequence (for in vivo applications). Structure activity relationship assays as well as crystallographic data indicate that a key catalytic aspartate residue covalently links the RNA substrate to the enzyme thereby freeing guanine from the RNA polymer by breaking the glycosidic bond. In a second step guanine is replaced by the PreQ1 analog and the catalytic aspartate residue transfers the RNA polymer's sugar to the PreQ1 analog effectively completing the transglycosylation. Crystallographic data indicates room for derivitization off of the primary amine of preQ1 and mutations can allow for a wider substrate scope with high catalytic efficiency. Optimization of Polyethylene glycol (PEG) linkers, or alkyl, alkenyl, or alkynyl linkers of various lengths with appended chemistries can allow for successful incorporation of any biomolecule of choice. These derivatives can be made by simple $S_N2$ chemistry to yield the secondary amines desired. Crystallographic data indicates hydrogen bond contacts between the primary amine of PreQ1 and the protein. Further work has shown lack of amine at that position reduces or abolishes substrate binding. It therefore seems important that the secondary amine remain intact for adequate substrate binding.

Fluorogenic probes for RNA detection can be employed, e.g., through the use of an appended Thiazole Orange (TO) derivative. TO has been well established in the literature to demonstrate significant "turn-on" fluorescence upon intercalation into duplexed nucleotides. We therefore can covalently link this fluorophore to the RNA and through a flexible PEG or other linker allow for intra-molecular interactions of the fluorophore with the RNA recognition stem loop hairpin to elicit a turn on fluorescent response once covalently linked.

Thus, uses for the resulting labeled nucleic acids include: RNA labeling and visualization agents in live cells; super-resolution imaging of transcribed RNAs in live cells; RNA screening and quantitation assays for drug discovery and development; RNA screening and quantitation assays for disease states and analysis; RNA pull down assays for drug discovery and disease state analysis; and the like.

Embodiments

Embodiments disclosed herein include embodiments P1 to P7 following.

Embodiment P1. A method for labeling a nucleic acid, said method comprising: contacting a nucleic acid comprising native nucleobases with a transglycosylase and a nucleoside derivative under conditions suitable to exchange at least one said native nucleobases for said nucleoside derivative.

Embodiment P2. The method of embodiment P1, wherein said nucleic is RNA.

Embodiment P3. The method of embodiment P1, wherein said nucleic is DNA

Embodiment P4. The method of embodiment P1, wherein said transglycosylase is bacterial tRNA Guanine Transglycosylase (TGT).

Embodiment P5. The method of embodiment P1, wherein said nucleoside derivative has the structure of Formula (I):

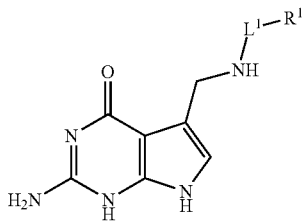

wherein $L^1$ is a divalent linking moiety; and $R^1$ is a labeling moiety.

Embodiment P6. The method of embodiment P5, wherein $L^1$ is a bond, —C(O)—, —C(O)O—, —C(O)NR$^7$—, —O—, —S(O)$_n$—, —S(O)NR$^7$—,—C(O)NR$^7$S(O)$_2$—, substituted or unsubstituted alkylene, or substituted or unsubstituted heteroalkylene, substituted or unsubstituted cycloalkylene, substituted or unsubstituted heterocycloalkylene, substituted or unsubstituted arylene, or substituted or unsubstituted heteroarylene; $R^7$ is independently hydrogen, halogen, —N$_3$, —NO$_2$, —CF$_3$, —CCl$_3$, —CBr$_3$, —CI$_3$, —CN, —OH, —NH$_2$, —COOH, —CONH$_2$, —NO$_2$, —SH, —SO$_2$Cl, —SO$_3$H, —SO$_2$Ph, —SO$_2$NH$_2$, —NHNH$_2$, —ONH$_2$, —OCH$_3$, —NHCNHNH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and n is 0, 1, or 2.

Embodiment P7. The method of embodiment P5, wherein $R^1$ is substituted or unsubstituted alkyl, substituted or unsubstituted alkenyl, substituted or unsubstituted alkynyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiments disclosed herein include embodiments Q1 to Q10 following.

Embodiment Q1. A method for labeling a nucleic acid, said method comprising: contacting a nucleic acid comprising native nucleobases with a transglycosylase and a nucleoside derivative under conditions suitable to exchange at least one said native nucleobases for said nucleoside derivative.

Embodiment Q2. The method of embodiment Q1, wherein said nucleic is RNA.

Embodiment Q3. The method of embodiment Q1, wherein said nucleic is DNA

Embodiment Q4. The method of embodiment Q1, wherein said transglycosylase is bacterial tRNA Guanine Transglycosylase (TGT).

Embodiment Q5. The method of embodiment Q1, wherein said nucleoside derivative has the structure of Formula (I):

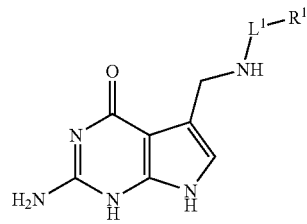

wherein $L^1$ is a divalent linking moiety; and $R^1$ is a labeling moiety.

Embodiment Q6. The method of embodiment Q5, wherein $L^1$ is a bond, —C(O)—, —C(O)O—, —C(O)NR$^7$—, —O—, —S(O)$_n$—, —S(O)NR$^7$—,—C(O)NR$^7$S(O)$_2$—, substituted or unsubstituted alkylene, or substituted or unsubstituted heteroalkylene, substituted or unsubstituted cycloalkylene, substituted or unsubstituted heterocycloalkylene, substituted or unsubstituted arylene, or substituted or unsubstituted heteroarylene; $R^7$ is independently hydrogen, halogen, —N$_3$, —NO$_2$, —CF$_3$, —CCl$_3$, —CBr$_3$, —CI$_3$, —CN, —OH, —NH$_2$, —COOH, —CONH$_2$, —NO$_2$, —SH, —SO$_2$Cl, —SO$_3$H, —SO$_2$Ph, —SO$_2$NH$_2$, —NHNH$_2$, —ONH$_2$, —OCH$_3$, —NHCNHNH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and n is 0, 1, or 2.

Embodiment Q7. The method of embodiment Q5, wherein $R^1$ is substituted or unsubstituted alkyl, substituted or unsubstituted alkenyl, substituted or unsubstituted alkynyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment Q8. A compound with structure of Formula (I):

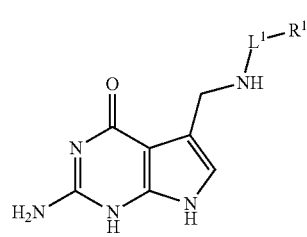

wherein $L^1$ is a divalent linking moiety; and $R^1$ is a labeling moiety.

Embodiment Q9. The compound of embodiment Q8, wherein $L^1$ is a bond, —C(O)—, —C(O)O—, —C(O)NR$^7$—, —O—, —S(O)$_n$—, —S(O)NR$^7$—,—C(O)NR$^7$S(O)$_2$—, substituted or unsubstituted alkylene, or substituted or unsubstituted heteroalkylene, substituted or unsubstituted cycloalkylene, substituted or unsubstituted heterocycloalkylene, substituted or unsubstituted arylene, or substituted or unsubstituted heteroarylene; $R^7$ is independently hydrogen, halogen, —N$_3$, —NO$_2$, —CF$_3$, —CCl$_3$, —CBr$_3$, —CI$_3$, —CN, —OH, —NH$_2$, —COOH, —CONH$_2$, —NO$_2$, —SH, —SO$_2$Cl , —SO$_3$H, —SO$_2$Ph, —SO$_2$NH$_2$, —NHNH$_2$, —ONH$_2$, —OCH$_3$, —NHCNHNH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and n is 0, 1, or 2.

Embodiment Q10. The compound of embodiment Q8, wherein $R^1$ is substituted or unsubstituted alkyl, substituted or unsubstituted alkenyl, substituted or unsubstituted alkynyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment Q11. A method of producing a labeled RNA, the method comprising contacting a compound according to claim 8 with an RNA fragment under conditions suitable for incorporation the compound into the RNA fragment, thereby affording a labeled RNA Further embodiments include embodiments 12 to 43 following.

Embodiment 12. A compound of structural Formula II:

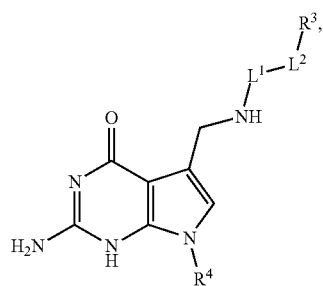

II or a salt thereof, wherein: $L^1$ is a bond, substituted or unsubstituted alkylene or substituted or unsubstituted heteroalkylene, a detectable moiety, $-CX^{1.1}_3$, $-CHX^{1.1}_2$, $-CH_2X^{1.1}$, $-CN$, $-SO_{n1}R^{1A}$, $-SO_{v1}NR^{1B}R^{1C}$, $-NHNR^{1B}R^{1C}$, $-ONR^{1B}R^{1C}$, $-NHC(O)NHNR^{1B}R^{1C}$, $-NHC(O)NR^{1B}R^{1C}$, $-N(O)_{m1}$, $-NR^{1B}R^{1C}$, $-C(O)R^{1D}$, $-C(O)OR^{1D}$, $-C(O)NR^{1B}R^{1C}$, $-OR^{1A}$, $-NR^{1B}SO_2R^{1A}$, $-NR^{1B}C(O)R^{1D}$, $-NR^{1B}C(O)OR^{1D}$, $-NR^{1B}OR^{1D}$, $-OCX^{1.1}_3$, $-OCHX^{1.1}_2$, substituted or unsubstituted cycloalkylene, substituted or unsubstituted heterocycloalkylene, substituted or unsubstituted arylene, or substituted or unsubstituted heteroarylene; $L^2$ is a bond, substituted or unsubstituted alkylene or substituted or unsubstituted heteroalkylene, a detectable moiety, $-CX^{2.1}_3$, $-CHX^{2.1}_2$, $-CH_2X^{2.1}$, $-CN$, $-SO_{n1}R^{2A}$, $-SO_{v1}NR^{2B}R^{2C}$, $-NHNR^{2B}R^{2C}$, $-ONR^{2B}R^{2C}$, $-NHC(O)NHNR^{2B}R^{2C}$, $-NHC(O)NR^{2B}R^{2C}$, $-N(O)_{m1}$, $-NR^{2B}R^{2C}$, $-C(O)R^{2D}$, $-C(O)OR^{2D}$, $-C(O)NR^{2B}R^{2C}$, $-OR^{2A}$, $-NR^{2B}SO_2R^{2A}$, $-NR^{2B}C(O)R^{2D}$, $-NR^{2B}C(O)OR^{2D}$, $-NR^{2B}OR^{2D}$, $-OCX^{2.1}_3$, $-OCHX^{2.1}_2$, substituted or unsubstituted cycloalkylene, substituted or unsubstituted heterocycloalkylene, substituted or unsubstituted arylene, or substituted or unsubstituted heteroarylene; n1 is an integer from 0 to 4; m1 and v1 are independently 1 or 2; $R^3$ is a detectable moiety, a biomolecule, hydrogen, halogen, $-CX^{3.1}_3$, $-CHX^{3.1}_2$, $-CH_2X^{3.1}$, $-CN$, $-SO_{n1}R^{3A}$, $-SO_{v1}NR^{3B}R^{3C}$, $-NHNR^{3B}R^{3C}$, $-ONR^{3B}R^{3C}$, $-NHC(O)NHNR^{3B}R^{3C}$, $-NHC(O)NR^{3B}R^{3C}$, $-N(O)_{m1}$, $-NR^{3B}R^{3C}$, $-C(O)R^{3D}$, $-C(O)OR^{3D}$, $-C(O)NR^{3B}R^{3C}$, $-OR^{3A}$, $-NR^{3B}SO_2R^{3A}$, $-NR^{3B}C(O)R^{3D}$, $-NR^{3B}C(O)OR^{3D}$, $-NR^{3B}OR^{3D}$, $-OCX^{3.1}_3$, $-OCHX^{3.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^4$ is hydrogen or a ribose, wherein the ribose is part of a modified or unmodified RNA molecule, and further wherein the ribose comprises a guanine; $R^{1A}$, $R^{1B}$, $R^{1C}$, $R^{1D}$, $R^{2A}$, $R^{2B}$, $R^{2C}$, $R^{3D}$, $R^{3A}$, $R^{3B}$, $R^{3C}$ and $R^{3D}$ are independently hydrogen, halogen, $-CF_3$, $-CCl_3$, $-CBr_3$, $-CI_3$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)-OH$, $-NHOH$, $-OCF_3$, $-OCCl_3$, $-OCBr_3$, $-OCI_3$, $-OCHF_2$, $-OCHCl_2$, $-OCHBr_2$, $-OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1B}$, $R^{1C}$, $R^{2B}$, $R^{2C}$, $R^{3B}$ and $R^{3C}$ substituents bonded to the same nitrogen atom may optionally be joined to form a substituted or unsubstituted heterocycloalkyl or substituted or unsubstituted heteroaryl; and $X^{1.1}$, $X^{2.1}$ and $X^{3.1}$ are independently $-Cl$, $-Br$, $-I$ or $-F$.

Embodiment 13. The compound of embodiment 12, wherein $L^1$ is substituted or unsubstituted unbranched alkylene or substituted or unsubstituted unbranched heteroalkylene.

Embodiment 14. The compound of embodiment 12, wherein $L^1$ is substituted or unsubstituted unbranched $C_4$-$C_{12}$ alkylene.

Embodiment 15. The compound of embodiment 12, wherein $R^4$ is hydrogen.

Embodiment 16. The compound of embodiment 12, wherein $R^4$ is a ribose.

Embodiment 17. The compound of embodiment 12, wherein $R^3$ is a dye, a fluorophore, an affinity ligand, an antibody, a biomolecule, a polypeptide, a protein or a nucleic acid molecule.

Embodiment 18. The compound of embodiment 12, wherein the guanine forms part of a 5' YGU 3' sequence or a 5' UGY 3' sequence within the RNA molecule, wherein Y is a nucleotide or pseudouridine.

Embodiment 19. The compound of embodiment 12, wherein the guanine forms part of a 5' UGU 3' within the RNA molecule.

Embodiment 20. The compound of embodiment 19, wherein the 5' UGU 3' sequence is within an RNA hairpin element.

Embodiment 21. The compound of embodiment 20, wherein the 5' UGU 3' sequence is located in the loop of the hairpin.

Embodiment 22. The compound of embodiment 12, wherein the guanine forms part of a 5' ψGψ 3' sequence within the RNA molecule.

Embodiment 23. The compound of embodiment 12, wherein $R^3$ is biocytin, biotin, a boron-dipyrromethene dye, a cyanine dye, a thiazole compound or a thiazole orange derivative.

Embodiment 24. The compound of embodiment 12, wherein the RNA molecule comprises a 5-methylcytosine, a pseudouridine (ψ), a 2-thiouridine or any combination thereof.

Embodiment 25. A method of substituting a guanine with a PreQ1 analog within an RNA molecule, comprising contacting a PreQ1 analog with an RNA molecule in the presence of a transglycosylase; and (ii) allowing the transglycosylase to substitute a guanine moiety from a guanine within the RNA sequence with the PreQ1 analog thereby forming a modified RNA molecule.

Embodiment 26. The method of embodiment 25, wherein the guanine is within a hairpin loop in the RNA molecule.

Embodiment 27. The method of embodiment 25, wherein the guanine is in a 5' UGU 3' sequence, a 5' YGU 3' sequence or a 5' UGY 3' sequence within the RNA molecule, wherein Y is a nucleotide or pseudouridine.

Embodiment 28. The method of embodiment 25, wherein the guanine is in a 5' UGU 3' sequence within a hairpin loop in the RNA molecule.

Embodiment 29. The method of embodiment 25, wherein the RNA molecule comprises a plurality of hairpin elements.

Embodiment 30. The method of embodiment 25, wherein the RNA molecule comprises modified nucleobase.

Embodiment 31. The method of embodiment 25, wherein the RNA molecule comprises a sequence as set forth in SEQ ID NO:5 or SEQ ID NO:6.

Embodiment 32. A method of screening for a transglycosylase inhibitor comprising: contacting a detectable PreQ1 with an RNA molecule in the presence of a transglycosylase and a test transglycosylase inhibitor; and (ii) determining whether the transglycosylase substitutes a guanine moiety from a guanine within the RNA molecule with the detectable PreQ1 analog.

Embodiment 33. The method of embodiment 32, wherein the test transglycosylase inhibitor is a small molecule or a biomolecule.

Embodiment 34. The method of embodiment 33, wherein the biomolecule is a polypeptide, a protein, an antibody or a nucleic acid molecule.

Embodiment 35. The method of embodiment 33, wherein the small molecule is an organic molecule.

Embodiment 36. The method of embodiment 35, wherein the organic molecule has a molecular weight of 900 Da or less.

Embodiment 37. The method of embodiment 32, wherein the determining comprises detecting substitution of the guanine moiety from the guanine within the RNA sequence with the PreQ1 analog thereby identifying a transglycosylase inhibitor.

Embodiment 38. The method of embodiment 37, wherein the detecting comprises determination of fluorescence emission intensity.

Embodiment 39. The method of any one of embodiments 25 to 38, wherein the PreQ1 analog is a compound of Formula (IIa):

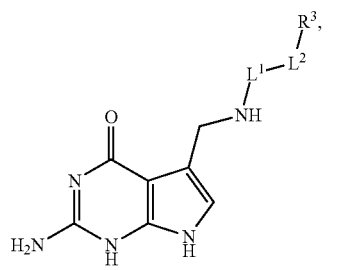

(IIa)

wherein: $L^1$ is a bond, substituted or unsubstituted alkylene or substituted or unsubstituted heteroalkylene, a detectable moiety, $-CX^{1.1}_3$, $-CHX^{1.1}_2$, $-CH_2X^{1.1}$, $-CN$, $-SO_{n1}R^{1A}$, $-SO_{v1}NR^{1B}R^{1C}$, $-NHNR^{1B}R^{1C}$, $-ONR^{1B}R^{1C}$, $-NHC(O)NHNR^{1B}R^{1C}$, $-NHC(O)NR^{1B}R^{1C}$, $-N(O)_{m1}$, $-NR^{1B}R^{1C}$, $-C(O)R^{1D}$, $-C(O)OR^{1D}$, $-C(O)NR^{1B}R^{1C}$, $-OR^{1A}$, $-NR^{1B}SO_2R^{1A}$, $-NR^{1B}C(O)R^{1D}$, $-NR^{1B}C(O)OR^{1D}$, $-NR^{1B}OR^{1D}$, $-OCX^{1.1}_3$, $-OCHX^{1.1}_2$, substituted or unsubstituted cycloalkylene, substituted or unsubstituted heterocycloalkylene, substituted or unsubstituted arylene, or substituted or unsubstituted heteroarylene; $L^2$ is a bond, substituted or unsubstituted alkylene or substituted or unsubstituted heteroalkylene, a detectable moiety, $-CX^{2.1}_3$, $-CHX^{2.1}_2$, $-CH_2X^{2.1}$, $-CN$, $-SO_{n1}R^{2A}$, $-SO_{v1}NR^{2B}R^{2C}$, $-NHNR^{2B}R^{2C}$, $-ONR^{2B}R^{2C}$, $-NHC(O)NHNR^{2B}R^{2C}$, $-NHC(O)NR^{2B}R^{2C}$, $-N(O)_{m1}$, $-NR^{2B}R^{2C}$, $-C(O)R^{2D}$, $-C(O)OR^{2D}$, $-C(O)NR^{2B}R^{2C}$, $-OR^{2A}$, $-NR^{2B}SO_2R^{2A}$, $-NR^{2B}C(O)R^{2D}$, $-NR^{2B}C(O)OR^{2D}$, $-NR^{2B}OR^{2D}$, $-OCX^{2.1}_3$, $-OCHX^{2.1}_2$, substituted or unsubstituted cycloalkylene, substituted or unsubstituted heterocycloalkylene, substituted or unsubstituted arylene, or substituted or unsubstituted heteroarylene; n1 is an integer from 0 to 4; m1 and v1 are independently 1 or 2; $R^3$ is a detectable moiety, a biomolecule, hydrogen, halogen, $-CX^{3.1}_3$, $-CHX^{3.1}_2$, $-CH_2X^{3.1}$, $-CN$, $-SO_{n1}R^{3A}$, $-SO_{v1}NR^{3B}R^{3C}$, $-NHNR^{3B}R^{3C}$, $-ONR^{3B}R^{3C}$, $-NHC(O)NHNR^{3B}R^{3C}$, $-NHC(O)NR^{3B}R^{3C}$, $-N(O)_{m1}$, $-NR^{3B}R^{3C}$, $-C(O)R^{3D}$, $-C(O)OR^{3D}$, $-C(O)NR^{3B}R^{3C}$, $-OR^{3A}$, $-NR^{3B}SO_2R^{3A}$, $-NR^{3B}C(O)R^{3D}$, $-NR^{3B}C(O)OR^{3D}$, $-NR^{3B}OR^{3D}$, $-OCX^{3.1}_3$, $-OCHX^{3.1}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1A}$, $R^{1B}$, $R^{1C}$, $R^{1D}$, $R^{2A}$, $R^{2B}$, $R^{2C}$, $R^{3D}$, $R^{3A}$, $R^{3B}$, $R^{3C}$ and $R^{3D}$ are independently hydrogen, halogen, $-CF_3$, $-CCl_3$, $-CBr_3$, $-CI_3$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)-OH$, $-NHOH$, $-OCF_3$, $-OCCl_3$, $-OCBr_3$, $-OCI_3$, $-OCHF_2$, $-OCHCl_2$, $-OCHBr_2$, $OCHI_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1B}$, $R^{1C}$, $R^{2B}$, $R^{2C}$, $R^{3B}$ and $R^{3C}$ substituents bonded to the same nitrogen atom may optionally be joined to form a substituted or unsubstituted heterocycloalkyl or substituted or unsubstituted heteroaryl; and $X^{1.1}$, $X^{2.1}$ and $X^{3.1}$ are independently $-Cl$, $-Br$, $-I$ or $-F$.

Embodiment 40. The method of embodiment 39, wherein $L^1$ is substituted or unsubstituted unbranched alkylene or substituted or unsubstituted unbranched heteroalkylene.

Embodiment 41. The method of embodiment 39, wherein $R^3$ is a dye, a fluorophore, an antibody, a biomolecule, a polypeptide, a protein, a nucleic acid molecule, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment 42. The method of embodiment 39, wherein $R^3$ is thiazole orange or a derivative thereof.

Embodiment 43. The method of embodiment 39, wherein $R^3$ is biocytin, biotin, a boron-dipyrromethene dye or a cyanine dye.

EXAMPLES

Example 1

Initial RNA Transglycosylation Studies

Rationale. Transglycosylation of an RNA fragment using PreQ1 or derivative of PreQ1 should demonstrate proof of concept of the procedures disclosed herein.

Experimental Conditions. tRNA fragment (17-mer): 20 µM. PreQ1 or derivative: 200 µM. Transglycosylase (bacterial (*E. coli*) tRNA Guanine Transglycosylase (TGT): 500 nM; total volume: 50 uL. Buffer: 100 M HEPES, pH 7.3, 5 mM DTT, 20 mM $MgCL_2$. Mixtures were incubated for 1.5 hr at 37° C.

Nucleic acid reagents: tRNA fragment: GCA GAC UGU AAA UCU GC (native nucleobase); GCA GAC UXU AAA UCU GC ("X" is PreQ1 bound to $PEG_3$-amine).

Analysis. Reaction mixtures were directly injected into the LC/TOF instrument for mass spectral analysis. LC conditions: basic conditions on C-18 reverse phase column; phase A A=1000:30:0.4 $H_2O$:HFIP:TEA. Phase B: MeO H, 10-min gradient from 95% to 5% A; flow: 1 mL/min.

Results. Mass spectral results after reaction were obtained for native tRNA (SEQ ID NO:5, m/z 5409.320) and tRNA having a PreQ1-PEG-amine (SEQ ID NO:7). The observed mass spectral range corresponds to higher order (e.g., m/5z, m/6z, m/7z, m/8z, and the like) charged ions.

Example 2

Site-Specific Covalent Labeling of Rna by Enzymatic Transglycosylation.

Abstract. We demonstrate the site-specific incorporation of nucleobase derivatives bearing fluorophores or affinity labels into a short RNA stem loop recognition motif by exchange of a guanine residue. The RNA-TAG (transglycosylation at guanosine) is carried out by a bacterial (*E.coli*) tRNA guanine transglycosylase (TGT), whose natural substrate is the nitrogenous base PreQ1. Remarkably, we have successfully incorporated large functional groups including biotin, BODIPY, thiazole orange, and Cy7 through a polyethylene glycol linker attached to the exocyclic amine of PreQ1. Larger RNAs, such as mRNA transcripts, can be site-specifically labeled if they possess the 17-nucleotide hairpin recognition motif. The RNA-TAG methodology could facilitate the detection and manipulation of RNA molecules by enabling the direct incorporation of functional artificial nucleobases using a simple hairpin recognition element.

The detection and manipulation of RNA is greatly aided by chemical modification. Therefore, there is tremendous interest in novel methods to site-specifically associate RNA with small molecules such as imaging probes and affinity labels.[1] Conventional methodologies for detecting RNA include the use of antisense probes,[2] aptamers,[3] and fusion proteins that recognize specific RNA secondary structures.[4] Relatively less explored are the use of enzymatic reactions for site-specific RNA labeling.[5] It is known that RNA can be post-transcriptionally modified in numerous ways by specialized enzymes. For instance, there are approximately 85 post-transcriptional modifications of various transfer RNA (tRNA) structures, with the majority of modifications present on the anticodon stem loop.[6] There are several examples of utilizing enzymes to accomplish site-specific covalent modification of RNA.[7] Recent work has also shown that several tRNA modifying enzymes can covalently attach small analogs bearing either azide or alkyne handles to RNA.[1c,8] Notably, these past approaches have not demonstrated the ability to append large functional molecules directly onto the RNA of interest. Instead they typically rely upon small bioorthogonal handles, which after undergoing a second chemical reaction, can be modified by functional probes such as fluorophores or affinity ligands.

An ideal enzymatic reaction for labeling RNA would involve recognition of a minimal RNA structural motif, result in irreversible covalent modification, and would be capable of directly incorporating a diverse array of functional molecules (fluorophores, affinity ligands, etc.) in a single step. Here we introduce RNA-TAG (transglycosylation at guanosine), an enzymatic method to directly append large functional molecules site-specifically to RNA. This method utilizes a bacterial tRNA guanine transglycosylase (TGT) to exchange specific guanine nucleobases with functional derivatives of the bacterial nucleobase $PreQ_1$. By enabling the direct incorporation of functional artificial nucleobases using a simple hairpin recognition element, RNA-TAG should have numerous applications as an RNA labeling tool.

TGTs are a well-characterized class of enzymes that are found in archaea, eubacteria and eukaryotes.[9] While most RNA post-transcriptional modifications occur through derivatization of a genetically encoded nucleoside, TGTs are capable of performing transglycosylation reactions in which a guanine at the wobble position of the anticodon loop is exchanged with 7-deazaguanine derivatives. While eukaryotic TGTs selectively incorporate queuine salvaged from the environment, bacterial TGTs instead incorporate an amine containing queuine precursor, $PreQ_1$, which is later enzymatically modified to yield queuine.[10] Extensive prior studies with the bacterial TGT from *E. coli* revealed a minimal binding domain of a single 17-nucleotide hairpin (ECY-A1) mimicking the anticodon stem loop of the tRNA substrate.[11] Furthermore, complementary studies have shown that the enzyme can recognize extended RNA molecules bearing minimal hairpin recognition elements, including tRNA dimers and mRNA.[12]

Since transglycosylation is an efficient mechanism for the incorporation of highly modified bases into RNA,[13] we speculated that TGT-catalyzed nucleobase exchange could be harnessed to covalently modify RNA site-specifically with synthetic molecules such as fluorophores and affinity ligands. However, although bacterial TGTs have been shown to tolerate various $PreQ_1$ analogs, loss of the exocyclic amine or sterically hindered derivatives can cause a dramatic loss of activity.[14] For instance, several studies have demonstrated that bacterial TGT will not accept queuine as a substrate.[10,15] Indeed, crystal structures of a bacterial TGT with bound RNA and nucleobase substrates reveals several protein contacts with $PreQ_1$, including a key hydrogen bond between the exocyclic amine of $PreQ_1$ and the carbonyl oxygen of a leucine residue.[16] To maintain this important hydrogen bonding interaction in our synthesized PreQ1 analogs, we decided to link functional groups through alkylation of the exocyclic amine. Furthermore, we appended our functional groups via a short oligoethylene glycol spacer, with the goal of extending any large functional groups away from the active site.

To initially test for RNA modification, we utilized the previously reported 17-nucleotide RNA hairpin ECY-A1, which mimics the anticodon arm of $tRNA^{Tyr}$, and has been shown to be recognized as a substrate by bacterial TGT.[11] We incubated ECY-A1 with TGT along with PreQ1 analogs linked to various fluorophores and affinity ligands such as BODIPY, thiazole orange (TO), Cy7, and biotin (FIG. 1A). We found that all PreQ1 analogs could be successfully incorporated into the RNA hairpin, as judged by liquid chromatography (LC) retention time shifts and high resolution mass spectrometry (HRMS) (Table 1). It is worth mentioning that the modification worked with large functional groups; in the maximum case, a near-IR cyanine dye of 534 Da molecular weight.

TABLE 1

DECONVOLUTED MS EXPECTED AND FOUND DATA FOR RNA HAIRPINS MODIFIED BY TGT

| Modified RNA Oligonucleotides | Expected Parent m/z | Observed Deconvoluted m/z |
|---|---|---|
| Native ECY-A1 | [M + Na − 2H]⁻ 5431.309 | [M + Na − 2H]⁻ 5431.709 |
| ECY-A1-PreQ₁-TO | [M + Na − 2H]⁻ 6020.180 | [M + Na − 2H]⁻ 6020.976 |
| ECY-A1-PreQ₁-BODIPY | [M − H]⁻ 5887.119 | [M − H]⁻ 5887.998 |
| ECY-A1-PreQ₁-Cy7 | [M + Na − 2H]⁻ 6166.719 | [M + Na − 2H]⁻ 6166.193 |
| ECY-A1-PreQ₁-Biotin | [M + Na − 2H]⁻ 5861.460 | [M + Na − 2H]⁻ 5861.947 |

To test for RNA substrate selectivity, we incubated PreQ$_1$-TO, TGT, and RNA hairpin ECY-A 1, and compared modification to alternative RNA hairpins ECY-A1ΔC, and ECY-X 1 (Table 2). ECY-A1 ΔC has the reactive guanine changed to a cytosine while ECY-X1 maintains the 7-member hairpin loop and UGU recognition element, but shifts the location of the UGU and the neighboring bases. In either case, we were unable to detect incorporation of PreQ$_1$-TO by LC/MS, demonstrating that RNA-TAG is selectively incorporating PreQ$_1$ analogs in place of guanine and that the process is specific to the hairpin recognition element, in agreement with previous studies.[17]

TABLE 2

RNA OLIGONUCLEOTIDE SEQUENCES

| RNA Oligonucleotide | Sequence |
|---|---|
| ECY-A1 | 5'GCA GAC UGU AAA UCU GC3' |
| ECY-A1ΔC | 5'GCA GAC UCU AAA UCU GC3' |
| ECY-X1 | 5'CG UCU AAA UGU CAG ACG3' |

Figure 2A:
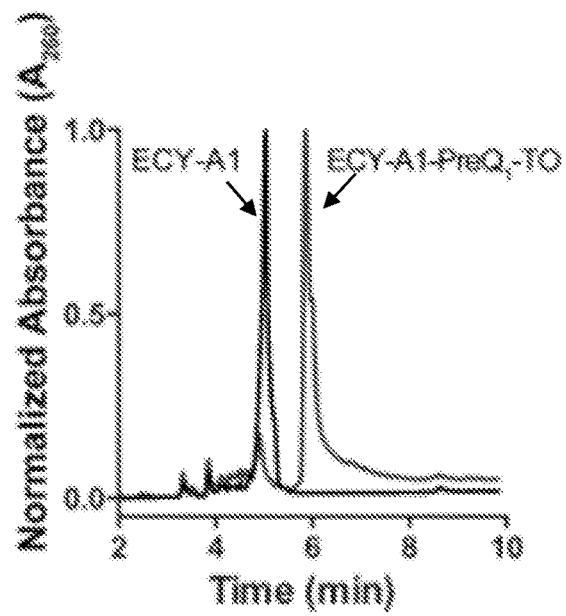
FIGS. 2A-2C. TGT labeling reactions of RNA with PreQ1 analogs.
Figure 2B:
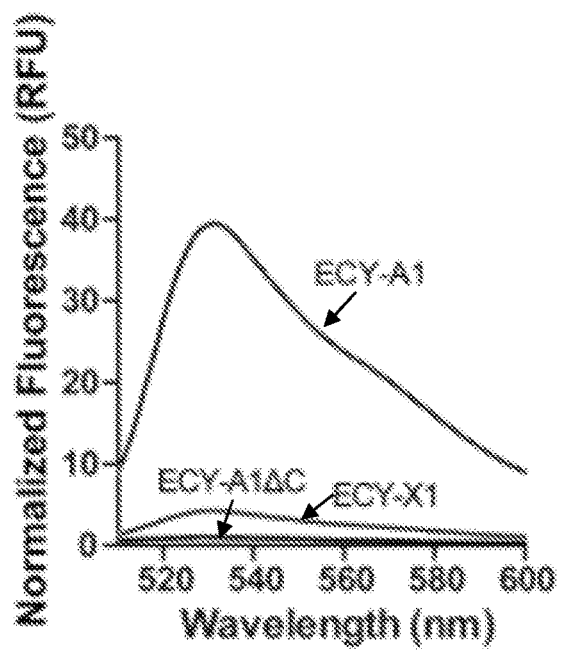

There is significant interest in methods to detect and image RNA.[1] RNA-TAG could be useful for RNA imaging, however, to limit background fluorescence due to unreacted probe, it would be beneficial if nucleobase exchange was accompanied by an increase in fluorescence intensity. To explore fluorogenic RNA-TAG reactions, we focused our attention on the PreQ$_1$-TO probe. TO probes are known to dramatically increase in fluorescence intensity upon intercalation into double stranded nucleic acids.[18] While this can lead to non-specific binding, recent work has demonstrated that TO derivatives bearing functional group handles show decreased non-specific binding to nucleic acids, and, when coupled to small molecules which bind to RNA aptamers, can be used to induce specific fluorogenic responses.[19] As such, we speculated that PreQ$_1$-TO modification of RNA could lead to an increase in fluorescence intensity due to intercalation of the TO probe into the RNA stem, driven by the high local concentration of the covalently bound TO. We tracked the fluorescence intensity of PreQ$_1$-TO before and after covalent incorporation into the RNA hairpin ECY-A1. We found that incorporation of PreQ$_1$-TO led to an approximate 40-fold increase in TO fluorescence intensity, indicating that covalent modification by RNA-TAG likely drives TO-RNA intercalation (FIG. 2B).

Figure 2C:
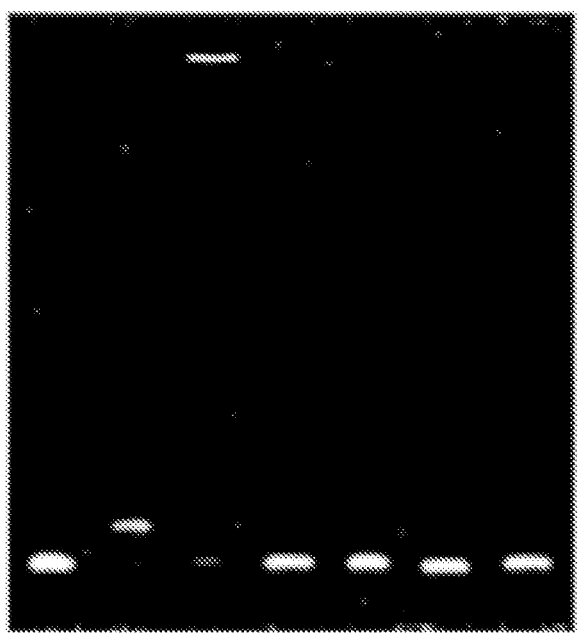

The ability to use RNA-TAG to introduce a biotin group could have application for the affinity tagging and pull-down of specific RNAs. While many studies utilize biotinylated RNA, the biotin group is typically incorporated during in vitro RNA synthesis.[20] RNA-TAG could be a facile way to covalently incorporate biotin into native RNAs. As a proof of concept, we subjected both ECY-A1 and ECY-A1ΔC to TGT with PreQ$_1$-Biotin and performed a streptavidin gel-shift assay (FIG. 2C). We observed a gel shift of ECY-A1 upon binding streptavidin only when the RNA was covalently modified by TGT with PreQ$_1$-Biotin, indicating that the biotin remains functional as an affinity tag, even after incorporation into RNA by TGT.

Figure 6A:
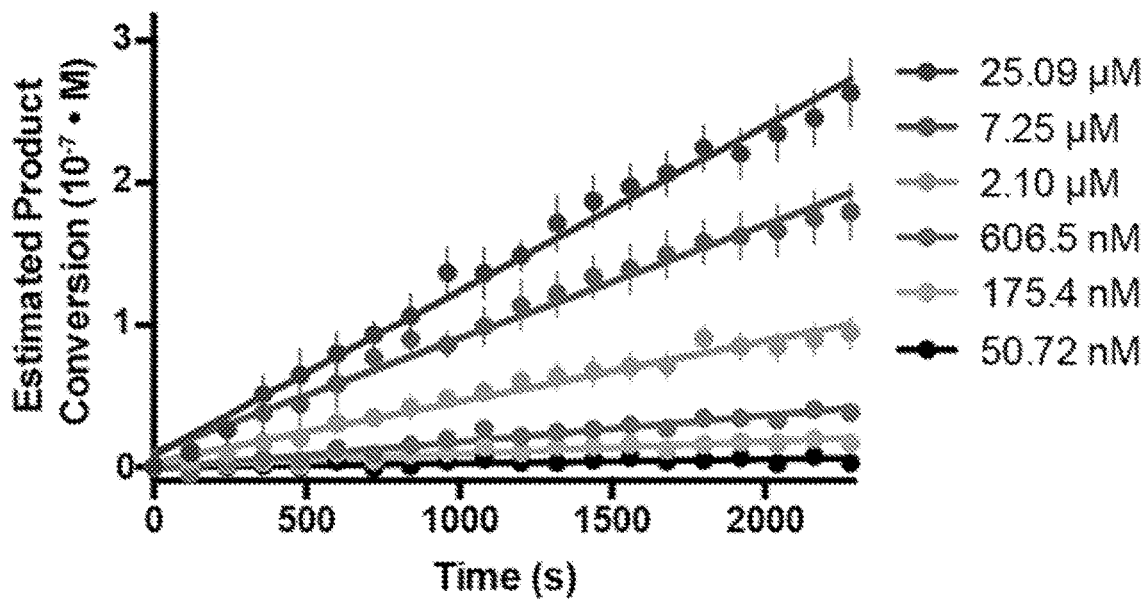
FIGS. 6A-6B. Kinetic data of PreQ$_1$-TO with ECY-A1 catalyzed by TGT.
Figure 6B:
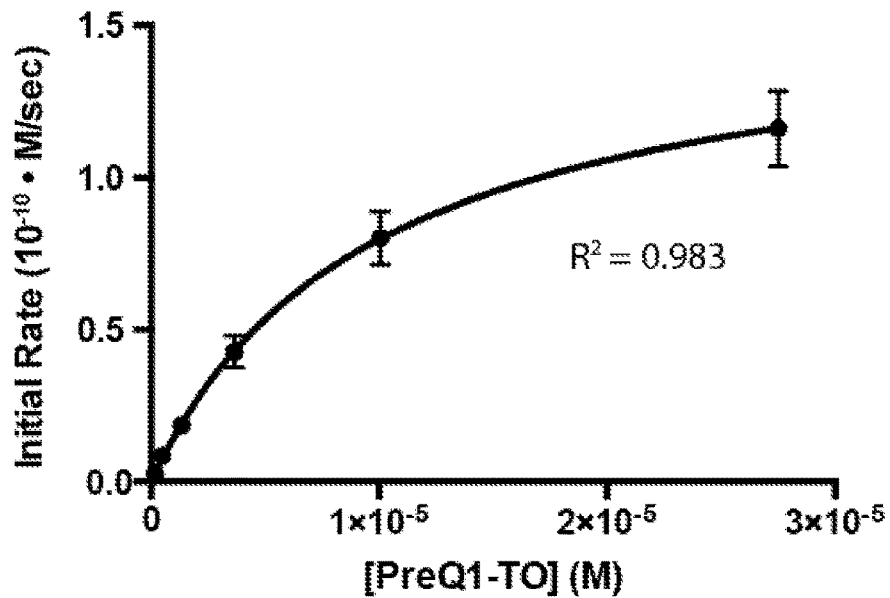

As our PreQ$_1$-derivatives have structures that deviate significantly from natural PreQ$_1$, we next estimated the kinetics of enzymatic incorporation of a fluorophore linked PreQ$_1$ analog. We capitalized on the fluorogenicity of PreQ$_1$-TO as a facile way to track TGT catalyzed incorporation of this analog. Monitoring the increase in fluorescence intensity, we determined initial rates and derived an estimated $K_m$ of 9.8 μM and a $k_{cat}$ of $1.6 \cdot 10^{-3}$ s$^{-1}$ (FIGS. 6A-6B), which does not greatly differ from results found using alternative analogs of PreQ$_1$, albeit with much smaller perturbations in structure.[11,14,17a]

Figure 3A:
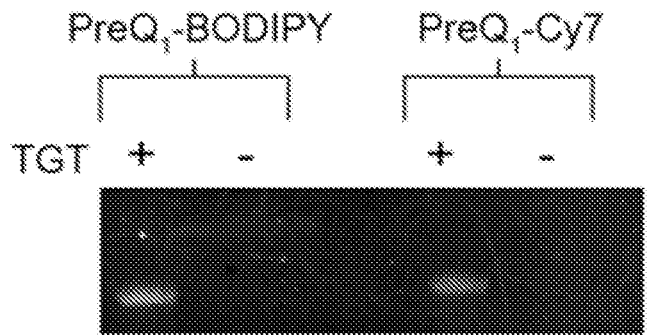
FIGS. 3A-3C. TGT labeling reactions with full-length RNA transcripts containing a recognition sequence in the 3' UTR.
Figure 3B:
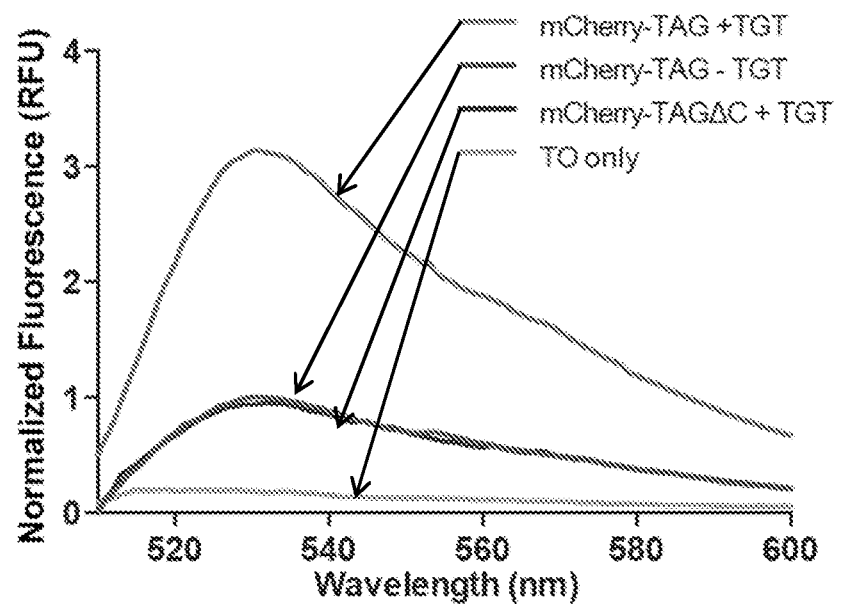
Figure 7:
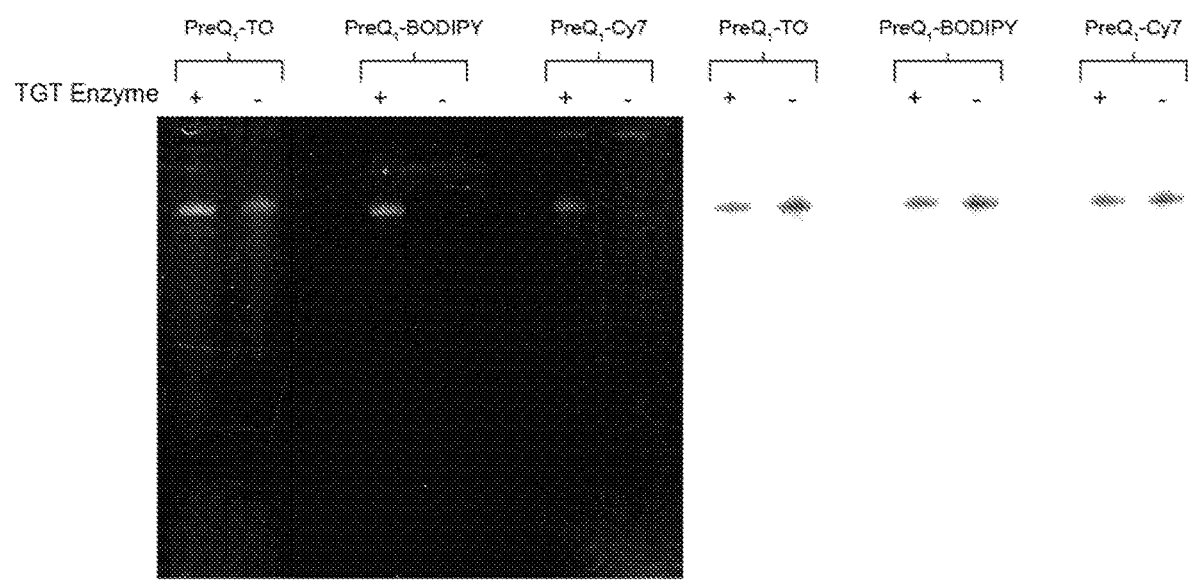
FIG. 7. PAGE gel of mCherry-TAG labeled with different fluorescent PreQ$_1$ probes. 4% PAGE gel of mCherry-TAG labeled with PreQ$_1$ fluorescent probes imaged by multi-channel fluorescence imaging (left) and by white light imaging after methylene blue staining (right). PreQ$_1$-TO in the absence of enzyme is visible due to non-specific binding of PreQ$_1$-TO with the in vitro transcribed RNA.
Figure 8:
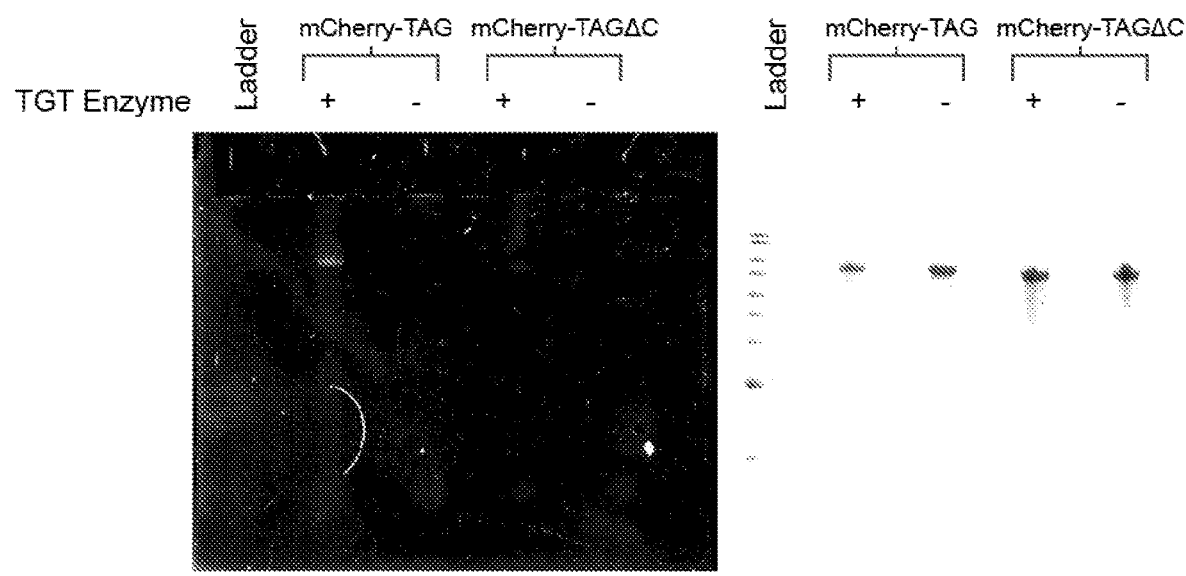
FIG. 8. PAGE gel of mCherry-TAG and mCherry-TAGΔC labeled with PreQ$_1$-BODIPY. 4% PAGE gel of PreQ$_1$-BODIPY labeled mCherry transcripts imaged by fluorescence imaging (left) and white light imaging after staining with methylene blue (right).
Figure 9:
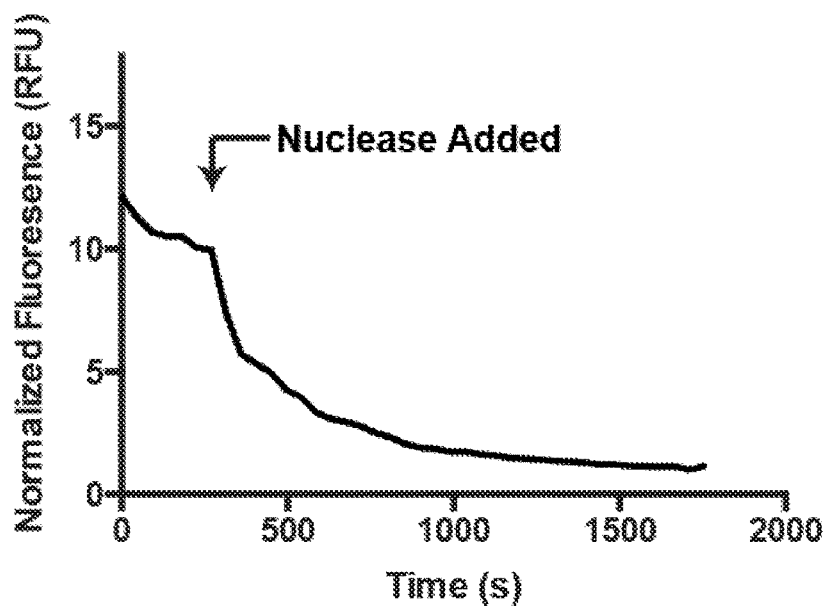
FIG. 9. mCherry-TAG fluorogenic degradation study. 10 µM TGT enzyme, 20 µM PreQ$_1$-TO, and 100 nM transcript RNA were incubated at 37° C. for 2 hours. Samples were then diluted 30-fold, and subjected to micrococcal nuclease (NEB) at the time point indicated and fluorescence was monitored over time. Fluorescence was normalized to 20 µM PreQ$_1$-TO in buffer.

Having demonstrated that RNA-TAG could append unnatural PreQ$_1$ analogs onto minimal RNA hairpins, we next sought to determine if the minimal recognition hairpin could be recognized on much larger RNA molecules such as mRNA transcripts. We inserted the ECY-A1 hairpin within the 3' UTR of an mRNA transcript coding for the red fluorescent protein mCherry (mCherry-TAG). Transcripts were exposed to PreQ$_1$-BODIPY and PreQ$_1$-Cy7 with and without enzyme. The transcripts were run on a denaturing polyacrylamide gel and labeling was detected by fluorescence imaging (FIG. 3A). When TGT is present, labeling of the transcript took place, as indicated by observation of strong fluorescent bands on the polyacrylamide gel that colocalized with the transcript RNA (FIG. 7). The mCherry mRNA transcript contains 11 instances of UGU, making it possible that TGT could modify an off target sequence. To test this, we mutated the G of the hairpin recognition motif to C (mCherry-TAGΔC) and attempted to incorporate PreQ$_1$-BODIPY. In this case, we observed negligible fluorescence staining of the RNA transcript, demonstrating that labeling is specific to the UGU sequence of our appended hairpin with minimal off target reactions (FIG. 8). To determine if fluorogenic labeling was also possible on in vitro transcribed RNA, transcripts were isolated and exposed to PreQ$_1$-TO with or without bacterial TGT. Although background fluorescence was observed due to non-specific binding of PreQ$_1$-TO to RNA,[19] when TGT was present, we observed a significant increase in fluorescence intensity, which persisted after protease degradation of the enzyme (FIG. 3B). Furthermore, this fluorescence increase was reversed upon degradation of the RNA, indicating the probe's ability to serve as a metric for RNA lifetime (FIG. 9). We also tested mCherry-TAGAC for its ability to react with PreQ$_1$-TO. In this case, we observed negligible fluorescence turn-on in the presence of enzyme.

Figure 3C:
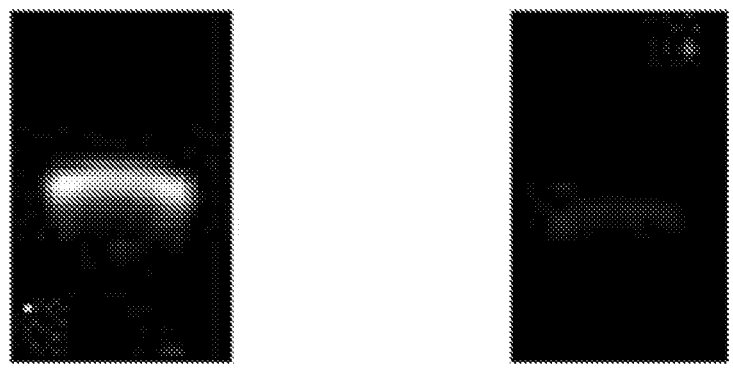
Figure 10:
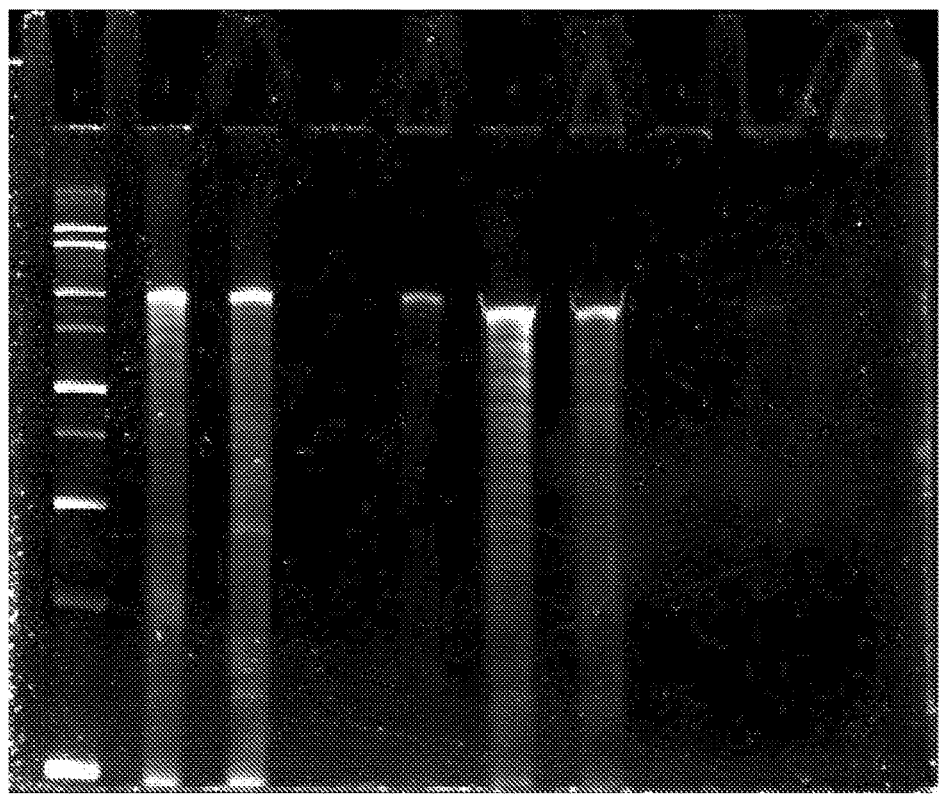
FIG. 10. PAGE gel of DYNABEADS® pull-down assay with PreQ$_1$-Biotin modified transcripts. 4% PAGE gel illustrating RNA present during different stages of the streptavidin pull-down assay imaged by fluorescence imaging after staining with Sybr Green-II.
Figure 11A:
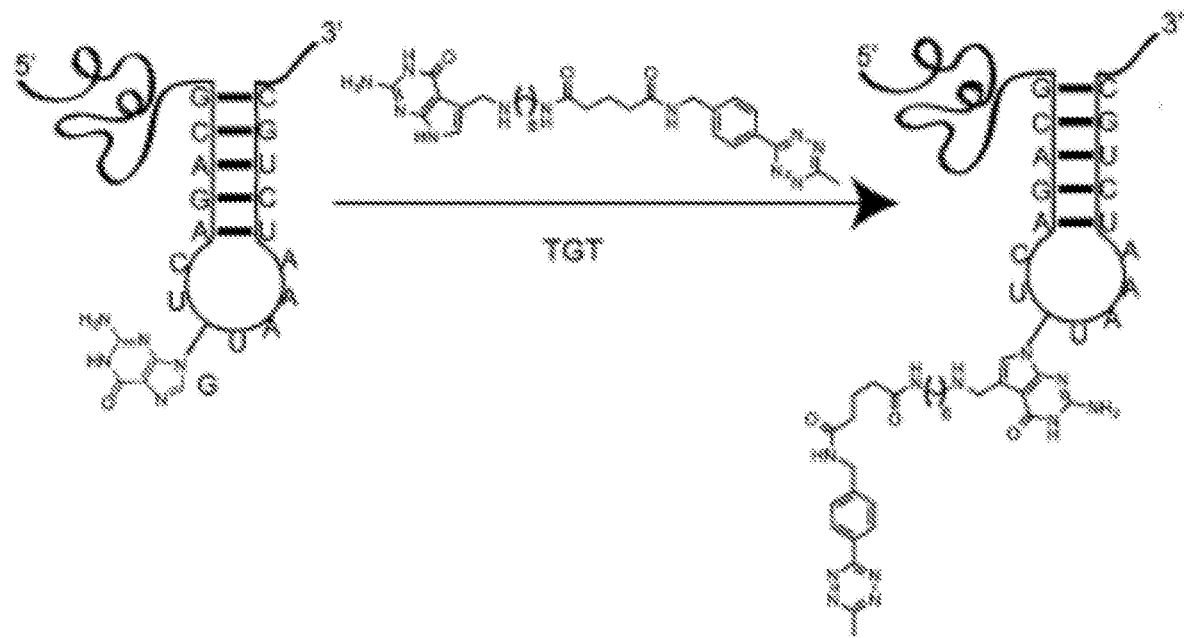
FIGS. 11A-11B.
Figure 11B:
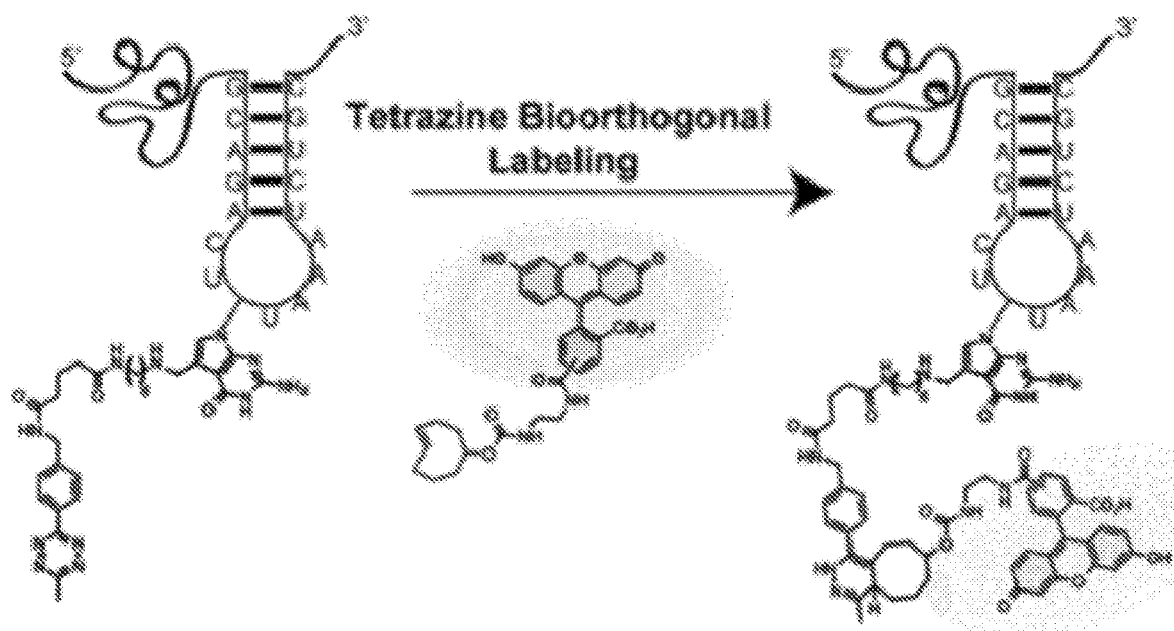
Figure 12:
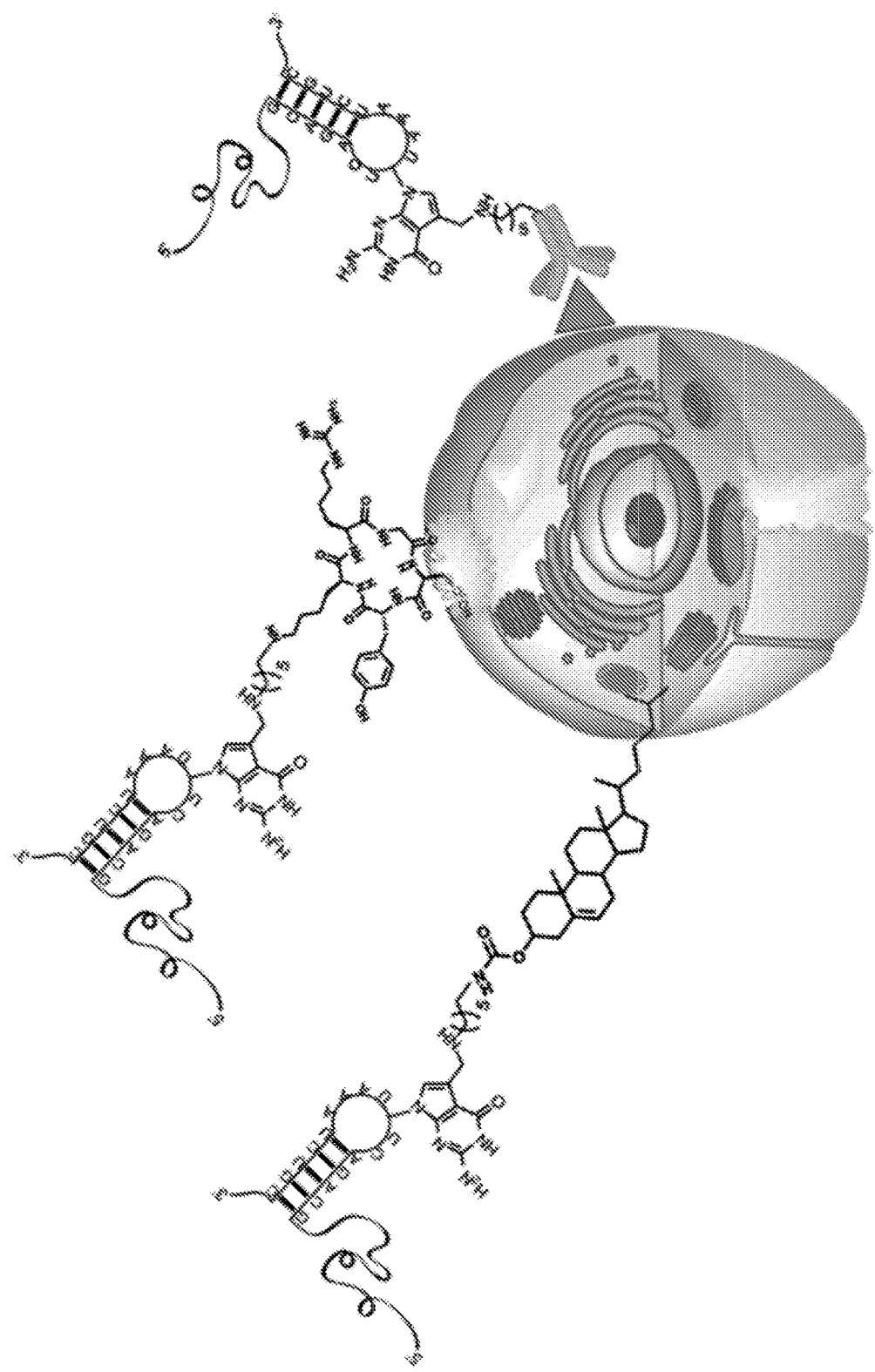
FIG. 12. Schematic representation of appended drug-targeting molecules using the RNA-TAG methodology.
Figure 13A:
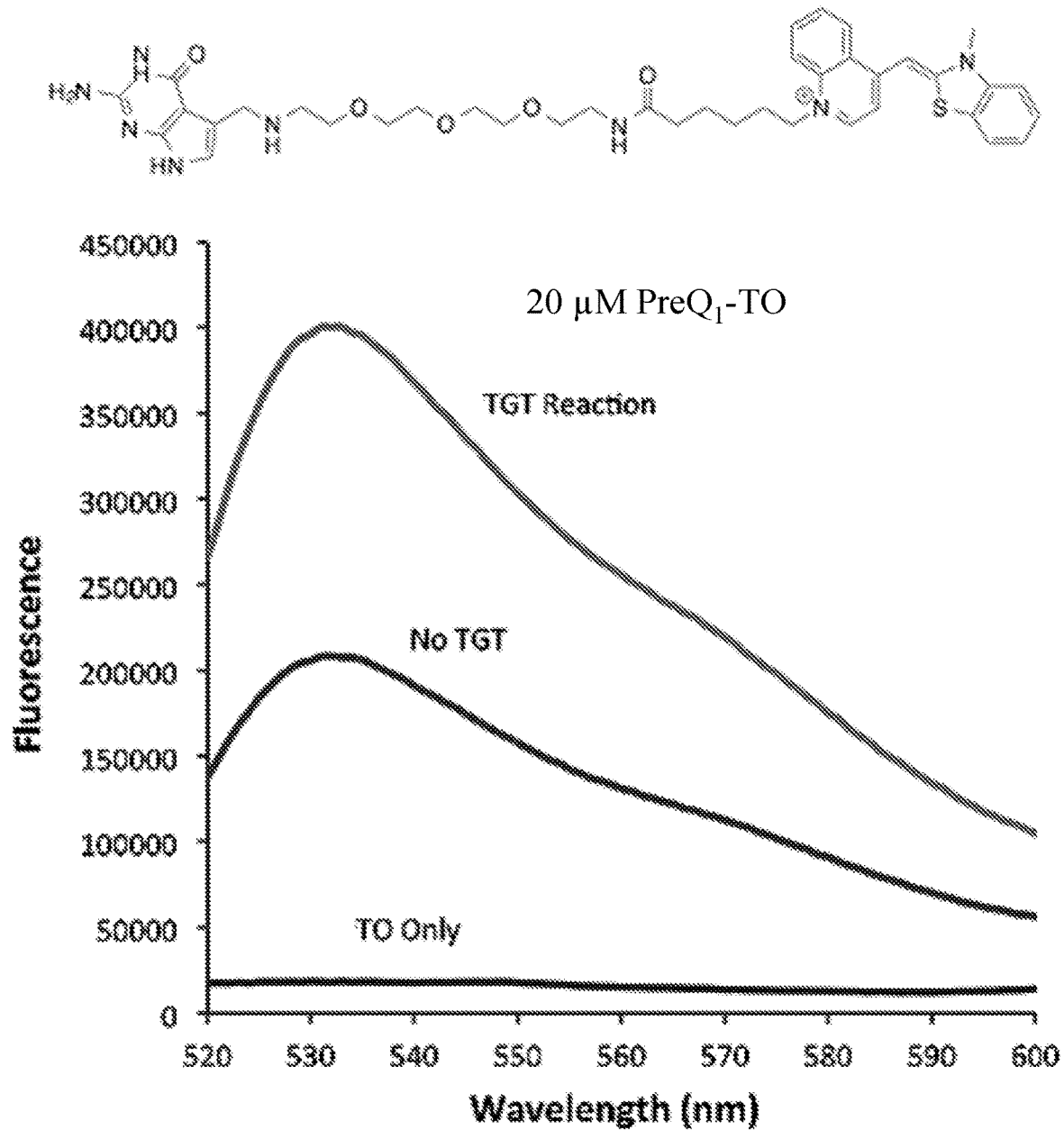
FIGS. 13A-13B.
Figure 13B:
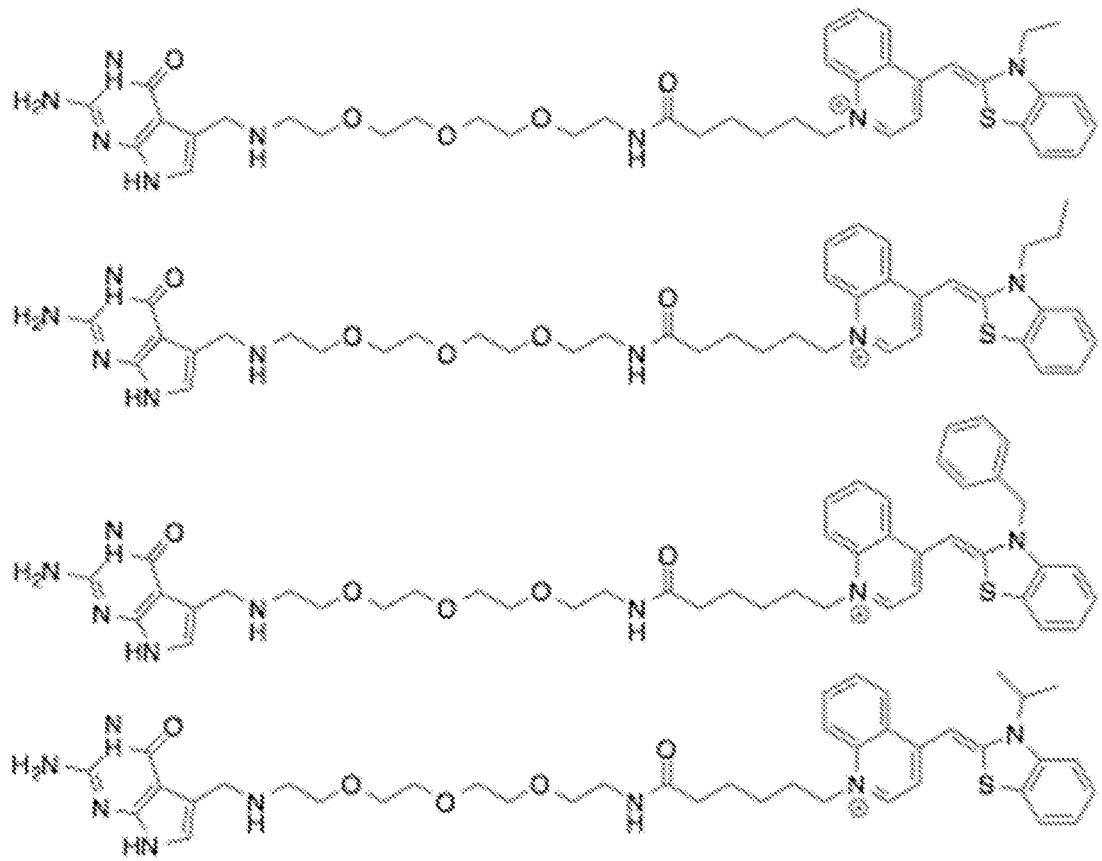
Figure 13B:
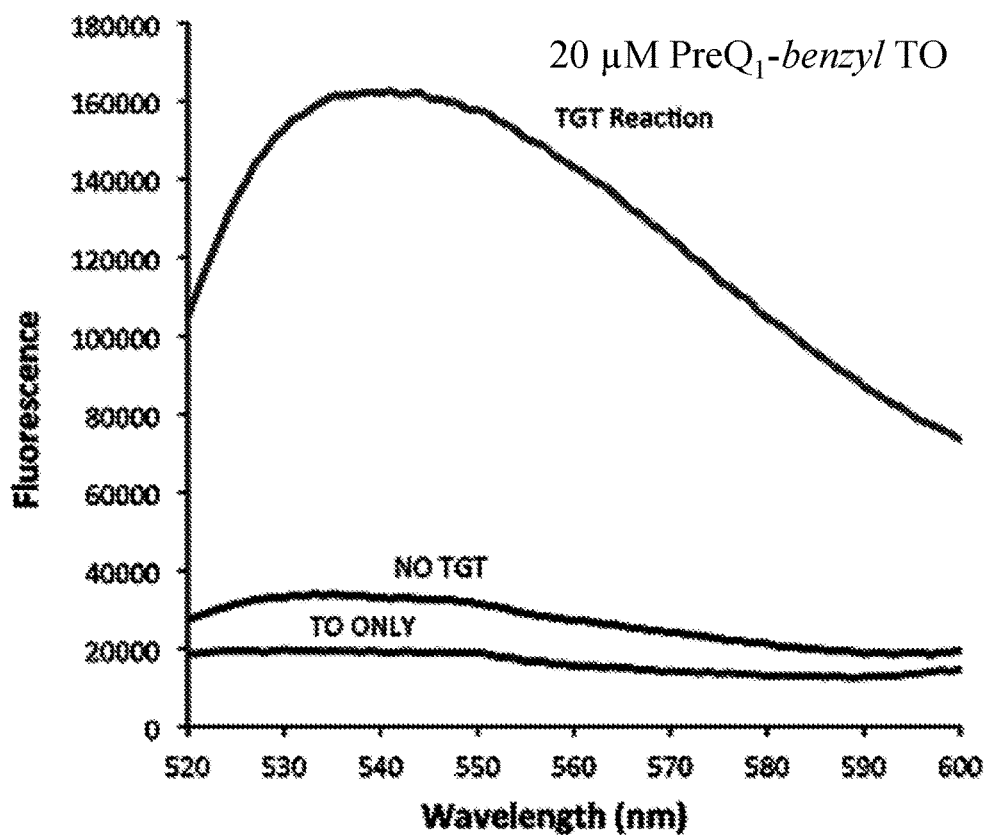
Figure 14A:
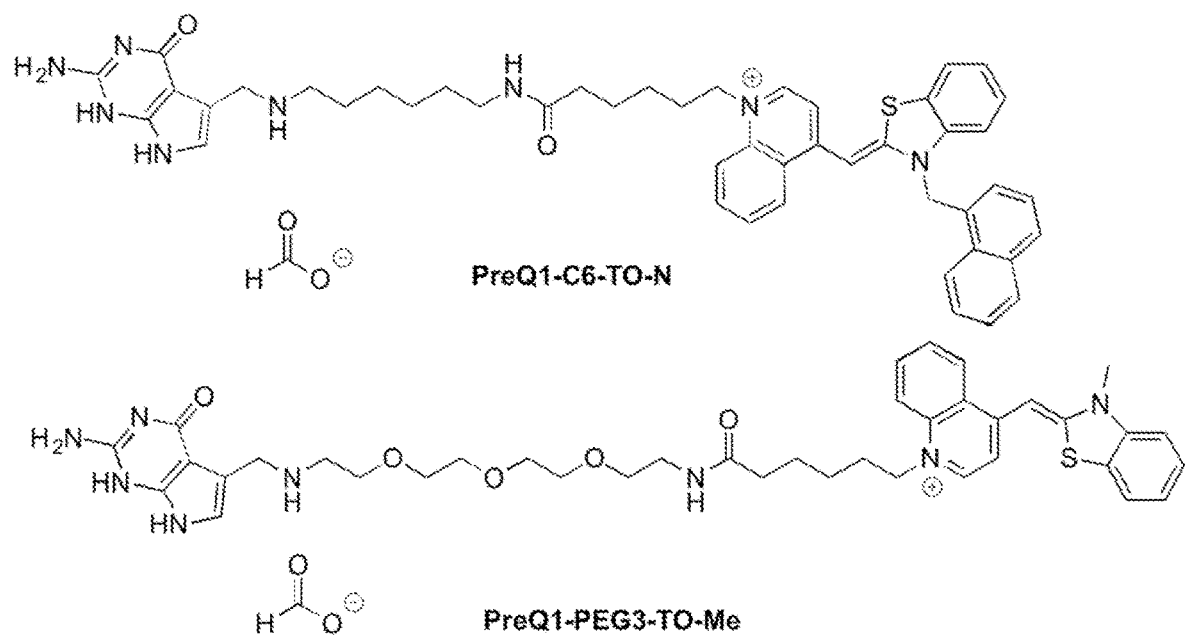
FIGS. 14A-14C.
Figure 14B:
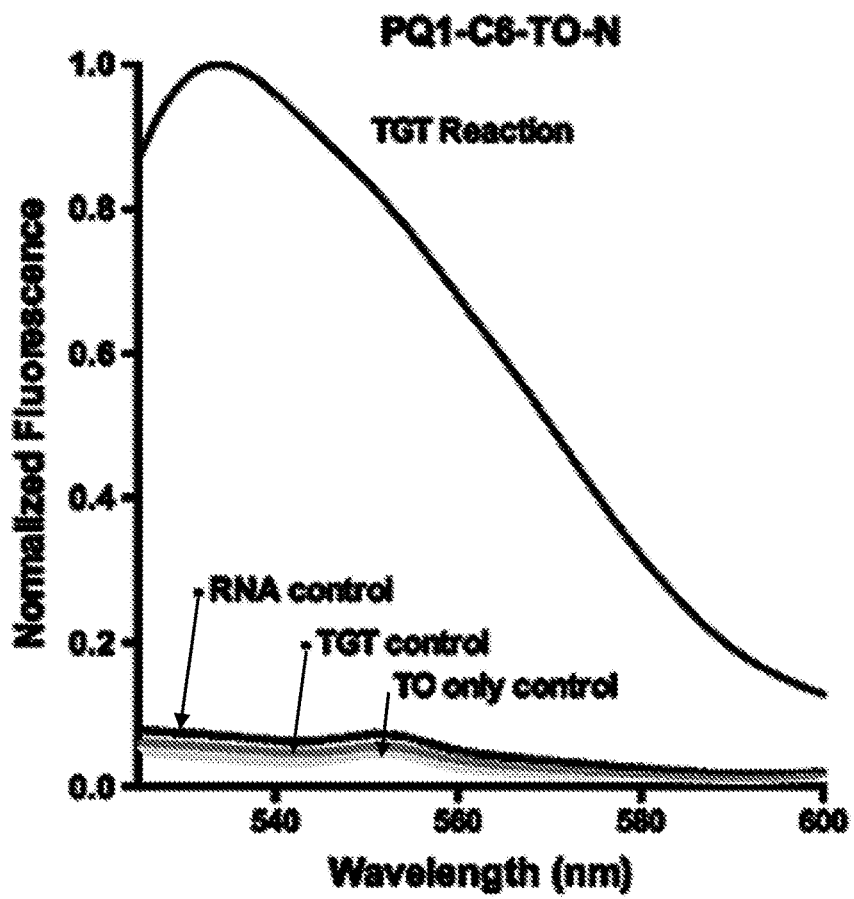
Figure 14C:
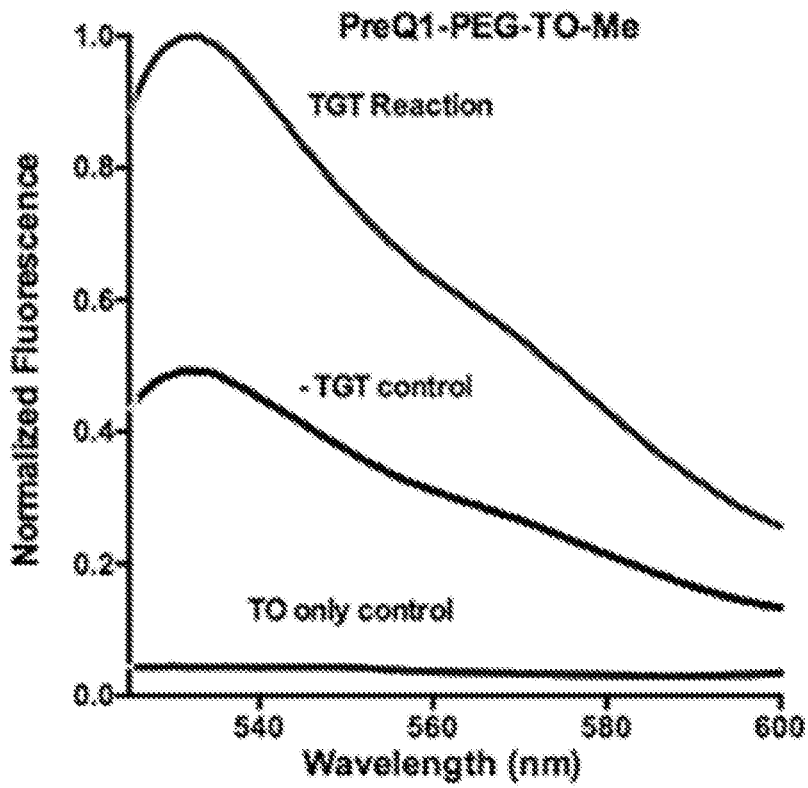
Figure 15A:
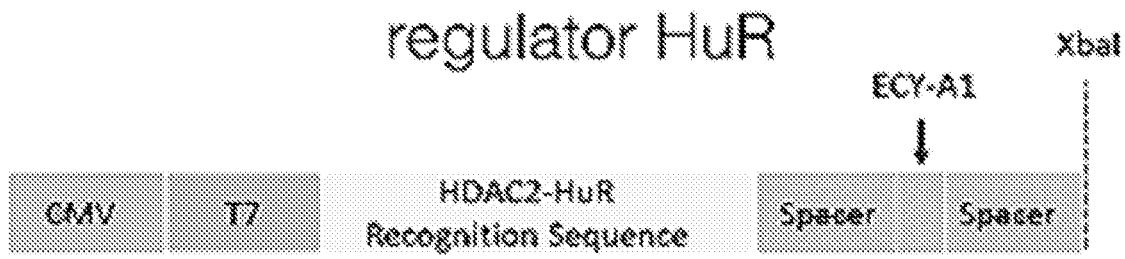
FIGS. 15A-15C.
Figure 15B:
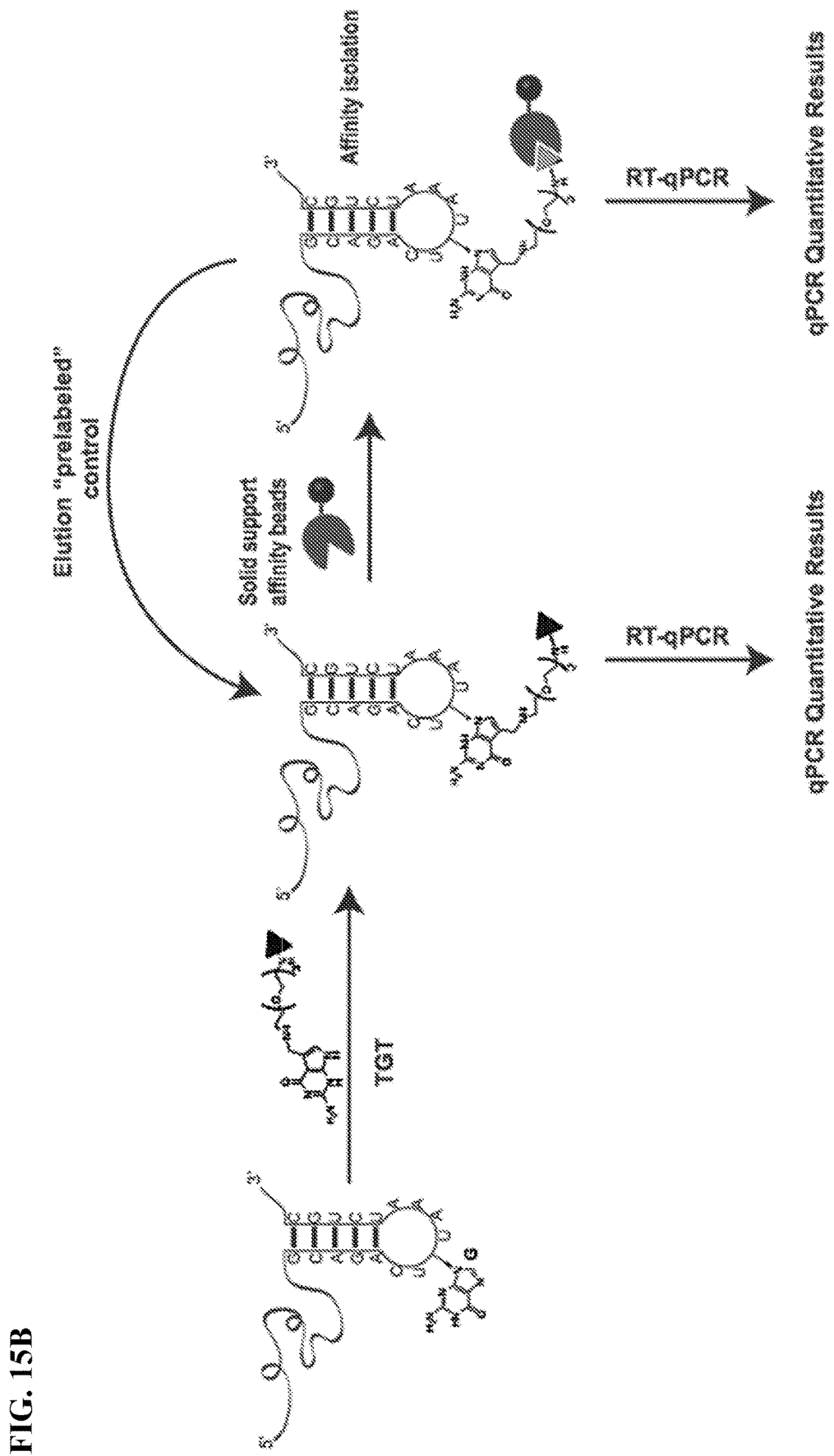
Figure 15C:
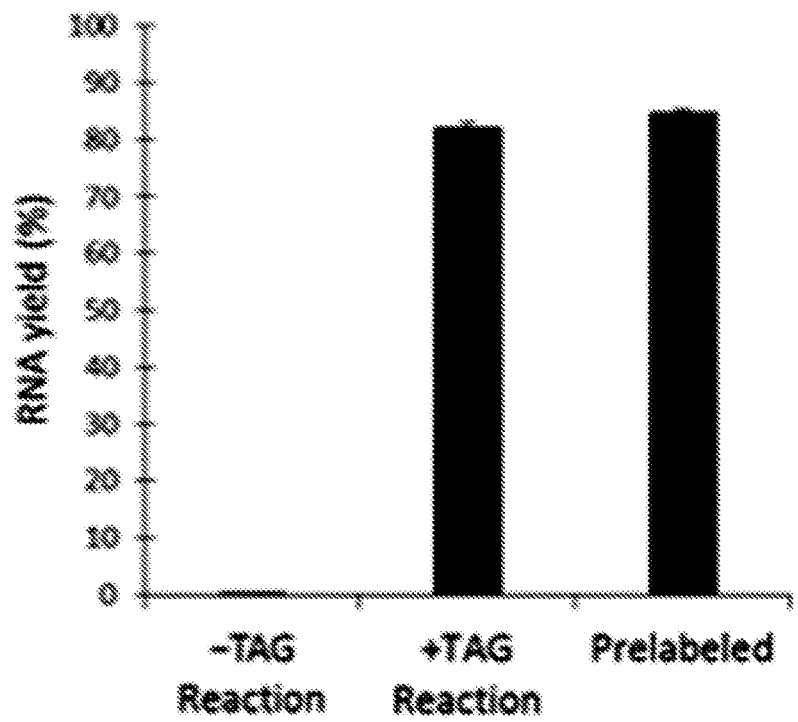
Figure 16:
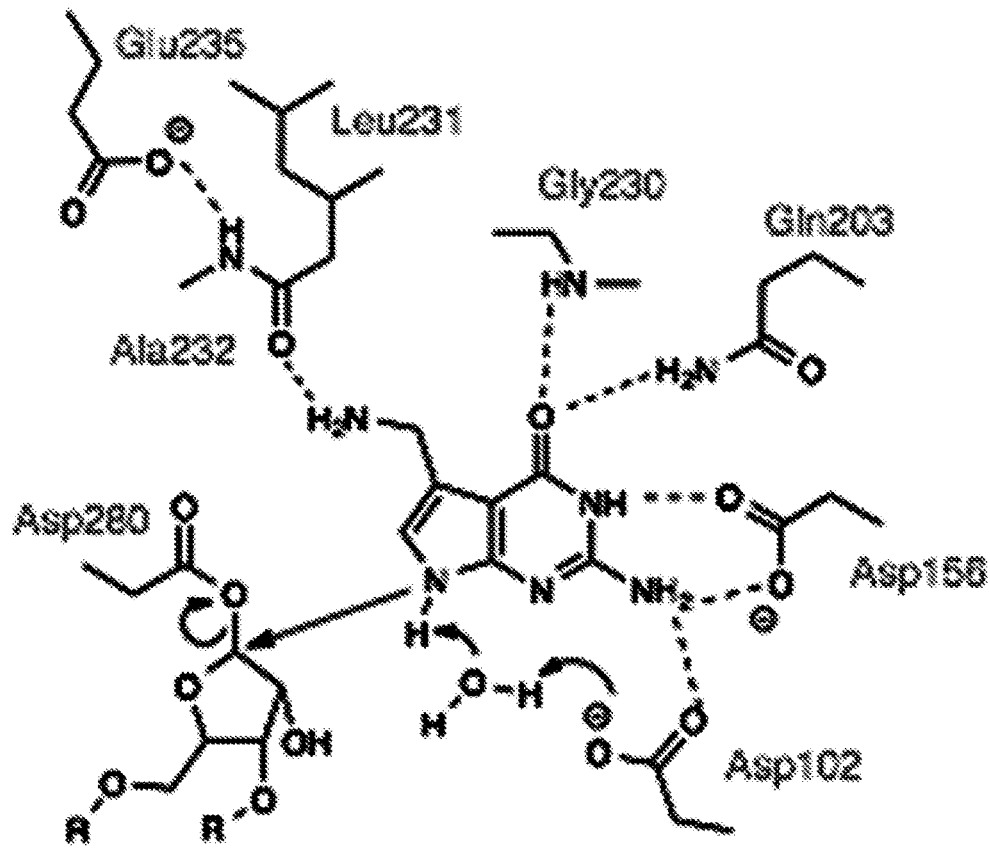
FIG. 16. Shows transglycosylase with bound RNA and nucleobase. Due to a key hydrogen bond between the exocyclic amine of PreQ1 and the carbonyl oxygen of a lysine residue, bacterial transglycosylase will not accept other nucleobases (e.g. quenine).
Figure 17:
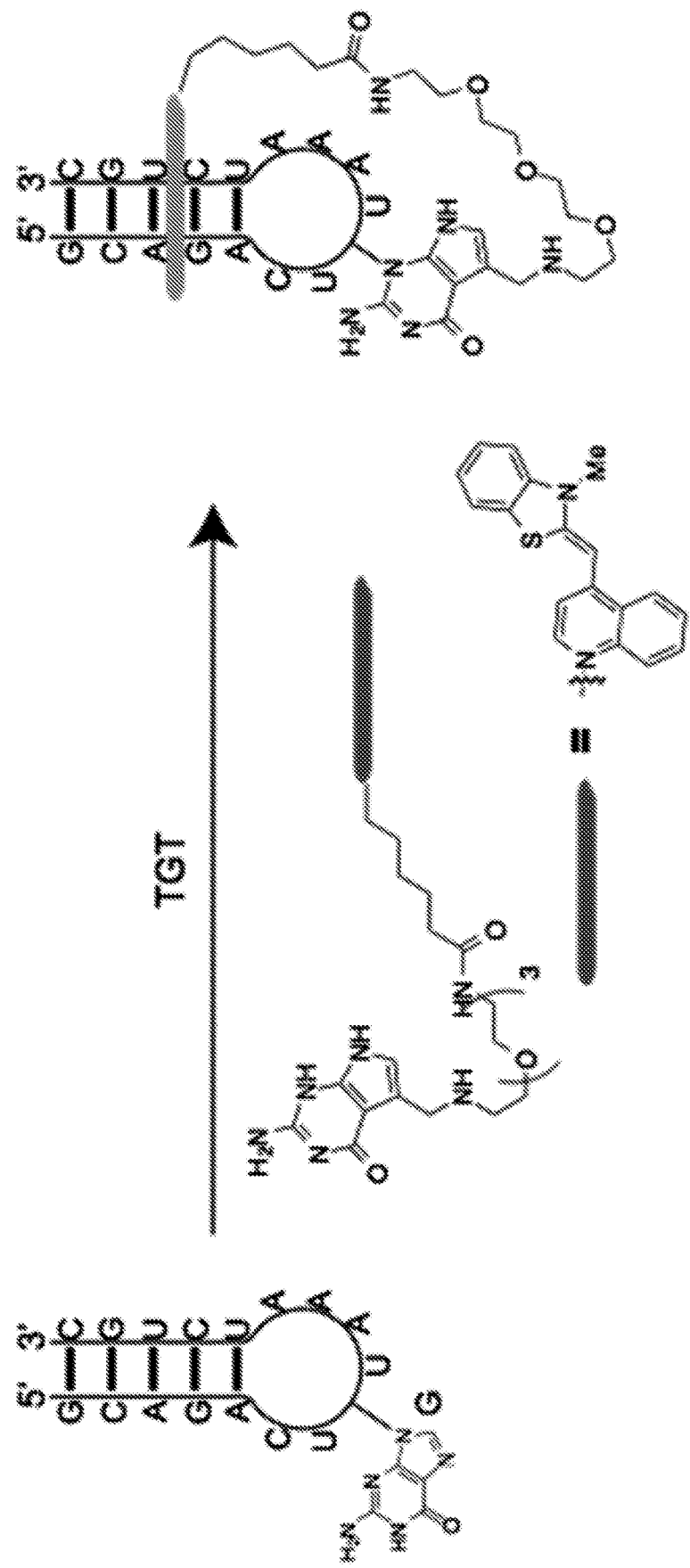
FIG. 17. Schematic representation demonstrating intercalation of a TO probe into RNA stem.
Figure 18A:
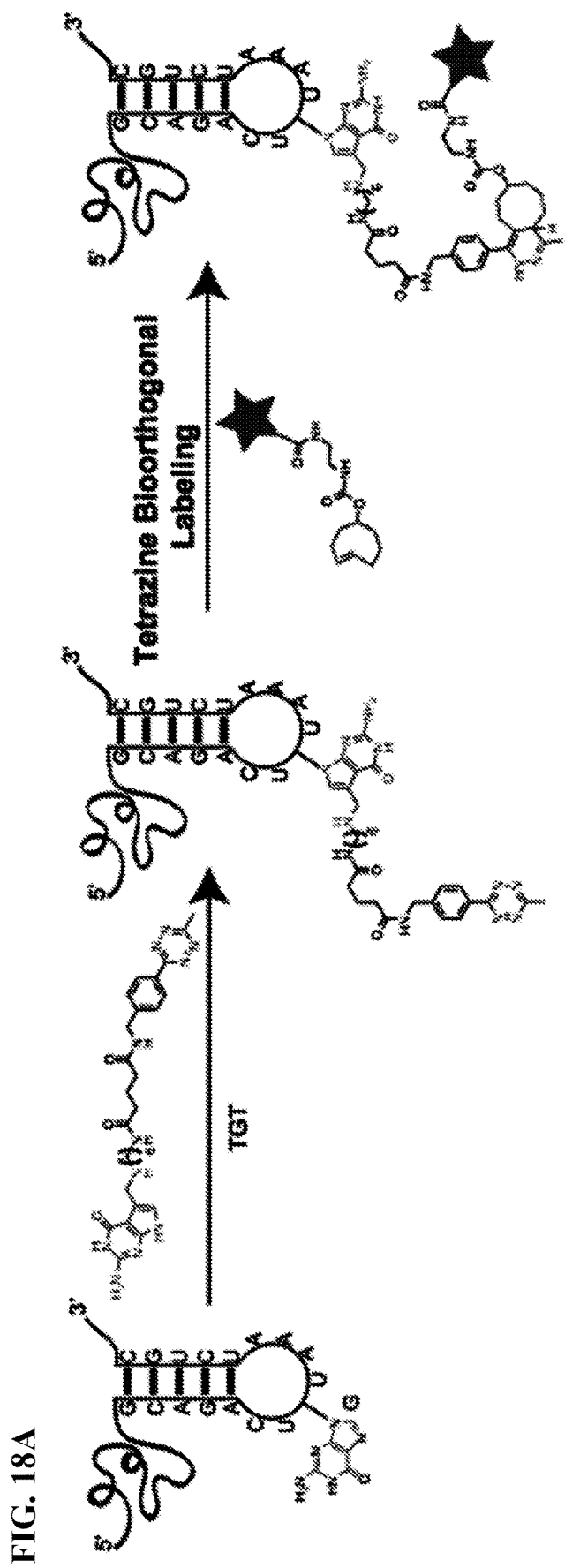
FIGS. 18A-18B.
Figure 18B:
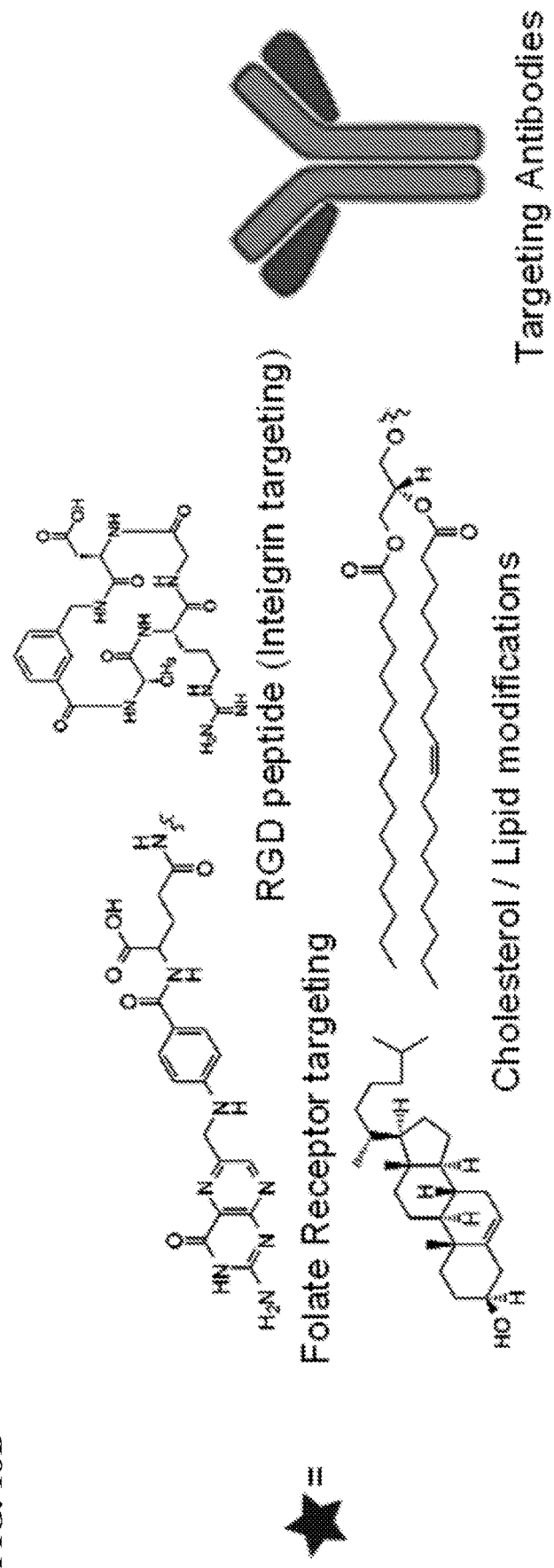
Figure 19A:
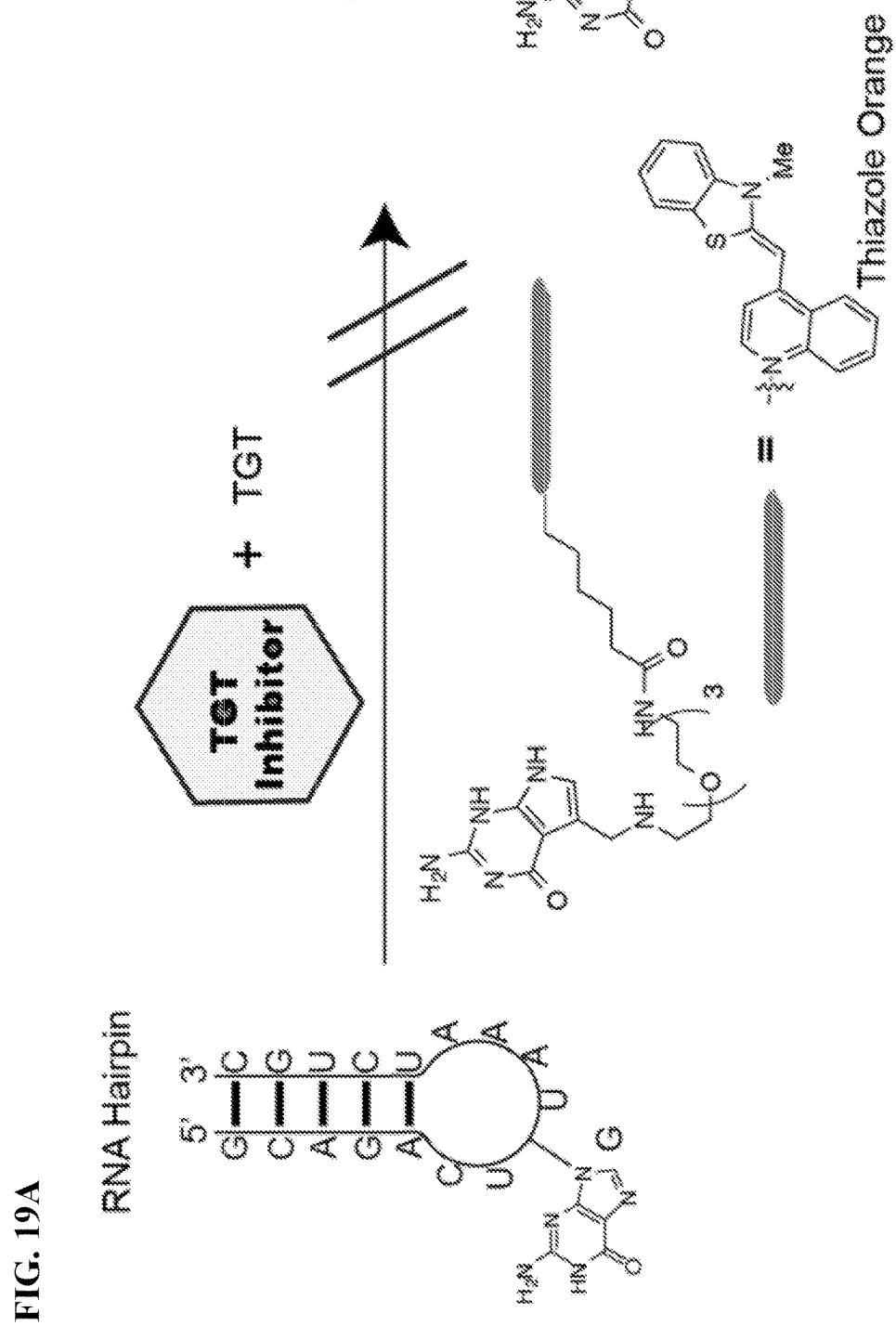

Transcript labeling with PreQ$_1$-Biotin should allow for effective pull down assays with avidin based solid support beads. We subjected both mCherry-TAG and mCherry-TAGΔC to TGT labeling with PreQ$_1$-Biotin. The RNA was subsequently treated with streptavidin-linked DYNA-BEADS®. The beads were then washed extensively and the bound RNA was recovered and analyzed using gel electrophoresis. We observed a single RNA band corresponding to transcript only when mCherry transcript contained the ECY-A 1 hairpin in its 3' UTR (FIGS. 3C and 10). This demonstrates that RNA-TAG could have application for the isolation of specific RNA transcripts genetically encoded with the minimal ECY-A 1 hairpin.

Figure 4:
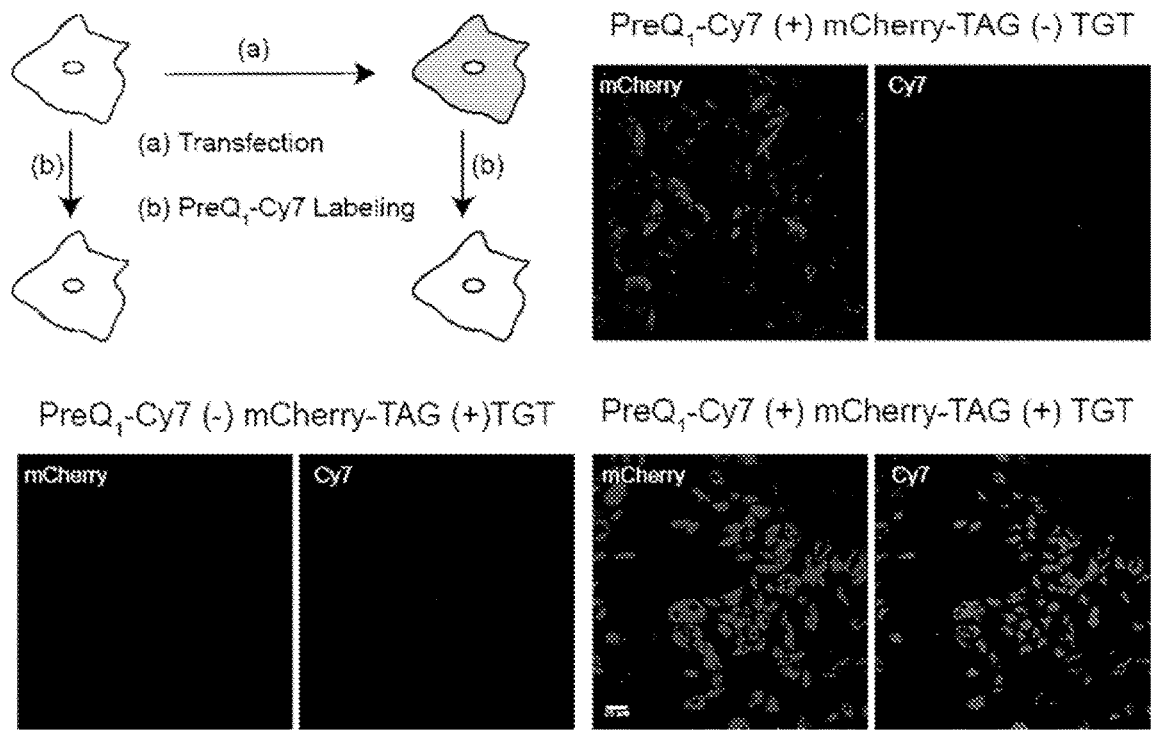
FIG. 4. Labeling of mCherry-TAG RNA endogenously expressed in CHO cells. CHO cells were transfected with a plasmid expressing mCherry-TAG RNA for 16 hr at 37° C. Cells were fixed, permeabilized, and then treated with PreQ1-Cy7 and TGT for 4 hr at 37° C., subsequently washed with PBS and imaged.
Figure 5:
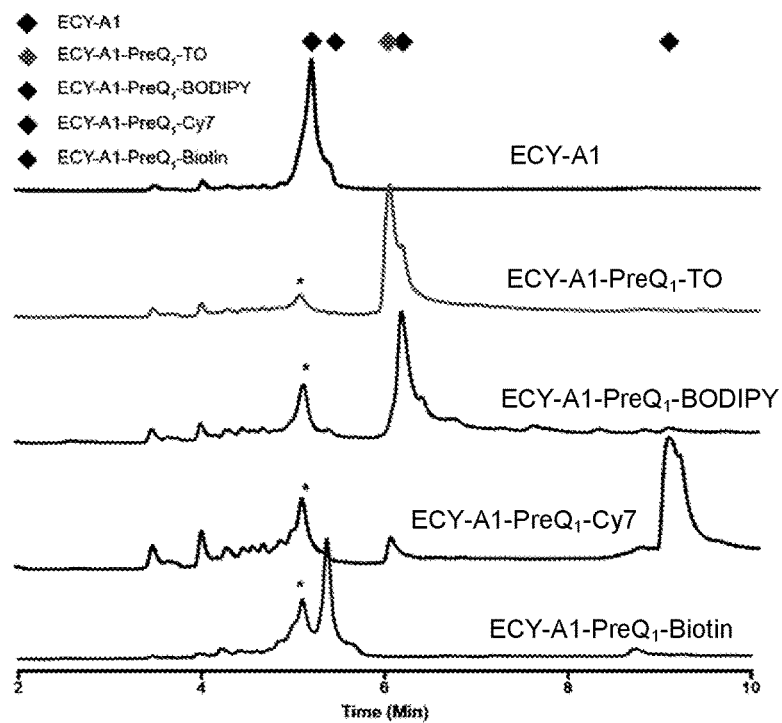
FIG. 5. HPLC traces of ECY-A1 treated with TGT and PreQ1 analogs. LC Chromatograms of TGT labeling of ECY-A1 with PreQ1 analog probes after 6 hour incubation at 37° C. Chromatograms shown were recorded at 260 nm. Colored diamonds denote product peak. Asterisk (*) denotes no starting material RNA mass was observable. Biotin required a 24 hour reaction time for completion. Injection front omitted from plots to clarify product peaks.

Given the substrate specificities of bacterial and eukaryotic TGTs, it may be possible to selectively label RNA in eukaryotic cells using RNA-TAG. To test if cellular imaging is possible, we transiently transfected Chinese hamster ovary (CHO) cells with plasmids coding for mCherry-TAG. After verifying transfection by detecting the expression of mCherry by fluorescence microscopy, we fixed and permeabilized the CHO cells and incubated them with 1 µM TGT and 50 µM PreQ$_1$-Cy7. We also performed controls where cells were not administered TGT or transfected with the mCherry-TAG plasmid. We observed significantly greater staining of fixed cells when treated with both TGT and mRNA plasmid. This suggests that endogenous mRNA labeling and imaging is possible using RNA-TAG (FIG. 4).

In summary, we demonstrate that RNA-TAG is able to site-specifically modify RNAs using PreQ$_1$ analogs possessing large functional groups such as fluorophores and affinity ligands. The RNA-TAG methodology should be useful for imaging applications, and may also play a key role in discovering new RNA-protein interactions, drug screening applications (e.g., high throughput screening), exploring RNA lifetime dynamics, and the like.

Experimental Section

General Information. All reagents used for the synthesis of PreQ1 analogs were purchased from Sigma-Aldrich (St. Louis, Mo.) or Acros Organics (Geel, Belgium) and used without further purification. Thiazole Orange (TO) carboxylic acid was purchased from Octava Chemicals (Toronto, Canada). NHS-Ester molecular probes were purchased from Life Technologies (Carlsbad, Calif.) or Lumiprobe (Hannover, Germany) All DNA and RNA Oligonucleotides and synthetic gene blocks were purchased as custom syntheses from Integrated DNA Technologies (Coralville, Iowa). All restriction enzymes, bio-reagents, nucleotide stains, and competent bacterial strains were purchased from New England Biolabs (Ipswitch, Mass.), Promega (Madison, Wis.), or Life Technologies (Carlsbad, Calif.). Custom gene synthesis for the tRNA Guanine Transglycosylase (TGT) enzyme was ordered and synthesized by Genscript (Piscataway, N.J.). Reactions were monitored by thin layer chromatography using Merck silica gel 60 F254 plates. Reaction mixtures were visualized on TLC plates by UV irradiation or by treatment with KMnO$_4$ and I$_2$. $^1$H and $^{13}$C NMR spectra were recorded on a Varian VX 500 NMR Spectrometer. Chemical shifts are reported in ppm using TMS or the residual peak from the NMR solvent as a reference. Liquid Chromatography with tandem low resolution mass spectra were acquired with an Agilent Infinity 1260 LC and tandem Agilent 6120 Quadrapole mass spectrometer (Santa Clara, Calif.). High resolution mass spectroscopy was collected on an Agilent Infinity 1260 LC and tandem Agilent 6230 high resolution time of flight (TOF) mass spectrometer managed by the UCSD Department of Chemistry and Biochemistry Molecular Mass Spectroscopy Facility. Reverse-phase HPLC purification and analysis was performed using an Agilent 1260 Infinity HPLC with an Agilent Zorbax SB-C18 semi-prep column (ID 9.4×250 mm, 5 µm, 80 Å) using a water/methanol gradient containing 0.1% TFA. Oligonucleotide HPLC analysis was carried out on a Phenomenex Clarity Oligo-MS analytical column (ID 2.1×50 mm, 2.6 µm, 100 Å) using a gradient of water containing 20% hexafluoroisopropanol (HFIP) and 0.1% TEA and methanol containing no additives. Fluorescence measurements were collected either on a Horiba Fluoromax-P spectrometer (for spectral analysis) (Kyoto, Japan) or a Tecan Saphire-II plate reader (for kinetic analysis) (Tecan, Männedorf, Switzerland). Absorbance measurements were obtained with a Thermo Scientific Nano-Drop 2000c UV-Vis spectrophotometer (Waltham, Mass.). All polyacrylamide gels were imaged either on a Bio-Rad ChemiDoc-MP gel imager (Bio-Rad, Hercules, Calif.) or a Maestro™ In Vivo Imaging System (CRI, Woburn, Mass.).

Buffers

TGT Lysis Buffer: 20 mM Tris pH 7.9, 500 mM NaCl, and 100 µM PMSF

T7-RNAP Lysis Buffer: 50 mM phosphate buffer, pH 8.0, 300 mM NaCl, 5 mM BME, 5% glycerol (v/v), and 100 µM PMSF TGT Storage Buffer: 25 mM HEPES, pH 7.3, 2 mM DTT, 1 mM EDTA, and 100 µM PMSF.

TGT Reaction Buffer: 100 mM HEPES, pH 7.3, 5 mM DTT, and 20 mM MgCl$_2$.

T7 Reaction Buffer: 40 mM Tris pH 7.5, 5 mM DTT, 25 mM MgCl$_2$, 2 mM spermidine.

TBE Buffer: (10x stock) 108 g Tris base, 55 g boric acid, 7.5 g EDTA in 1 L Milli-Q water.

2X RNA Loading Buffer: 95% Formamide, 0.02% SDS, 0.02% bromophenol blue, 0.01% xylene cyanol, 1 mM EDTA Streptavidin pull-down Binding and Washing (B&W Buffer): 5 mM Tris-HCl, pH 7.5, 0.5 mM EDTA, 1 M NaCl, 0.05% Tween Chemical Synthesis.

Synthesis of PreQ$_1$-PEG3—NHBoc 1:

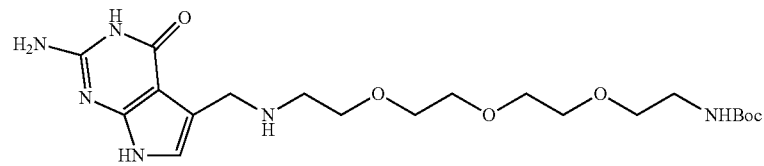 [SMILES: CC(C)(C)OC(=O)NCCOCCOCCOCCNCc1c[nH]c2nc(N)[nH]c(=O)c12]

PreQ$_1$ dihydrochloride (Sigma-Aldrich, St. Louis, Mo.) (7.4 mg, 0.029 mmol) was suspended in 150 µL anhydrous DMF. DBU (13.7 mg, 0.09 mmol) was added to the mixture, followed by N-Boc-PEG3-bromide (BP-22234, Broadpharm, San Diego, Calif.) (12.5 mg, 0.035 mmol). The mixture was heated at 65° C. overnight. Solvent was removed in vacuo and the residue was purified by column chromatography (DCM: MeOH: 30% NH$_4$OH=7:1:0.1) to yield 4.13 mg (31%) of 1 as a light yellow oil. $^1$H NMR (500 MHz, D$_2$O) δ 6.87 (d, J=4.0 Hz, 1H), 4.23–4.11 (m, 2H), 3.80–3.48 (m, 12H), 3.20 (q, J =5.6 Hz, 2H), 3.14 (q, J =4.7 Hz, 2H), 1.49–1.32 (m, 9H). $^{13}$C NMR (126 MHz, D$_2$O) δ 163.32, 158.09, 154.58, 151.68, 117.84, 110.77, 98.81, 80.89, 69.58, 69.58, 69.48, 69.33, 69.33, 67.08, 45.92, 43.53, 39.58, 27.58, 27.58, 27.58. HRMS [M+H]$^+$ m/z calcd. for [C$_{20}$H$_{35}$N$_6$O$_6$]$^+$ 455.2613, found 455.2615 (Δ=0.4 ppm).

Synthesis of PreQ$_1$-PEG3—NH$_2$ 2:

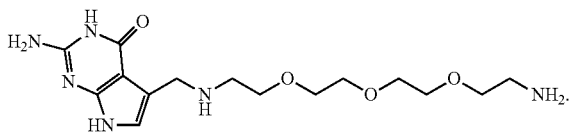 [SMILES: NCCOCCOCCOCCNCc1c[nH]c2nc(N)[nH]c(=O)c12]

PreQ$_1$-PEG3-NHBoc 1 (2 mg) was dissolved in 1 mL DCM, 0.6 mL TFA was slowly added. The mixture was stirred at room temperature for 1 hr. The solution was concentrated in vacuo. The resulting yellow oil was used in the next reaction without further purification.

General Procedure for synthesis of fluorophore or biotin modified PreQ$_1$. PreQ$_1$-PEG 3—NH$_2$ 2 (1 eq.) was dissolved in DMF to give a final concentration of 300 mM. Triethylamine (5 eq.) was added to the mixture, followed by a solution of the corresponding NHS Ester (1 eq.) in DMF. The mixture was stirred at room temperature for 30 minutes. Upon the completion of the reaction, the solvent was removed in vacuo and the mixture was purified by preparative TLC or HPLC.

PreQ$_1$-BODIPY 3:

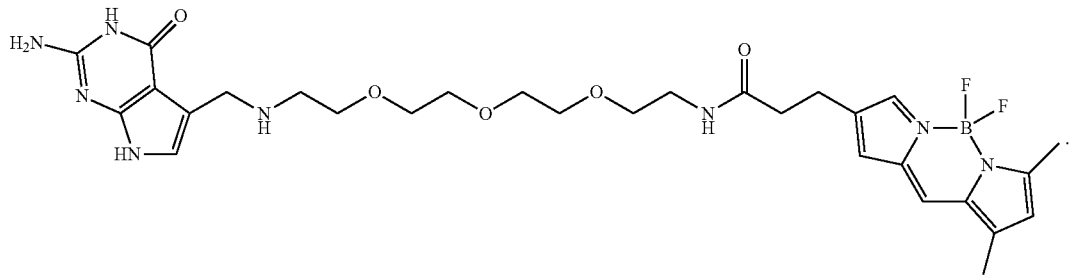

0.9 mg of 2 and BODIPY NHS Ester (D-2184, Molecular Probes, Eugene, Oreg.) yielded 1.3 mg (82%) of 3 as an orange solid. 3 was purified by using preparative TLC (DCM: MeOH: 30% NH$_4$OH=10:1: 0.1). $^1$H NMR (500 MHz, D$_2$O) δ 7.20 (d, J=6.7 Hz, 1H), 6.98 (dd, J=5.2, 3.9 Hz, 1H), 6.76 (s, 1H), 6.36 (t, J=3.8 Hz, 1H), 6.24 (d, J=3.6 Hz, 1H), 4.07 (dt, J=3.9, 1.9 Hz, 2H), 3.78–3.61 (m, 12H), 3.46 (t, J=5.0 Hz, 2H), 3.22–3.11 (m, 4H), 2.70 (t, J=7.7 Hz, 2H), 2.46 (s, 3H), 2.22 (d, J=3.7 Hz, 3H). $^{13}$C NMR (126 MHz, D$_2$O) δ 174.97, 161.17, 160.84, 155.37, 152.55, 151.13, 146.14, 135.15, 132.87, 128.28, 124.04, 120.77, 119.00, 116.23, 98.31, 69.74, 69.62, 69.56, 69.45, 68.97, 65.43, 62.51, 45.53, 42.91, 39.03, 34.75, 24.21, 14.06, 10.44. HRMS[M+H]$^+$ m/z calcd. for [C$_{29}$H$_{39}$BF$_2$N$_8$O$_5$] 628.3214, found [M+H] 628.3212 (Δ=0.3 ppm).

PreQ$_1$-PEG3-Biotin 4:

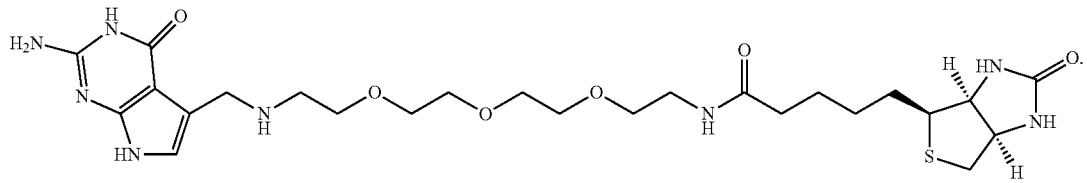 [SMILES: Nc1nc2[nH]cc(CNCCOCCOCCOCCNC(=O)CCCC[C@@H]3SC[C@@H]4NC(=O)N[C@@H]43)c2c(=O)[nH]1]

0.9 mg of 2 and biotin NHS Ester (H1759, Sigma-Aldrich, St. Louis, Mo.) yielded 1.3 mg (88%) of 4 as a white solid. 4 was purified by using preparative TLC (DCM:MeOH: 30% NH$_4$OH=15:1:0.1). $^1$H NMR (500 MHz, D$_2$O) δ 6.91 (s, 1H), 6.91 (s, 0H), 4.57–4.49 (m, 1H), 4.33–4.27 (m, 3H), 3.75 (t, J=4.9 Hz, 2H), 3.67–3.57 (m, 8H), 3.52 (t, J=5.3 Hz, 2H), 3.31×3.23 (m, 4H), 3.20 (dt, J=9.6, 5.2 Hz, 1H), 2.90 (dd, J=13.1, 5.0 Hz, 1H), 2.69 (d, J=13.0 Hz, 1H), 2.15 (t, J=7.3 Hz, 2H), 1.67×1.39 (m, 4H), 1.34×1.22 (m, 2H). $^{13}$C NMR (126 MHz, D$_2$O) δ 176.69, 165.18, 161.26, 152.81, 151.47, 119.35, 107.68, 98.38, 69.57, 69.51, 69.51, 69.27, 68.76, 65.37, 61.92, 60.11, 55.22, 45.73, 43.11, 39.56, 38.72, 35.28, 27.77, 27.55, 25.01. HRMS [M+H]$^+$ m/z calcd. for [C$_{25}$H$_{41}$N$_8$O$_6$S]$^+$ 581.2864, found 581.2863 (Δ=0.2 ppm).

PreQ$_1$-PEG3-Cy7 5:

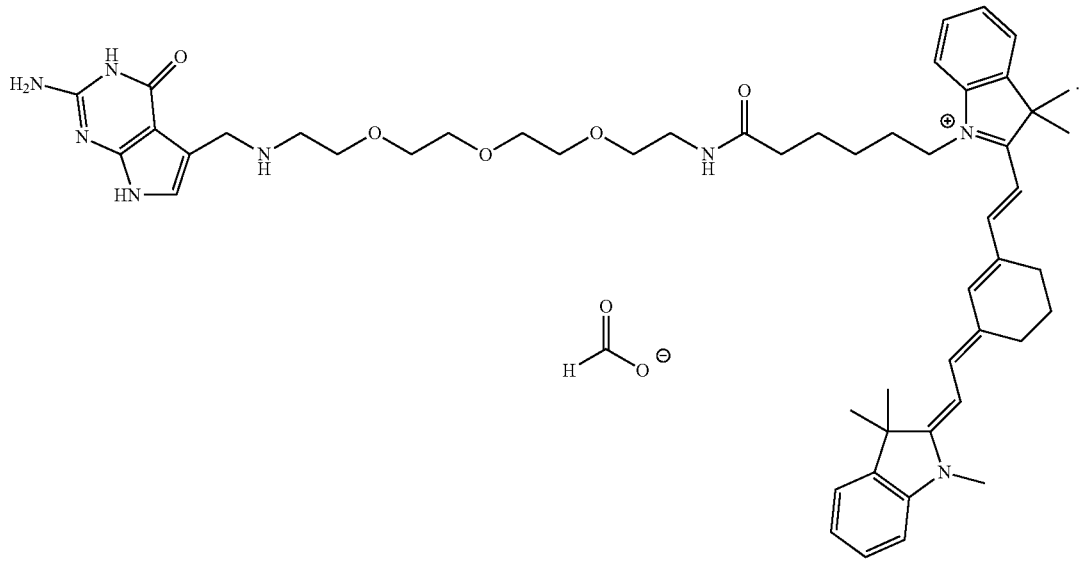

1 mg of 2 and Cy7 NHS Ester (25020, Lumiprobe, Germany) yielded 1.3 mg (52%) of 5 as a dark blue solid. 5 was purified by reverse phase HPLC. $^1$H NMR (500 MHz, CD$_3$OD) δ 7.91–7.66 (m, 2H), 7.64–7.34 (m, 5H), 7.34–7.16 (m, 4H), 6.84 (s, 1H), 6.23–6.09 (m, 2H), 4.29 (s, 2H), 4.09 (t, J=7.3 Hz, 2H), 3.80–3.44 (m, 15H), 3.24 (t, J=4.9 Hz, 2H), 2.56 (q, J=6.2 Hz, 4H), 2.21 (t, J=7.3 Hz, 2H), 2.01–1.89 (m, 2H), 1.89–1.78 (m, 2H), 1.78–1.59 (m, 14H), 1.52–1.40 (m, 4H). $^{13}$C NMR (126 MHz, CD$_3$OD) δ 175.91, 173.79, 172.41, 167.82, 162.60, 156.65, 154.58, 153.92, 150.30, 150.16, 149.37, 144.38, 143.83, 142.32, 133.86, 133.63, 129.71, 126.01, 125.77, 123.35, 123.25, 123.21, 119.30, 111.59, 109.72, 101.00, 100.51, 99.79, 71.56, 71.49, 71.43, 71.19, 70.56, 67.12, 67.06, 67.00, 47.35, 44.78, 44.73, 44.63, 40.23, 36.63, 31.43, 28.05, 28.02, 27.98, 27.89, 27.86, 27.48, 26.52, 24.97, 22.74. HRMS [M+H]$^{2+}$/2 m/z calcd. for [C$_{52}$H$_{71}$N$_8$O$_5$]$^+$ 443.2729, found 443.2726. (Δ=0.7 ppm).

Synthesis of PreQ$_1$-PEG3-Thiazole Orange 6:

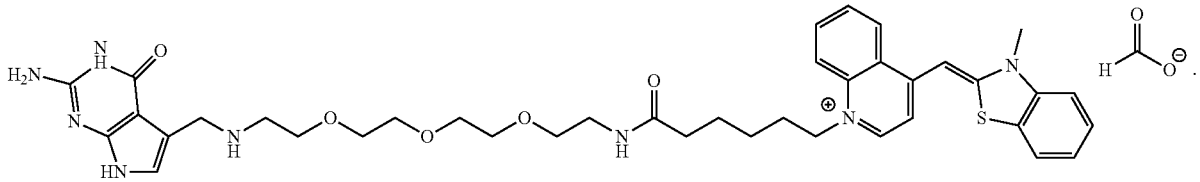

3 mg of (Z)-1-(5-carboxypentyl)-4-(3-methylbenzo[d]thiazol-2(3H)-ylidene)methyl)quinolin-1-ium bromide (Otava Chemicals, Canada) was dissolved in 0.5 mL DMF, followed by the addition of 2.2 mg HATU and 7 μL of DIEA. The mixture was stirred at room temperature for 10 min, before the addition of 2 mg of 2. The mixture was stirred for 1 hr. Upon completion of the reaction, the mixture was concentrated in vacuo and the residue was purified by reverse phase HPLC. The 3.6 mg (62%) of product 6 was collected as an orange solid. $^1$H NMR (500 MHz, CD$_3$OD) δ 8.67 (d, J=8.6 Hz, 1H), 8.43 (d, J=7.2 Hz, 1H), 8.07 (d, J=8.6 Hz, 1H), 7.98 (t, J=7.4 Hz, 0H), 7.91 (d, J=7.9 Hz, 1H), 7.76 (t, J=7.4 Hz, 1H), 7.69 (d, J=8.2 Hz, 1H), 7.63 (t, J=7.9 Hz, 1H), 7.49 (d, J=7.0 Hz, 1H), 7.44 (t, J=7.4 Hz, 1H), 6.94 (s, 1H), 6.82 (s, 1H), 4.60 (t, J=7.1 Hz, 2H), 4.26 (s, 2H), 4.02 (s, 3H), 3.81–3.46 (m, 12H), 3.23 (t, J=4.9 Hz, 2H), 2.22 (t, J=7.1 Hz, 2H), 2.00 (q, J=7.6 Hz, 2H), 1.70 (q, J=7.8 Hz, 2H), 1.46 (q, J=8.1 Hz, 2H), 1.30 (s, 2H). $^{13}$C NMR (126 MHz, CD$_3$OD) δ 178.32, 164.98, 164.65, 156.98, 156.34, 153.48, 147.43, 144.44, 141.25, 136.93, 131.95, 130.59, 129.08, 128.66, 128.38, 128.13, 126.11, 121.67, 121.36, 116.18, 112.21, 112.09, 102.19, 91.70, 73.99, 73.91, 73.85, 73.60, 72.99, 69.52, 58.25, 49.80, 47.22, 42.67, 39.00, 36.53, 32.45, 29.50, 28.69. HRMS [M]$^+$ m/z calcd. for [C$_{39}$H$_{49}$N$_8$O$_5$S]$^+$ 741.3541, found 741.3543 (Δ=0.3 ppm).

Plasmids.

TGT enzyme plasmid. The sequence of *E.coli* TGT (SEQ ID NO: 1) was written into a custom synthesis within a pUC19 vector from Genscript USA Inc. (Piscataway, N.J.). The gene was then cloned out using standard PCR with flanking upstream PstI and downstream HindIII cut sites. The PCR product was purified using the Q1Aquick PCR Purification Kit (Qiagen, Venlo, Limburg Netherlands). The PCR product was subsequently inserted between PstI and HindIII within a derivative based upon pUCIDT-Kan. BL21 *E. coli* competent cells (Life Technologies, Carlsbad, Calif.) were then transformed with the ligation product and screened against kanamycin on agar plates overnight. Colonies were selected and overgrown, and the overgrowth was subjected to DNA extraction with a QIAGEN Plasmid Mini Kit (Qiagen, Venlo, Limburg Netherlands) and sequencing was performed to verify the inserted gene.

mCherry Plasmids mCherry-TAG plasmid. A synthetic gene block containing the sequence for mCherry was designed and ordered from IDT (Coralville, Iowa). Specifically the gene was designed with the ECY-A1 hairpin downstream of mCherry flanked by two 40 nt spacers designed to have minimal secondary structure when transcribed into RNA (SEQ ID NO:2). The geneblock was cloned into a mammalian expression vector pSNAPf (NEB, Ipswitch, Mass.) between cut sites EcoRV and XhoI. DH5a competent cells (Life Technologies, Carlsbad, Calif.) were then transformed with the ligation product and screened against ampicillin on agar plates overnight. Colonies were selected and overgrown, and the overgrowth was subjected to DNA extraction with a QIAGEN Plasmid Maxi Kit (Qiagen, Venlo, Limburg Netherlands) and sequencing was performed to verify the inserted gene.

mCherry-TAGΔC plasmid. The G to C replacement variant was constructed by using a primer "cgcagactctaaatctgcccccatg" (SEQ ID NO:3) based on the hairpin recognition element of the bacterial tRNA guanine transglycosylase with a single base change GΔC. The primer and its complement was first re-suspended at 20 μM in CutSmart® buffer in the presence of T4 ligase and NsiI (NEB, Ipswitch, Mass.) to prevent any reverse ligations. After 20 min at RT, the enzymes where heat inactivated and the mixture was used as the primers for the amplification of mCherry-TAG by polymerase chain reaction (PCR) using KOD Hot Start polymerase (Merck, Kenilworth, N.J.) according to the manufacture's protocol. The PCR product was first gel purified using QIAquick Gel Extraction Kit (Qiagen, Venlo, Limburg Netherlands) and then inserted in between an EcoRV and an Xho1 site of a PsnapF vector (NEB, Ipswitch, Mass.). Colonies were selected and screened for those containing GΔC point mutation with an fspI cut site just after the incorporated ECY-A1ΔC hairpin (SEQ ID NO:4).

Protein Expression and Purification

TGT Enzyme. The TGT Enzyme was expressed and purified adapting a previously described literature procedure.[1] BL21 cells previously transformed with the TGT enzyme plasmid described above were seeded into two one-liter culture flasks containing 50 μg/mL kanamycin in freshly autoclaved LB media. The cultures were placed in a shaker/incubator and incubated at 37° C. until the optical cell density reached OD ~0.6 AU. Expression was then induced via inoculation with IPTG (Teknova, Hollister, Calif.) at a final concentration of 1 mM, and the cells continued to incubate for an additional 4 hours. Cells were then pelleted at 10,000 RPM for 15 minutes at 4° C. and stored at –20° C. overnight until lysed. Cells were suspended in 10 mL of TGT Lysis Buffer containing 5 mM Imidazole, and passed through a French press for lysis (4 rounds at ~1200 psi). Cellular debris was centrifuged away by spinning at 10,000 g for 30 minutes at 4° C. The supernatant was then mixed with 1 mL of freshly prepared nickel charged HisPur Ni—NTA resin (Thermo Scientific, Waltham, Mass.) that had been pre-equilibrated with TGT lysis buffer containing 5 mM Imidazole and gently shaken at 4° C. for 3 hours. The resin was placed into a column at 4° C. and washed with 20 mL of TGT lysis buffer containing 5 mM Imidazole, followed by 15 mL of wash buffer (TGT lysis buffer+60 mM imidazole). The protein was eluted with 15 mL of elution buffer (TGT lysis buffer+350 mM imidazole). Elution fractions were combined and dialyzed through a 20 kDa MWCO Slide-A-Lyzer dialysis cassette (Thermo Scientific) into TGT storage buffer over 18 hours across 4×500 mL buffer exchanges at 4° C. The enzyme was verified by PAGE gel and distributed into 100 μL aliquots of roughly 1 mg/mL and stored at –80° C. until used.

T7-RNA Polymerase. T7-RNA Polymerase expression plasmid was obtained as BL21 transformed cells. The transformed cells were seeded into a one liter culture flask containing 100 μg/mL carbenicillin in freshly autoclaved LB media. The culture was placed in a shaker/incubator and incubated at 37° C. until the optical cell density reached OD ~0.6 AU. Expression was then induced via inoculation with IPTG at a final concentration of 1 mM, and allowed to continue to incubate for an additional 4 hours. Cells were then pelleted at 10,000 RPM for 15 minutes at 4° C. and stored at –20° C. overnight until lysed. Cells were resuspended in 10 mL of T7-RNAP lysis buffer containing 5 mM Imidazole, and passed through a French press for lysis (4 rounds at ~1200 psi). Cellular debris was centrifuged away by spinning at 10,000 g for 30 minutes at 4 C. The supernatant was then mixed with 1 mL of freshly prepared nickel charged HisPur Ni—NTA resin that had been pre-equilibrated with T7-RNAP lysis buffer containing 5 mM Imidazole and gently shaken at 4° C. for 3 hours. The resin was placed into a column at 4° C. and washed with 10 mL of T7-RNAP lysis buffer containing 10 mM imidazole, followed by 10 mL of T7-RNAP lysis buffer containing 20 mM imidazole. The protein was then eluted with T7-RNAP lysis buffer containing 100 mM imidazole and collected at 4° C. The combined eluent was spin dialyzed with a 50 K MWCO Amicon centrifuge filter (EMD Milipore, Billerica, Mass.) with fresh T7-RNAP lysis buffer lacking imidazole. The polymerase was verified by PAGE gel and distributed into 100μL aliquots of roughly 10 mg/mL and stored at −20° C. until used.

Enzymatic Modification of RNA Oligonucleotides by tRNA Guanine Transglycosylase (TGT)

General TGT reaction with RNA oligonucleotide hairpins TGT reaction conditions were adapted from a previously reported literature procedure.[1] An eppendorf tube containing 10 μM RNA oligonucleotide, 100 μM PreQ1 analog, and 10 μM TGT enzyme were prepared in a final volume of 50 μL of TGT reaction buffer. The reactions were incubated at 37° C. for a minimum of 2 hours. The reactions were halted by chilling samples to 4° C. or freezing at −80° C. until purified or analyzed.

Liquid chromatography and mass spectroscopy analysis of preQ$_1$ modified RNA hairpins. Samples were first prepared according to the general procedure. Samples were allowed to react for 6 hours and frozen at −80° C. until analyzed (PreQ$_1$-Biotin required 24 hours for completion). Samples were diluted 1:2 with milli-Q water and injected onto a clarity Oligo-MS column (Phenomenex, Torrance, Calif.) and analyzed by HPLC according to the following gradient: (A=Milli-Q water containing 20% hexafluoroisopropanol (HFIP) and 0.1% TEA, B=methanol), Initial conditions 95% A, 5% B, hold 2 min then a linear gradient starting at 2 min and ending at 10 min with 45% A, 55% B. Samples were monitored at 260 nm as well as either 505 nm or 700 nm as appropriate when fluorophore PreQ1 analogs were employed. HRMS samples were collected in negative ion mode and analyzed in a similar manner by combining the mass spectrum traces across the peak of interest. Raw mass spectrum were deconvoluted using MagTran software package v. 1.03 b3 (Zhongqi Zhang, Amgen) to calculate the observed parent mass reported in Table 2.

Fluorescence emission spectra of PreQ$_1$-TO probe turn-on with ECY-A1 hairpin. Samples of ECY-A1, ECY-A1ΔC, and ECY-X1 were first prepared in a similar fashion to the general protocol except only 20 μM PreQ$_1$-TO was employed to avoid non-specific binding to the hairpins. Samples were allowed to react for 2 hours, verified to be at completion by HPLC, and diluted 30-fold into TGT reaction buffer. Spectra were then collected on a Fluoromax-P spectrophotometer by excitation at 501 nm and scanning emission from 510 to 600 nm with excitation and emission slit width at 5 nm and an integration time of 1 s. All spectra were background subtracted from TGT reaction buffer and Normalized against the fluorescence intensity values of a sample containing an analogous concentration of PreQ$_1$-TO (0.667 μM) in TGT reaction buffer.

Estimation of PreQ$_1$-TO substrate kinetics with ECY-A1. An estimation of PreQ$_1$-TO substrate kinetics with ECY-A 1 was performed under similar concentrations and conditions to that found from previous kinetic analyses using radiolabeled substrates.[2] A triplicate set of 20 μL reactions was analyzed using a Tecan Saphire-II plate reader in a Greiner 384 well flat bottom plate (VWR, CAT# 89089-584). Each well was prepped with 10 μM ECY-A 1 and a variable amount (from 100 μM to 10 nM in serial ⅓ dilutions) of PreQ$_1$-TO in TGT reaction buffer. The plate was covered and allowed to warm up to 37° C. for 10 minutes. The plate was then placed upon a 37° C. metal sheet and to each well was added TGT enzyme to a final concentration of 100 nM. Each well was then covered with 10 μL of light mineral oil (to prevent evaporation of water) and the plate was immediately subjected to a fluorescence reading for the first kinetic time point at 37° C. Each well was monitored with an excitation of 501 nm and emission of 531. The excitation bandwidth was set to 20 nm and the emission bandwidth was set to 5 nm. The gain was held fixed and the integration time set to 1 second with 10 reads averaged to each data point collected. The sample was monitored for 30 minutes at 37° C. with a reading taken every 2 minutes. The data was worked up using an ECY-A1-PreQ$_1$-TO calibration curve to convert fluorescence into concentration of product in each sample for each time point to achieve an estimation of the initial rate of each reaction in $M^{-1}/s^{-1}$. The data was plotted in Graph Pad Prism v. 6.0a (La Jolla, Calif.) and the slope of each line resulting from each concentration was taken to be the initial rate. The initial rates were then plotted against the concentration of substrate to achieve a standard kinetic curve. This curve was analyzed with Graph Pad Prism v. 6.0a utilizing the "Enzyme Kinetics-Substrate v Velocity kcat" curve fitting package to obtain the reported $K_m$ and $K_{cat}$.

Streptavidin gel shift of RNA hairpins. ECY-A1 RNA and ECY-A1ΔC was incubated in a mixture of 10 μM RNA, 100 μM preQ$_1$-Biotin, and 1 μM TGT (omitted in control samples) in TGT reaction buffer at 37° C. for 24 hours. After the reactions were complete, the RNA was precipitated by addition of 10% volume of 3M sodium acetate and 2.5 volumes 95% ethanol and incubation at −20° C. overnight. After centrifugation at 4° C. (16,100 g, 30 min), the resulting RNA pellet was resuspended in water, and the concentration of RNA was quantified. The prepared RNA was then incubated in the presence of streptavidin (Life Technologies, Carlsbad, Calif.) at 37° C. for 1 hour in a mixture containing the following: 10 mM Tris (pH 8.1), 2.5 μM RNA, and 50 μM streptavidin. 1X RNA loading dye (NEB, Ipswitch, Mass.) was added to the sample (without heat denaturation) and samples were analyzed by 15% denaturing PAGE.

RNA Transcript Synthesis.

DNA plasmid template was first cut to ensure uniform length transcriptions. mCherry-TAG plasmid was digested by EcoRV and XhoI, while mCherry-TAGΔC was digested by EcoRV and FspI. Approximately 50 ng of intact plasmid was dissolved in CutSmart Buffer to a final concentration of roughly 500 ug/mL and 50 units of each enzyme were added. The solution was heated at 37° C. for 2 hours and cooled to room temperature. The DNA was extracted with equal volume of molecular biology grade phenol/chloroform/isoamyl alcohol (25:24:1) (Sigma) and vortexed for 2 minutes followed by a 5 min centrifuge at 10,000 g. 85% of the top aqueous layer was carried to a fresh tube and an equal portion of chloroform was added and again vortexed for 2 minutes followed by 5 minutes of centrifugation at 10,000 g. 75% of the aqueous layer was placed into a fresh tube for DNA precipitation. The cut DNA was precipitated by addition of 10% volume of 3M sodium acetate pH 5.2 and 2.5 volumes of 95% ethanol. The sample was chilled to −20° C. for one hour, centrifuged at 16,100 g for 20 minutes at 4° C., and ethanol was removed gently via pipette. The DNA pellet was air dried and resuspended in 100 μL of RNAse free molecular biology grade water and used directly in a 1 mL transcription reaction.

Each transcription reaction was setup with approximately 30-40 ng of cut plasmid, 5 mM RNA NTPs (1.25 mM each ATP, CTP, GTP, UTP) (NEB, Ipswitch, Mass.), 1 unit of Thermostable Inorganic Pyrophosphatase (NEB, Ipswitch, Mass.), 57 μg/μL T7-RNAP, and 0.05% Triton X-100 (Sigma, St. Louis, Mo.) in T7 Reaction Buffer. The transcription was run at 37° C. for 3-4 hours and halted over 1 hour at 37° C. by addition of 2.4 μL of 0.5 M CaCl$_2$ followed by 20 Units of Turbo DNAse (Life Technologies, Carlsbad, Calif.). The sample was then treated with 8 Units of Proteinase K (NEB, Ipswitch, Mass.) and incubated an additional 45 minutes at 37° C. The transcription reaction was then centrifuged at max speed for 10 minutes at room temperature to pellet any remaining magnesium pyrophosphate and the supernatant was decanted and spin dialyzed 6×500 L into molecular biology grade RNAse free water via Nanosep 100K Omega spin filter (Pall Corporation, Port Washington, N.Y.). The RNA was quantified at 260 nm, confirmed as a single observable UV shadowing band by 4% denaturing PAGE (4% polyacrylamide in TBE with 8M urea) and kept frozen at −20° C. until used.

TGT in vitro Reactions with RNA Transcripts

General labeling reaction procedure for fluorescence spectra and gel analysis. A 25 μL reaction was setup in a small eppendorf tube containing 100 nM RNA transcript, 50 μM PreQ1 analog, and 1μM TGT in TGT reaction buffer. 1 unit of RNaseIn (Promega, Madison, Wis.) was added to each reaction to prevent degradation of the transcript. The reaction was allowed to proceed for 4 hours, after which the sample was cooled to 4° C. and either used directly or stored at −80° C. until further analyzed.

Gel Analysis of TGT reactions with PreQ1 analogs. To perform the multi-label gel image, mCherry-TAG was labeled according to the general labeling procedure for transcripts with PreQ$_1$-TO, PreQ$_1$-BODIPY, and PreQ$_1$-Cy7. After the reactions were complete, the RNA was precipitated by addition of 10% volume of 3M sodium acetate and 2.5 volumes 95% ethanol. The samples were then precipitated at −80° C. for 2 hours after which they were centrifuged at 16,100 g for 30 minutes at 4° C. The ethanol was carefully pipetted away and the RNA pellet was allowed to air dry for 10 minutes on the bench. The pellet was resuspended in 10 μL of 1X RNA loading dye (NEB, Ipswitch, Mass.), heated to 95° C. for 2 minutes, placed on ice for 20 minutes, and subsequently loaded into a freshly poured denaturing 4% polyacrylamide gel (4% polyacrylamide in 1X TBE buffer with 8% urea) and run at 120 V for approximately 2 hours until the xylene cyanol blue dye had reached the bottom of the gel. The electrophoresis was halted and the gel was imaged using a Maestro™ In Vivo Imaging System (CRI, Woburn, Mass.) with both a GFP filter set (for BODIPY and TO imaging) and a Cy7 filter set (for Cy7 imaging). The images were merged and false colored accordingly to achieve the multi-colored gel image. The gel was then stained with methylene blue (0.02% methylene blue (Sigma) in 0.4 M sodium acetate pH 5.5) for 30 minutes, followed by an overnight destain in milli-Q water. The gel was then imaged on a white light trans-illuminator with a digital camera.

To determine the specificity of TGT for the ECY-A1 loop within full length transcripts, PreQ$_1$-BODIPY was reacted with either mCherry-TAG or mCherry-TAGΔC in the presence and absence of TGT enzyme as previously described. The samples were then precipitated and run on a 4% denaturing polyacrylade gel as described and imaged first using a Bio-Rad ChemiDoc-MP imager (Bio-Rad, Hercules, Calif.), and then treated with methylene blue and imaged as described.

Fluorescence emission spectra of PreQ$_1$-TO probe turn-on with mCherry-TAG RNA. Fluorescence emission spectra were collected in a similar fashion to that described previously for the short RNA hairpins. 25 μL reactions were setup with 10 μM TGT enzyme, 20 μM PreQ$_1$-TO, and 100 nM transcript RNA and incubated at 37° C. for 2 hours. Samples were then diluted 30-fold and measured under the same conditions and parameters as that of the short hairpins.

DYNABEADS® Streptavidin pull-down of PreQ$_1$-Biotin modified transcripts. mCherry-TAG and mCherry-TAGΔC transcripts was incubated in a mixture of 1 μM RNA, 100 μM preQ$_1$-Biotin, and 1 μM TGT (omitted in control samples) in TGT reaction buffer at 37° C. for 4 hours. 1 unit of RNAseIn (Promega, Madison, Wis.) was added to the reaction to prevent transcript degradation. Samples were drop dialyzed through 0.02 μm MF-Millipore membrane filter (Millipore, Billerica, Mass.) using 25 mL Milli-Q water and subsequently ethanol precipitated by addition of 10% volume of 3M sodium acetate and 2.5 volumes 95% ethanol and incubation at μ20° C. overnight. After centrifugation at 4° C. (16,100 g, 30 min), the resulting RNA pellet was resuspended in water, and the concentration of RNA was quantified.

Streptavidin M280 DYNABEADS® (Life Technologies, Carlsbad, Calif.) were washed according to manufacturer's instructions for RNA applications using binding and washing (B&W) buffer. Beads were blocked in B&W buffer with yeast tRNA (0.1 mg/100 uL of beads). Following the blocking step, beads were washed twice with B&W buffer. Pull down was then performed by incubation of 1 μg of prepared RNA with 10 uL of washed beads in B&W buffer at room temperature for 30 minutes with constant rotation. The beads were then washed three times with B&W buffer. Elution of bound RNA from beads was achieved by incubation in 2X RNA loading dye (NEB, Ipswitch, Mass.) for 3 min at 96° C. Samples were then analyzed by 4% denaturing PAGE.

Fixed Cell Labeling of Endogenously Expressed mCherry-ECY-A1 Transcript. Chinese Hamster Ovary (CHO) cells (CRL-9606, ATCC, Manassas, Va.) were cultured in Ham's F-12K media (Life Technologies, Carlsbad, Calif.) and kept under 20 passages from the ATCC standard line. CHO cells were plated at an initial density of 10,000 cells per well in a Nunc Lab-Tek 8 well chamber slide (Thermo Scientific, Waltham, Mass.). Cells were allowed to adhere overnight and washed with Opti-MEM media (Life Technologies, Carlsbad, Calif.) and subsequently transfected with 0.5 ng of mCherry-TAG plasmid per well with 1.5 μL of Lipofectamine® 2000 (Life Technologies, Carlsbad, Calif.) in Opti-MEM as per manufacture's protocol. Control wells lacking transfection were treated and washed with Opti-MEM in the absence of DNA and lipofectamine®. After overnight transfection, the cells were washed twice with PBS (200 μL each) and fixed with 100 μL of a 3.7% paraformaldehyde in PBS solution for 10 minutes at room temperature. Cells were then permeabilized by treatment with 100 μL of 0.1% Triton X-100 in PBS for 20 minutes at room temperature and washed 2×200 μL with fresh PBS. Cells were then treated for four hours at 37° C. with 100 μL of TGT reaction buffer containing 50 μM PreQ$_1$-Cy7 either with or without 10 μM TGT enzyme added. The cells were washed 2×100 μL of PBS and imaged. Images were acquired on a confocal laser scanner FV1000 (Olympus, Japan) built around an Olympus IX81 inverted microscope (Olympus, Japan) with a 40x, 1.30 NA oil immersion objective using the FLUOVIEW software package (Olympus, Japan). The Cy7 near infrared fluorescent probe was excited with a 633 nm HeNe laser, and the mCherry fluorescent protein was excited with a 543 nm HeNe laser. Images were subsequently analyzed and processed using ImageJ (NIH, rsbweb.nih.gov).

Scheme 1. Exemplary synthesis of analogs of PreQ1

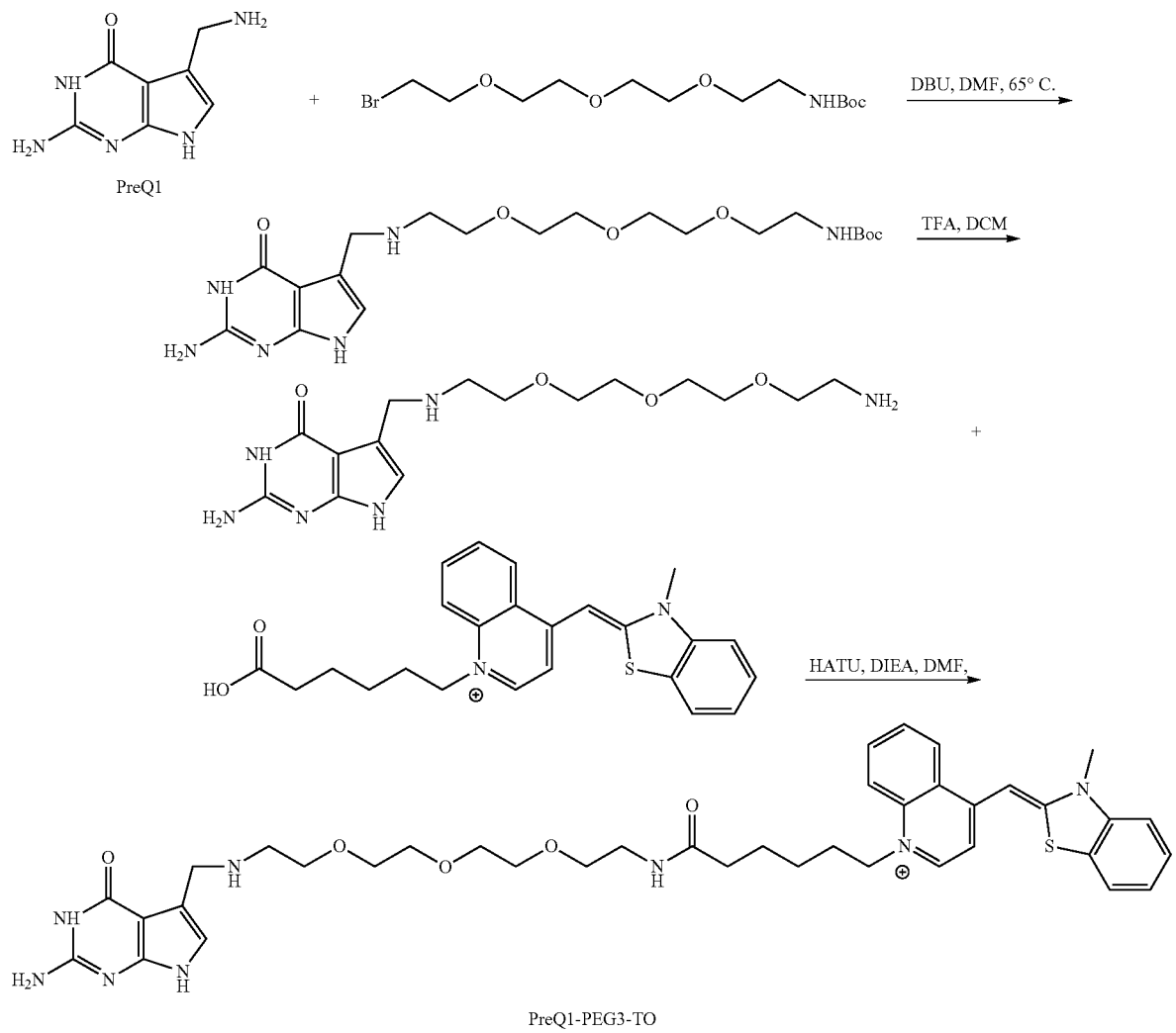

What is claimed is:

1. A compound of structural Formula II:

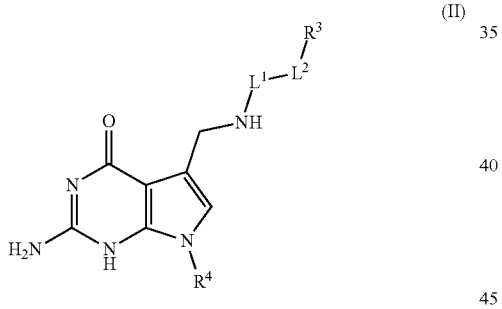

or a pharmaceutically acceptable salt thereof, wherein:

$L^1$ is $R^5$-substituted alkylene, $R^5$-substituted or unsubstituted heteroalkylene, a detectable moiety, $R^5$-substituted or unsubstituted cycloalkylene, $R^5$-substituted or unsubstituted heterocycloalkylene, $R^5$-substituted or unsubstituted arylene, or $R^5$-substituted or unsubstituted heteroarylene;

$R^5$ is independently halogen, —$CF_3$, —CN, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^6$-substituted or unsubstituted alkyl, $R^6$-substituted or unsubstituted heteroalkyl, $R^6$-substituted or unsubstituted cycloalkyl, $R^6$-substituted or unsubstituted heterocycloalkyl, $R^6$-substituted or unsubstituted aryl, or $R^6$-substituted or unsubstituted heteroaryl;

$R^6$ is independently, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^7$-substituted or unsubstituted alkyl, $R^7$-substituted or unsubstituted heteroalkyl, $R^7$-substituted or unsubstituted cycloalkyl, $R^7$-substituted or unsubstituted heterocycloalkyl), $R^7$-substituted or unsubstituted aryl, or $R^7$-substituted or unsubstituted heteroaryl;

$L^2$ is $R^8$-substituted alkylene, $R^8$-substituted or unsubstituted heteroalkylene, a detectable moiety, $R^8$-substituted or unsubstituted cycloalkylene, $R^8$-substituted or unsubstituted heterocycloalkylene, $R^8$-substituted or unsubstituted arylene, or $R^8$-substituted or unsubstituted heteroarylene;

$R^8$ is independently halogen, —$CF_3$, —CN, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^9$-substituted or unsubstituted alkyl, $R^9$-substituted or unsubstituted heteroalkyl, $R^9$-substituted or unsubstituted cycloalkyl, $R^9$-substituted or unsubstituted heterocycloalkyl, $R^9$-substituted or unsubstituted aryl, or $R^9$-substituted or unsubstituted heteroaryl;

$R^9$ is independently halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{10}$-substituted or unsubstituted alkyl, $R^{10}$-substituted or unsubstituted heteroalkyl, $R^{10}$-substituted or unsubstituted cycloalkyl $R^{10}$-substituted or unsubstituted heterocycloalkyl, $R^{10}$-substituted or unsubstituted aryl, or $R^{10}$-substituted or unsubstituted heteroaryl;

$R^3$ is a detectable moiety, a biomolecule, hydrogen, halogen, —CN, $R^{11}$-substituted or unsubstituted alkyl, $R^{11}$-substituted or unsubstituted heteroalkyl, $R^{11}$ substituted or unsubstituted cycloalkyl, $R^{11}$-substituted or unsubstituted heterocycloalkyl, $R^{11}$-substituted or unsubstituted aryl, or $R^{11}$-substituted or unsubstituted heteroaryl;

$R^{11}$ is independently oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, $R^{12}$-substituted or unsubstituted alkyl, $R^{12}$-substituted or unsubstituted heteroalkyl, $R^{12}$-substituted or unsubstituted cycloalkyl, $R^{12}$-substituted or unsubstituted heterocycloalkyl, $R^{12}$-substituted or unsubstituted aryl, or $R^{12}$-substituted or unsubstituted heteroaryl;

$R^{12}$ is independently oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, $R^{13}$-substituted or unsubstituted alkyl, $R^{13}$-substituted or unsubstituted heteroalkyl, $R^{13}$-substituted or unsubstituted cycloalkyl, $R^{13}$-substituted or unsubstituted heterocycloalkyl, $R^{13}$-substituted or unsubstituted aryl, or $R^{13}$-substituted or unsubstituted heteroaryl;

$R^7$, $R^{10}$, and $R^{13}$ are independently oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, or unsubstituted heteroaryl; and $R^4$ is hydrogen or a ribose, wherein the ribose is part of a modified or unmodified RNA molecule, and further wherein the ribose comprises a guanine, wherein the guanine is within a hairpin loop in the RNA molecule.

2. The compound of claim 1, wherein $L^1$ is a substituted unbranched $C_4$-$C_{12}$ alkylene.

3. The compound of claim 1, wherein $R^4$ is a ribose.

4. The compound of claim 1, wherein $R^3$ is a dye, a fluorophore, an affinity ligand, an antibody, a polypeptide, a protein or a nucleic acid molecule.

5. The compound of claim 1, wherein the guanine forms part of a 5' YGU 3' sequence or a 5' UGY 3' sequence within the RNA molecule, wherein Y is a nucleotide or pseudouridine.

6. The compound of claim 5, wherein the 5' UGU 3' sequence is within an RNA hairpin element.

7. The compound of claim 1, wherein the guanine forms part of a 5' ΨGΨ 3' sequence within the RNA molecule.

8. The compound of claim 1, wherein $R^3$ is biocytin, biotin, a boron-dipyrromethene dye, a cyanine dye, a thiazole compound or a thiazole orange derivative.

9. The compound of claim 1, wherein the RNA molecule comprises a 5-methylcytosine, a pseudouridine (Ψ), a 2-thiouridine or any combination thereof.

10. A method of substituting a guanine with a PreQ1 analog within an RNA molecule, comprising
(i) contacting the PreQ1 analog with an RNA molecule in the presence of a transglycosylase; and (ii) allowing the transglycosylase to substitute a guanine moiety from a guanine within the RNA sequence with the PreQ1 analog thereby forming a modified RNA molecule,
wherein the PreQ1 analog is the compound of formula II:

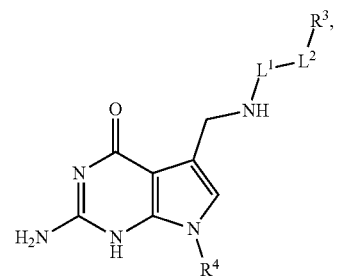

or a pharmaceutically acceptable salt thereof,
wherein:

$L^1$ is $R^5$-substituted alkylene, $R^5$-substituted or unsubstituted heteroalkylene, a detectable moiety, $R^5$-substituted or unsubstituted cycloalkylene, $R^5$-substituted or unsubstituted heterocycloalkylene, $R^5$-substituted or unsubstituted arylene, or $R^5$-substituted or unsubstituted heteroarylene;

$R^5$ is independently oxo, halogen, —CF$_3$, —CN, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, $R^6$-substituted or unsubstituted alkyl, $R^6$-substituted or unsubstituted heteroalkyl, $R^6$-substituted or unsubstituted cycloalkyl, $R^6$-substituted or unsubstituted heterocycloalkyl, $R^6$-substituted or unsubstituted aryl, or $R^6$-substituted or unsubstituted heteroaryl;

$R^6$ is independently oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, $R^7$-substituted or unsubstituted alkyl, $R^7$-substituted or unsubstituted heteroalkyl, $R^7$-substituted or unsubstituted cycloalkyl, $R^7$-substituted or unsubstituted heterocycloalkyl), $R^7$-substituted or unsubstituted aryl, or $R^7$-substituted or unsubstituted heteroaryl;

$L^2$ is $R^8$-substituted alkylene, $R^8$-substituted or unsubstituted heteroalkylene, a detectable moiety, $R^8$-substituted or unsubstituted cycloalkylene, $R^8$-substituted or unsubstituted heterocycloalkylene, $R^8$-substituted or unsubstituted arylene, or $R^8$-substituted or unsubstituted heteroarylene;

$R^8$ is independently oxo, halogen, —CF$_3$, —CN, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, $R^9$-substituted or unsubstituted alkyl, $R^9$-substituted or unsubstituted heteroalkyl, $R^9$-substituted or unsubstituted cycloalkyl, $R^9$-substituted or unsubstituted heterocycloalkyl, $R^9$-substituted or unsubstituted aryl, or $R^9$-substituted or unsubstituted heteroaryl;

R⁹ is independently oxo, halogen, —CF₃, —CN, —OH, —NH₂, —COOH, —CONH₂, —NO₂, —SH, —SO₃H, —SO₄H, —SO₂NH₂, —NHNH₂, —ONH₂, —NHC═(O)NHNH₂, —NHC═(O) NH₂, —NHSO₂H, —NHC═(O)H, —NHC(O)—OH, —NHOH, —OCF₃, —OCHF₂, R¹⁰-substituted or unsubstituted alkyl, R¹⁰-substituted or unsubstituted heteroalkyl, R¹⁰-substituted or unsubstituted cycloalkyl R¹⁰-substituted or unsubstituted heterocycloalkyl, R¹⁰-substituted or unsubstituted aryl, or R¹⁰-substituted or unsubstituted heteroaryl;

R³ is a detectable moiety, a biomolecule, hydrogen, halogen, —CN, R¹¹-substituted or unsubstituted alkyl, R¹¹-substituted or unsubstituted heteroalkyl, R¹¹ substituted or unsubstituted cycloalkyl, R¹¹-substituted or unsubstituted heterocycloalkyl, R¹¹-substituted or unsubstituted aryl, or R¹¹-substituted or unsubstituted heteroaryl;

R¹¹ is independently oxo, halogen, —CF₃, —CN, —OH, —NH₂, —COOH, —CONH₂, —NO₂, —SH, —SO₃H, —SO₄H, —SO₂NH₂, —NHNH₂, —ONH₂, —NHC═(O)NHNH₂, —NHC═(O) NH₂, —NHSO₂H, —NHC═(O)H, —NHC(O)—OH, —NHOH, —OCF₃, —OCHF₂, R¹²-substituted or unsubstituted alkyl, R¹²-substituted or unsubstituted heteroalkyl, R¹²-substituted or unsubstituted cycloalkyl, R¹²-substituted or unsubstituted heterocycloalkyl, R¹²-substituted or unsubstituted aryl, or R¹²-substituted or unsubstituted heteroaryl;

R¹² is independently oxo, halogen, —CF₃, —CN, —OH, —NH₂, —COOH, —CONH₂, —NO₂, —SH, —SO₃H, —SO₄H, —SO₂NH₂, —NHNH₂, —ONH₂, —NHC═(O)NHNH₂, —NHC═(O) NH₂, —NHSO₂H, —NHC═(O)H, —NHC(O)—OH, —NHOH, —OCF₃, —OCHF₂, R¹³-substituted or unsubstituted alkyl, R¹³-substituted or unsubstituted heteroalkyl, R¹³-substituted or unsubstituted cycloalkyl, R¹³-substituted or unsubstituted heterocycloalkyl, R¹³-substituted or unsubstituted aryl, or R¹³-substituted or unsubstituted heteroaryl;

R⁷, R¹⁰, and R¹³ are independently oxo, halogen, —CF₃, —CN, —OH, —NH₂, —COOH, —CONH₂, —NO₂, —SH, —SO₃H, —SO₄H, —SO₂NH₂, —NHNH₂, —ONH₂, —NHC═(O)NHNH₂, —NHC═(O) NH₂, —NHSO₂H, —NHC═(O)H, —NHC(O)—OH, —NHOH, —OCF₃, —OCHF₂, unsubstituted alkyl, unsubstituted heteroalkyl, unsubstituted cycloalkyl, unsubstituted heterocycloalkyl, unsubstituted aryl, or unsubstituted heteroaryl; and R⁴ is hydrogen.

11. The method of claim 10, wherein the guanine is in a 5' UGU 3' sequence, a 5' YGU 3' sequence or a 5' UGY 3' sequence within the RNA molecule, wherein Y is a nucleotide or pseudouridine.

12. The method of claim 10, wherein the RNA molecule comprises modified nucleobase.

13. The method of claim 10, wherein the RNA molecule comprises a sequence as set forth in SEQ ID NO:5 or SEQ ID NO:6.

14. A method of screening for a transglycosylase inhibitor comprising:
(i) contacting a detectable PreQ1 analog with an RNA molecule in the presence of a transglycosylase and a test transglycosylase inhibitor; and
(ii) determining whether the transglycosylase substitutes a guanine moiety from a guanine within the RNA molecule with the detectable PreQ1 analog, wherein the PreQ1 analog is the compound of formula II:

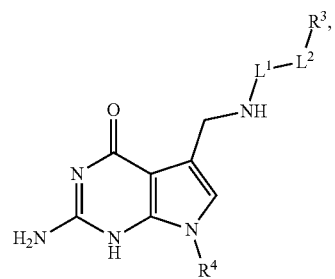

or a pharmaceutically acceptable salt thereof,
wherein:
L¹ is R⁵-substituted alkylene, R⁵-substituted or unsubstituted heteroalkylene, a detectable moiety, R⁵-substituted or unsubstituted cycloalkylene, R⁵-substituted or unsubstituted heterocycloalkylene, R⁵-substituted or unsubstituted arylene, or R⁵-substituted or unsubstituted heteroarylene;

R⁵ is independently oxo, halogen, —CF₃, —CN, —OH, —NH₂, —COOH, —CONH₂, —NO₂, —SH, —SO₃H, —SO₄H, —SO₂NH₂, —NHNH₂, —ONH₂, —NHC═(O)NHNH₂, —NHC═(O) NH₂, —NHSO₂H, —NHC═(O)H, —NHC(O)—OH, —NHOH, —OCF₃, —OCHF₂, R⁶-substituted or unsubstituted alkyl, R⁶-substituted or unsubstituted heteroalkyl, R⁶-substituted or unsubstituted cycloalkyl, R⁶-substituted or unsubstituted heterocycloalkyl, R⁶-substituted or unsubstituted aryl, or R⁶-substituted or unsubstituted heteroaryl;

R⁶ is independently oxo, halogen, —CF₃, —CN, —OH, —NH₂, —COOH, —CONH₂, —NO₂, —SH, —SO₃H, —SO₄H, —SO₂NH₂, —NHNH₂, —ONH₂, —NHC═(O)NHNH₂, —NHC═(O) NH₂, —NHSO₂H, —NHC═(O)H, —NHC(O)—OH, —NHOH, —OCF₃, —OCHF₂, R⁷-substituted or unsubstituted alkyl, R⁷-substituted or unsubstituted heteroalkyl, R⁷-substituted or unsubstituted cycloalkyl, R⁷-substituted or unsubstituted heterocycloalkyl), R⁷-substituted or unsubstituted aryl, or R⁷-substituted or unsubstituted heteroaryl;

L² is R⁸-substituted alkylene, R⁸-substituted or unsubstituted heteroalkylene, a detectable moiety, R⁸-substituted or unsubstituted cycloalkylene, R⁸-substituted or unsubstituted heterocycloalkylene, R⁸-substituted or unsubstituted arylene, or R⁸-substituted or unsubstituted heteroarylene;

R⁸ is independently oxo, halogen, —CF₃, —CN, —OH, —NH₂, —COOH, —CONH₂, —NO₂, —SH, —SO₃H, —SO₄H, —SO₂NH₂, —NHNH₂, —ONH₂, —NHC═(O)NHNH₂, —NHC═(O) NH₂, —NHSO₂H, —NHC═(O)H, —NHC(O)—OH, —NHOH, —OCF₃, —OCHF₂, R⁹-substituted or unsubstituted alkyl, R⁹-substituted or unsubstituted heteroalkyl, R⁹-substituted or unsubstituted cycloalkyl, R⁹-substituted or unsubstituted heterocycloalkyl, R⁹-substituted or unsubstituted aryl, or R⁹-substituted or unsubstituted heteroaryl;

R⁹ is independently oxo, halogen, —CF₃, —CN, —OH, —NH₂, —COOH, —CONH₂, —NO₂, —SH, —SO₃H, —SO₄H, —SO₂NH₂, —NHNH₂, —ONH₂, —NHC═(O)NHNH₂, —NHC═(O) NH₂, —NHSO₂H, —NHC═(O)H, —NHC(O)—OH, —NHOH, —OCF₃, —OCHF$_2$, R$^{10}$-substituted or unsubstituted alkyl, R$^{10}$-substituted or unsubstituted heteroalkyl, R$^{10}$-substituted or unsubstituted cycloalkyl R$^{10}$-substituted or unsubstituted heterocycloalkyl, R$^{10}$-substituted or unsubstituted aryl, or R$^{10}$-substituted or unsubstituted heteroaryl;

R$^3$ is a detectable moiety, a biomolecule, hydrogen, halogen, —CN, R$^{11}$-substituted or unsubstituted alkyl, R$^{11}$-substituted or unsubstituted heteroalkyl, R$^{11}$ substituted or unsubstituted cycloalkyl, R$^{11}$-substituted or unsubstituted heterocycloalkyl, R$^{11}$-substituted or unsubstituted aryl, or R$^{11}$-substituted or unsubstituted heteroaryl;

R$^{11}$ is independently oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, R$^{12}$-substituted or unsubstituted alkyl, R$^{12}$-substituted or unsubstituted heteroalkyl, R$^{12}$-substituted or unsubstituted cycloalkyl, R$^{12}$-substituted or unsubstituted heterocycloalkyl, R$^{12}$-substituted or unsubstituted aryl, or R$^{12}$-substituted or unsubstituted heteroaryl;

R$^{12}$ is independently oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, R$^{13}$-substituted or unsubstituted alkyl, R$^{13}$-substituted or unsubstituted heteroalkyl, R$^{13}$-substituted or unsubstituted cycloalkyl, R$^{13}$-substituted or unsubstituted heterocycloalkyl, R$^{13}$-substituted or unsubstituted aryl, or R$^{13}$-substituted or unsubstituted heteroaryl;

R$^7$, R$^{10}$, and R$^{13}$ are independently oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, or unsubstituted heteroaryl; and R$^4$ is hydrogen.

15. The method of claim 14, wherein the test transglycosylase inhibitor is a small molecule or a biomolecule.

16. The method of claim 15, wherein the small molecule is an organic molecule having a molecular weight of 900 Da or less.

17. The method of claim 14, wherein the determining comprises detecting substitution of the guanine moiety from the guanine within the RNA sequence with the PreQ1 analog thereby identifying a transglycosylase inhibitor.

18. The method of claim 17, wherein the detecting comprises determination of fluorescence emission intensity.

19. The method of claim 14, wherein L$^1$ is substituted unbranched alkylene or substituted or unsubstituted unbranched heteroalkylene.

20. The method of claim 14, wherein R$^3$ is a dye, a fluorophore, an antibody, a polypeptide, a protein, a nucleic acid molecule, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

21. The method of claim 14, wherein R$^3$ is thiazole orange or a derivative thereof.

22. The method of claim 14, wherein R$^3$ is biocytin, biotin, a boron-dipyrromethene dye or a cyanine dye.

* * * * *

SEQUENCE LISTING

<160> NUMBER OF SEQ ID NOS: 8

<210> SEQ ID NO 1
<211> LENGTH: 1311
<212> TYPE: DNA
<213> ORGANISM: Escherichia coli

<400> SEQUENCE: 1

```
ctgcagggcc agtgaattcg agctcggtac ctcgcgaatg catctagata tcggatccta    60
atacgactca ctatagggaa taattttgtt taactttaag aaggagatat aatgaaattt   120
gaactggaca ccaccgacgg tcgcgcacgc cgtggccgcc tggtctttga tcgtggcgta   180
gtggaaacgc cttgttttat gcctgttggc acctacggca ccgtaaaagg gatgacgccg   240
gaagaagttg aagccactgg cgcgcaaatt atcctcggca cacccttcca cctgtggctg   300
cgcccgggcc aggaaatcat gaaactgcac ggcgatctgc acgatttat gcagtggaag   360
gggccgatcc tcaccgactc cggcggcttc caggtcttca gccttggcga tattcgtaaa   420
```

| | |
|---|---|
| atcaccgaac agggcgtgca cttccgtaac ccgatcaacg gcgatccgat tttcctcgat | 480 |
| cctgaaaaat caatggagat tcagtacgat cttggttcgg atatcgtcat gatctttgat | 540 |
| gagtgtacgc cgtatcctgc tgactgggat tacgcaaaac gctccatgga gatgtctctg | 600 |
| cgttgggcga agcgtagccg tgagcgtttt gacagtctcg gaaacaaaaa tgcgctgttt | 660 |
| ggtatcatcc agggcagcgt ttacgaagat ttacgtgata tttctgttaa aggtctggta | 720 |
| gatatcggtt ttgatggcta cgctgtcggc ggtctggctg tgggtgagcc gaaagcagat | 780 |
| atgcaccgca ttctggagca tgtatgcccg caaattccgg cagacaaacc gcgttacctg | 840 |
| atgggcgttg gtaaaccaga agacctggtt gaaggcgtac gtcgtggtat cgatatgttt | 900 |
| gactgcgtaa tgccaacccg caacgcccga atggtcatt tgttcgtgac cgatggcgtg | 960 |
| gtgaaaatcc gcaatgcgaa gtataagagc gatactggcc cactcgatcc tgagtgtgat | 1020 |
| tgctacacct gtcgcaatta ttcacgcgct tacttgcatc atcttgaccg ttgcaacgaa | 1080 |
| atattaggcg cgcgactcaa caccattcat aaccttcgtt actaccagcg tttgatggcg | 1140 |
| ggtttacgca aggctattga agagggtaaa ttagagagct cgtaactga ttttaccag | 1200 |
| cgtcaggggc gagaagtacc acctttgaac gttgatcacc atcaccacca tcactaaaaa | 1260 |
| ggcgggcctc gagcaaagcc cgccgaaagg cgggcttttc tgtgtaagct t | 1311 |

<210> SEQ ID NO 2
<211> LENGTH: 897
<212> TYPE: DNA
<213> ORGANISM: Artificial Sequence
<220> FEATURE:
<223> OTHER INFORMATION: Synthetic polynucleotide

<400> SEQUENCE: 2

| | |
|---|---|
| gatatctaat acgactcact atagggaata ttttgtttaa actttaagaa ggagatataa | 60 |
| tggtgagcaa gggcgaggag gataacatgg ccatcatcaa ggagttcatg cgcttcaagg | 120 |
| tgcacatgga gggctccgtg aacgccacg agttcgagat cgagggcgag ggcgagggcc | 180 |
| gcccctacga gggcacccag accgccaagc tgaaggtgac caagggtggc cccctgccct | 240 |
| tcgcctggga catcctgtcc ctcagttca tgtacggctc caaggcctac gtgaagcacc | 300 |
| ccgccgacat ccccgactac ttgaagctgt ccttccccga gggcttcaag tgggagcgcg | 360 |
| tgatgaactt cgaggacggc ggcgtggtga ccgtgaccca ggactcctcc ctgcaggacg | 420 |
| gcgagttcat ctacaaggtg aagctgcgcg gcaccaactt cccctccgac ggccccgtaa | 480 |
| tgcagaagaa gaccatgggc tgggaggcct cctccgagcg gatgtacccc gaggacggcg | 540 |
| ccctgaaggg cgagatcaag cagaggctga agctgaagga cggcggccac tacgacgctg | 600 |
| aggtcaagac cacctacaag gccaagaagc ccgtgcagct gcccggcgcc tacaacgtca | 660 |
| acatcaagtt ggacatcacc tcccacaacg aggactacac catcgtggaa cagtacgaac | 720 |
| gcgccgaggg ccgccactcc accggcggca tggacgagct gtacaagtaa ccccatgtat | 780 |
| ctaaatcagc acccatcatt ttcatatccc cgcagactgt aaatctgccc ccatgtatct | 840 |
| aaatcagcac ccatcatttt catatccccc gaaaggcggg cttttctgtg tctcgag | 897 |

<210> SEQ ID NO 3
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 3

```
cgcagactct aaatctgccc ccatg                                            25
```

<210> SEQ ID NO 4
<211> LENGTH: 1097
<212> TYPE: DNA
<213> ORGANISM: Artificial Sequence
<220> FEATURE:
<223> OTHER INFORMATION: Synthetic polynucleotide

<400> SEQUENCE: 4

```
gatatctaat acgactcact atagggaata attttgttta actttaagaa ggagatataa      60
tggtgagcaa gggcgaggag gataacatgg ccatcatcaa ggagttcatg cgcttcaagg     120
tgcacatgga gggctccgtg aacggccacg agttcgagat cgagggcgag ggcgagggcc     180
gccctacga gggcacccag accgccaagc tgaaggtgac caagggtggc cccctgccct     240
tcgcctggga catcctgtcc cctcagttca tgtacggctc caaggcctac gtgaagcacc     300
ccgccgacat ccccgactac ttgaagctgt ccttccccga gggcttcaag tgggagcgcg     360
tgatgaactt cgaggacggc ggcgtggtga ccgtgaccca ggactcctcc ctgcaggacg     420
gcgagttcat ctacaaggtg aagctgcgcg gcaccaactt cccctccgac ggccccgtaa     480
tgcagaagaa gaccatgggc tgggaggcct cctccgagcg gatgtacccc gaggacggcg     540
ccctgaaggg cgagatcaag cagaggctga agctgaagga cggcggccac tacgacgctg     600
aggtcaagac cacctacaag gccaagaagc ccgtgcagct gcccggcgcc tacaacgtca     660
acatcaagtt ggacatcacc tcccacaacg aggactacac catcgtggaa cagtacgaac     720
gcgccgaggg ccgccactcc accggcggca tggacgagct gtacaagtaa ccccatgtat     780
ctaaatcagc acccatcatt ttcatatccc cgcagactct aaatctgccc ccatgcgcag     840
actctaaatc tgcccccatg cgcagactct aaatctgccc ccatgcgcag actctaaatc     900
tgcccccatg cgcagactct aaatctgccc ccatgcgcag actctaaatc tgcccccatg     960
cgcagactct aaatctgccc ccatgcgcag actctaaatc tgcccccatg cgcagactct    1020
aaatctgccc ccatgtatct aaatcagcac ccatcatttt catatccccc gaaaggcggg    1080
cttttctgtg tctcgag                                                  1097
```

<210> SEQ ID NO 5
<211> LENGTH: 17
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (7)..(7)
<223> OTHER INFORMATION: Residue is a, u, g, c, or p
<220> FEATURE:
<221> NAME/KEY: misc_feature
<222> LOCATION: (9)..(9)
<223> OTHER INFORMATION: Residue is a, u, g, c, or p

<400> SEQUENCE: 5

```
gcagacngna aaucugc                                                    17
```

<210> SEQ ID NO 6
<211> LENGTH: 25
<212> TYPE: RNA
<213> ORGANISM: Artificial Sequence
<220> FEATURE:
<223> OTHER INFORMATION: Synthetic polynucleotide -continued

```
<400> SEQUENCE: 6
gggagcagac uguaaaucug cuccc                                              25

<210> SEQ ID NO 7
<211> LENGTH: 17
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (7)..(7)
<223> OTHER INFORMATION: Residue is a, u, g, c, or p
<220> FEATURE:
<221> NAME/KEY: misc_feature
<222> LOCATION: (8)..(8)
<223> OTHER INFORMATION: Residue is a, u, g, c, q, or PreQ1, wherein
      PreQ1 is optionally modified
<220> FEATURE:
<221> NAME/KEY: misc_feature
<222> LOCATION: (9)..(9)
<223> OTHER INFORMATION: Residue is a, u, g, c, or p

<400> SEQUENCE: 7
gcagacnnna aaucugc                                                       17

<210> SEQ ID NO 8
<211> LENGTH: 381
<212> TYPE: PRT
<213> ORGANISM: Artificial Sequence
<220> FEATURE:
<223> OTHER INFORMATION: Synthetic polypeptide

<400> SEQUENCE: 8
```

Met Lys Phe Glu Leu Asp Thr Thr Asp Gly Arg Ala Arg Arg Gly Arg
1               5                   10                  15

Leu Val Phe Asp Arg Gly Val Val Glu Thr Pro Cys Phe Met Pro Val
            20                  25                  30

Gly Thr Tyr Gly Thr Val Lys Gly Met Thr Pro Glu Glu Val Glu Ala
        35                  40                  45

Thr Gly Ala Gln Ile Ile Leu Gly Asn Thr Phe His Leu Trp Leu Arg
    50                  55                  60

Pro Gly Gln Glu Ile Met Lys Leu His Gly Asp Leu His Asp Phe Met
65                  70                  75                  80

Gln Trp Lys Gly Pro Ile Leu Thr Asp Ser Gly Gly Phe Gln Val Phe
                85                  90                  95

Ser Leu Gly Asp Ile Arg Lys Ile Thr Glu Gln Gly Val His Phe Arg
            100                 105                 110

Asn Pro Ile Asn Gly Asp Pro Ile Phe Leu Asp Pro Glu Lys Ser Met
        115                 120                 125

Glu Ile Gln Tyr Asp Leu Gly Ser Asp Ile Val Met Ile Phe Asp Glu
    130                 135                 140

Cys Thr Pro Tyr Pro Ala Asp Trp Asp Tyr Ala Lys Arg Ser Met Glu
145                 150                 155                 160

Met Ser Leu Arg Trp Ala Lys Arg Ser Arg Glu Arg Phe Asp Ser Leu
                165                 170                 175

Gly Asn Lys Asn Ala Leu Phe Gly Ile Ile Gln Gly Ser Val Tyr Glu
            180                 185                 190

Asp Leu Arg Asp Ile Ser Val Lys Gly Leu Val Asp Ile Gly Phe Asp
        195                 200                 205

Gly Tyr Ala Val Gly Gly Leu Ala Val Gly Glu Pro Lys Ala Asp Met

```
                210              215                 220
His Arg Ile Leu Glu His Val Cys Pro Gln Ile Pro Ala Asp Lys Pro
225                      230                 235                 240

Arg Tyr Leu Met Gly Val Gly Lys Pro Glu Asp Leu Val Glu Gly Val
                245                 250                 255

Arg Arg Gly Ile Asp Met Phe Asp Cys Val Met Pro Thr Arg Asn Ala
                260                 265                 270

Arg Asn Gly His Leu Phe Val Thr Asp Gly Val Val Lys Ile Arg Asn
            275                 280                 285

Ala Lys Tyr Lys Ser Asp Thr Gly Pro Leu Asp Pro Glu Cys Asp Cys
290                 295                 300

Tyr Thr Cys Arg Asn Tyr Ser Arg Ala Tyr Leu His His Leu Asp Arg
305                 310                 315                 320

Cys Asn Glu Ile Leu Gly Ala Arg Leu Asn Thr Ile His Asn Leu Arg
                325                 330                 335

Tyr Tyr Gln Arg Leu Met Ala Gly Leu Arg Lys Ala Ile Glu Glu Gly
                340                 345                 350

Lys Leu Glu Ser Phe Val Thr Asp Phe Tyr Gln Arg Gln Gly Arg Glu
            355                 360                 365

Val Pro Pro Leu Asn Val Asp His His His His His His
370                 375                 380
```